United States Patent
Soltis et al.

(10) Patent No.: US 11,401,345 B2
(45) Date of Patent: Aug. 2, 2022

(54) HUMANIZED ANTIBODIES TARGETING HUMAN TISSUE FACTOR

(71) Applicant: Purdue Pharma L.P., Stamford, CT (US)

(72) Inventors: Daniel A. Soltis, Cleveland Heights, OH (US); Thomas Mehrling, Riehen (CH); Richard John Buick, Belfast (GB)

(73) Assignee: Purdue Pharma L.P., Stamford, CT (US)

( * ) Notice: Subject to any disclaimer, the term of this patent is extended or adjusted under 35 U.S.C. 154(b) by 99 days.

(21) Appl. No.: 16/763,185

(22) PCT Filed: Nov. 26, 2018

(86) PCT No.: PCT/IB2018/059318
§ 371 (c)(1),
(2) Date: May 11, 2020

(87) PCT Pub. No.: WO2019/102435
PCT Pub. Date: May 31, 2019

(65) Prior Publication Data
US 2020/0385487 A1  Dec. 10, 2020

Related U.S. Application Data

(60) Provisional application No. 62/591,168, filed on Nov. 27, 2017.

(51) Int. Cl.
*C07K 16/36* (2006.01)
*A61K 47/68* (2017.01)
*A61P 35/00* (2006.01)

(52) U.S. Cl.
CPC .......... *C07K 16/36* (2013.01); *A61K 47/6803* (2017.08); *A61K 47/6843* (2017.08); *A61P 35/00* (2018.01); *C07K 2317/24* (2013.01); *C07K 2317/56* (2013.01); *C07K 2317/92* (2013.01); *C07K 2317/94* (2013.01)

(58) Field of Classification Search
CPC  C07K 16/36; C07K 2317/24; C07K 2317/56; C07K 2317/92; C07K 2317/94; A61K 47/6803; A61K 47/6843; A61P 35/00
See application file for complete search history.

(56) References Cited

U.S. PATENT DOCUMENTS

| | | |
|---|---|---|
| 598,877 A | 2/1898 | Rollert |
| 4,444,887 A | 4/1984 | Hoffmann |
| 4,676,980 A | 6/1987 | Segal et al. |
| 4,716,111 A | 12/1987 | Osband et al. |
| 4,816,397 A | 3/1989 | Boss et al. |
| 4,816,567 A | 3/1989 | Cabilly et al. |
| 4,946,778 A | 8/1990 | Ladner et al. |
| 5,223,409 A | 6/1993 | Ladner et al. |
| 5,225,539 A | 7/1993 | Winter |
| 5,258,498 A | 11/1993 | Huston et al. |
| 5,314,995 A | 5/1994 | Fell, Jr. et al. |
| 5,403,484 A | 4/1995 | Ladner et al. |
| 5,413,923 A | 5/1995 | Kucherlapati et al. |
| 5,427,908 A | 6/1995 | Dower et al. |
| 5,474,981 A | 12/1995 | Leder et al. |
| 5,516,637 A | 5/1996 | Huang et al. |
| 5,530,101 A | 6/1996 | Queen et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,625,126 A | 4/1997 | Lonberg et al. |
| 5,633,425 A | 5/1997 | Lonberg et al. |
| 5,658,727 A | 8/1997 | Barbas et al. |
| 5,661,016 A | 8/1997 | Lonberg et al. |
| 5,698,426 A | 12/1997 | Huse |
| 5,733,743 A | 3/1998 | Johnson et al. |
| 5,750,753 A | 5/1998 | Kimae et al. |
| 5,766,883 A | 6/1998 | Ballance et al. |
| 5,780,225 A | 7/1998 | Wigler et al. |
| 5,807,715 A | 9/1998 | Morrison et al. |
| 5,814,318 A | 9/1998 | Lonberg et al. |

(Continued)

FOREIGN PATENT DOCUMENTS

| | | |
|---|---|---|
| EP | 0322094 B1 | 12/1992 |
| EP | 0396387 B1 | 12/1993 |

(Continued)

OTHER PUBLICATIONS

Edwards et al, 2003 J Mol Biol 334:103-118 (Year: 2003).*
Marchalonis et al., Dev & Comp Immunol 2006 30:223-247 (Year: 2006).*
Almagro & Fransson, Frontiers in Bioscience 2008; 13:1619-33 (Year: 2008).*
Sela-Culang, et al., Frontiers in Immunology 2013 vol. 4 Article 302 (Year: 2013).*
Theunissen, et al., Mol. Cancer Ther 2018 17(11) pp. 2412-2426 (Year: 2018).*

(Continued)

*Primary Examiner* — Julie Wu
*Assistant Examiner* — John L Van Druff
(74) *Attorney, Agent, or Firm* — Sterne, Kessler, Goldstein & Fox P.L.L.C.

(57) ABSTRACT

The present disclosure provides humanized antibodies and antibody-drug conjugates that specifically bind to human tissue factor, and which do not inhibit tissue factor mediated blood coagulation compared to a normal plasma control. Further described are methods of making and methods of using the disclosed humanized antibodies and antibody-drug conjugates in the treatment of cancer.

19 Claims, 16 Drawing Sheets
Specification includes a Sequence Listing.

(56) References Cited

U.S. PATENT DOCUMENTS

| | | | |
|---|---|---|---|
| 5,821,047 A | 10/1998 | Garrard et al. |
| 5,876,969 A | 3/1999 | Fleer et al. |
| 5,885,793 A | 3/1999 | Griffiths et al. |
| 5,916,771 A | 6/1999 | Hori et al. |
| 5,939,598 A | 8/1999 | Kucherlapati et al. |
| 5,969,108 A | 10/1999 | McCafferty et al. |
| 6,075,181 A | 6/2000 | Kucherlapati et al. |
| 6,114,598 A | 9/2000 | Kucherlapati et al. |
| 6,602,684 B1 | 8/2003 | Umana et al. |
| 7,659,241 B2 | 2/2010 | Senter et al. |
| 7,993,644 B2 | 8/2011 | Wang |
| 9,504,758 B2 | 11/2016 | Van Delft et al. |
| 9,688,721 B2 | 6/2017 | Cong et al. |
| 9,816,654 B2 | 11/2017 | Hansli et al. |
| 9,821,074 B2 | 11/2017 | Howard et al. |
| 2005/0106139 A1 | 5/2005 | Svendsen et al. |
| 2005/0238649 A1 | 10/2005 | Doronina et al. |
| 2009/0081200 A1 | 3/2009 | Wang |
| 2012/0009181 A1 | 1/2012 | Ab et al. |
| 2012/0237528 A1 | 9/2012 | Almagro et al. |

FOREIGN PATENT DOCUMENTS

| | | |
|---|---|---|
| EP | 0239400 B1 | 8/1994 |
| EP | 0413622 B1 | 2/1998 |
| EP | 0439095 B1 | 5/1998 |
| EP | 1069185 A1 | 1/2001 |
| EP | 0592106 B1 | 11/2004 |
| EP | 0519596 B1 | 2/2005 |
| WO | WO-8912624 A2 | 12/1989 |
| WO | WO-9002809 A1 | 3/1990 |
| WO | WO-9109967 A1 | 7/1991 |
| WO | WO-9110737 A1 | 7/1991 |
| WO | WO-9110741 A1 | 7/1991 |
| WO | WO-9114438 A1 | 10/1991 |
| WO | WO-9201047 A1 | 1/1992 |
| WO | WO-9208495 A1 | 5/1992 |
| WO | WO-9218619 A1 | 10/1992 |
| WO | WO-9311236 A1 | 6/1993 |
| WO | WO-9321232 A1 | 10/1993 |
| WO | WO-9515982 A2 | 6/1995 |
| WO | WO-9520401 A1 | 8/1995 |
| WO | WO-9633735 A1 | 10/1996 |
| WO | WO-9634096 A1 | 10/1996 |
| WO | WO-9713844 A1 | 4/1997 |
| WO | WO-9733899 A1 | 9/1997 |
| WO | WO-9734911 A1 | 9/1997 |
| WO | WO-9824893 A2 | 6/1998 |
| WO | WO-9846645 A2 | 10/1998 |
| WO | WO-9850433 A2 | 11/1998 |
| WO | WO-9923105 A1 | 5/1999 |
| WO | WO-2009036379 A2 | 3/2009 |
| WO | WO-2010105256 A1 | 9/2010 |
| WO | WO-2010115629 A2 | 10/2010 |
| WO | WO-2011133039 A2 | 10/2011 |
| WO | WO-2011157741 A2 | 12/2011 |
| WO | WO-2012009568 A2 | 1/2012 |
| WO | WO-2014043403 A1 | 3/2014 |

OTHER PUBLICATIONS

Aberg, M and Siegbahn, A., "Tissue Factor Non-coagulant Signaling—Molecular Mechanisms and Biological Consequences With a Focus on Cell Migration and Apoptosis," *Journal of Thrombosis and Haemostasis*, 11(5):817-825, Blackwell Publishers, England (May 2013).

Al-Lazikani, B., et al., "Standard Conformations for the Canonical Structures of Immunoglobulins," *Journal of Molecular Biology*, 273(4):927-948, Elsevier, England (Nov. 1997).

Ames, R.S., et al., "Conversion of Murine Fabs Isolated From a Combinatorial Phage Display Library to Full Length Immunoglobulins," *Journal of Immunological Methods*, 184(2):177-186, Elsevier, Netherlands (1995).

Arnon, R., et al., "Monoclonal Antibodies for Immunotargeting of Drugs in Cancer Therapy," in *Monoclonal Antibodies And Cancer Therapy*, Reisfeld, R.A., and Sell, S., eds., pp. 243-256, Alan R. Liss, Inc., New York (1985).

Auerbach, R., et al., "Expression of Organ-specific Antigens on Capillary Endothelial Cells," *Microvascular Research*, 29(3):401-411, Academic Press, United States (May 1985).

Bach, R., et al., "Factor Vii Binding to Tissue Factor in Reconstituted Phospholipid Vesicles: Induction of Cooperativity by Phosphatidylserine," *Biochemistry*, 25(14):4007-4020, American Chemical Society, United States (Jul. 1986).

Baldwin, et al., "Analysis Results, and Future Prospective of the Therapeutic Use of the Radiolabeled Antibody in Cancer Therapy," in *Monoclonal Antibodies for Cancer Detection and Therapy*, eds. Adacemic Press, London, pp. 303-316 (1985).

Banner, D.W., et al., "The Crystal Structure of the Complex of Blood Coagulation Factor Vila With Soluble Tissue Factor," *Nature*, 380(6569):41-46, Nature Publishing Group, England, (Mar. 1996).

Berg, V.D., "The Relationship between Tissue Factor and Cancer Progression: Insights From Bench and Bedside," *Blood*, 119(4):924-932, American Society of Hematology, United States (Jan. 2012).

Breij, E.C.W., "An Antibody-Drug Conjugate That TargetsTissue Factor Exhibits Potent Therapeutic Activity Against a Broad Range of Solid Tumors," *Cancer Research*, 74(4):1214-1226, American Association for Cancer Research, United States (Feb. 2014).

Brinkmann, U., et al., "Phage Display of Disulfide-stabilized Fv Fragments," Journal of Immunological Methods 182(1):41-50, Elsevier, Netherlands (1995).

Buchwald, H., et al., "Long-term, Continuous Intravenous Heparin Administration by an Implantable Infusion Pump in Ambulatory Patients with Recurrent Venous Thrombosis," *Surgery*, 88(4):507-516, Mosby, United States (Oct. 1980).

Callander, N.S., et al., "Immunohistochemical Identification of Tissue Factor In Solid Tumors," *Cancer*, 70(5):1194-1201, Wiley, United States (Sep. 1992).

Caron, P.C., et al., "Engineered Humanized Dimeric Forms of IgG are More Effective Antibodies," *Journal of Experimental Medicine*, 176(4): 1191-1195, Rockefeller University Press, United States (Oct. 1992).

Chen, C., et al., "Characterization of Human Tissue Factor (Tf)-Specific Monoclonal Antibodies Prepared Using A Rapid Immunization Protocol," *Hybridoma*, 24(2):78-85, Mary Ann Liebert, Inc, United States (Apr. 2005).

Chothia, C. and Lesk, A.M., "Canonical Structures for the Hypervariable Regions of Immunoglobulins," *Journal of Molecular Biology*, 196(4):901-917, Elsevier Science, United States (Aug. 1987).

Cocco, E., et al., "Tissue Factor Expression in Ovarian Cancer: Implications for Immunotherapy With Hi-con1, a Factor Vii-iggf(C) Chimeric Protein Targeting Tissue Factor," *Clinical Experimental Metastasis*, 28(7):689-700, Kluwer Academic Publishers, Netherlands (Oct. 2011).

Cockett, M.I., et al., "High Level Expression of Tissue Inhibitor of Metalloproteinases in Chinese Hamster Ovary Cells Using Glutamine Synthetase Gene Amplification.," *Biotechnology*, 8(7):662-667, Nature Pub, United States (1990).

Cohen, R., et al., "Development of Novel Adcs: Conjugation of Tubulysin Analogues to Trastuzumab Monitored by Dual Radiolabeling," *Cancer Research*, 74(20):5700-5710, American Association for Cancer Research, United States (Oct. 2014).

Diamantis, N and Banerji, U., "Antibody-Drug Conjugates—An Emerging Class of Cancer Treatment," *British Journal of Cancer*, 114(4):362-367, Nature Publishing Group on behalf of Cancer Research UK, England (Feb. 2016).

Doria, J.R., et al., "Antibody-Drug Conjugates Bearing Pyrrolobenzodiazepine or Tubulysin Payloads are Immunomodulatory and Synergize with Multiple Immunotherapies," *Cancer Research*, 77(10):2686-2698, American Association for Cancer Research, United States (May 2017).

During, M.J., et al., "Controlled Release of Dopamine From a Polymeric Brain Implant: in Vivo Characterization," *Annals of Neurology*, 25(4):351-356, Wiley-Liss, United States (Apr. 1989).

(56) References Cited

OTHER PUBLICATIONS

Fang, C.H., et al., "Activation of Factor X by Factor Viia Complexed With Human-mouse Tissue Factor Chimeras Requires Human Exon 3," *Thrombosis and Haemostasis*, 76(3):361-368, Thieme, Germany (Sep. 1996).

Fell, H.P., et al., "Genetic Construction and Characterization of a Fusion Protein Consisting of a Chimeric F(ab') With Specificity for Carcinomas and Human IL-2," *Journal of Immunology*, 146(7):2446-2452, American Association of Immunologists, United States (Apr. 1991).

Foecking, M.K., et al., "Powerful and Versatile Enhancer-promoter Unit for Mammalian Expression Vectors," *Gene*, 45(1):101-105, North-Holland, Netherlands (1986).

Folkman, J., et al., "Angiogenesis Inhibition and Tumor Regression Caused By Heparin or a Heparin Fragment In the Presence of Cortisone," *Science*, 221(4612): 719-725, American Association for the Advancement of Science, United States (Aug. 1983).

Folkman, Advances in Cancer Research, eds. Klein and Weinhouse, Academic Press, New York (1985), pp. 175-203.

Folkman, J and Klagsbrun, M., "Angiogenic Factors," *Science*, 235(4787):442-447, American Association for the Advancement of Science, United States (Jan. 1987).

Folkman, J., "Seminars in Medicine of the Beth Israel Hospital, Boston: Clinical Applications of Research on Angiogenesis," *The New England Journal of Medicine*, 333(26):1757-1763, Massachusetts Medical Society, United States (1995).

Gillies, S.D., et al., "Antibody-targeted Interleukin 2 Stimulates T-cell Killing of Autologous Tumor Cells," *Proceedings of the National Academy of Sciences of the United States of America*, 89(4):1428-1432, National Academy of Sciences, United States (1992).

Gillies, S.D., et al., "High-level Expression of Chimeric Antibodies Using Adapted cDNA Variable Region Cassettes," *Journal of Immunological Methods*, 125(1-2):191-202, Elsevier, Netherlands (1989).

Goodson, J.M., "Dental Applications," in *Medical Applications of Controlled Release*, vol. 2, Langer, R.S. and Wise, D.L., eds., pp. 115-138, CRC Press, Inc., United States (1984).

Hammerling, G.J., et al., "Production of Antibody-Producing Hybridomas in the Rodent system," in *Monoclonal Antibodies and T-Cell Hybridomas, Perspectives and technical adnavces*, pp. 563-681, Elsevier, New York (1981).

Hellstrom, et al., "Antibodies for Drug Delivery" in Controlled Drug Delivery, Fundamentals and Applications, 2nd edition, Robinson, J.R., and Lee, V.H., eds., Marcel Dekker, Inc., New York, pp. 623-653 (1987).

Hobbs, J.E., et al., "Alternatively Spliced Human Tissue Factor Promotes Tumor Growth and Angiogenesis in a Pancreatic Cancer Tumor Model," *Thrombosis Research*, 120(20): S13-S21, Pergamon Press, United States (2007).

Holliger, P., et al., "Diabodies: Small Bivalent and Bispecific Antibody Fragments," *Proceedings of the National Academy of Sciences USA*, 90(14):6444-6448, National Academy of Sciences, United States (Jul. 1993).

Howard, M.A. 3rd., "Intracerebral Drug Delivery in Rats With Lesion-induced Memory Deficits," *Journal of Neurosurgery*, 71(1):105-112, American Association of Neurological Surgeons, United States (Jul. 1989).

Huston, U.S., et al., "Protein Engineering of Single-chain Fv Analogs and Fusion Proteins," *Methods in Enzymology*, 203:46-88, Academic Press, United States (1991).

International Search Report for Application No. PCT/IB2018/059318, European patent office, Rijswijk, H.V., dated Feb. 25, 2019, 5 pages.

Jespers, L.S., et al., "Guiding the Selection of Human Antibodies from Phage Display Repertoires to a Single Epitope of an Antigen," *Biotechnology*, 12(9):899-903, Wiley-Blackwell, United States (1994).

Jones, P.T., et al., "Replacing The Complementarity-Determining Regions In A Human Antibody With Those From a Mouse," *Nature*, 321(6069):522-525, Nature Publishing Group, England (May 1986).

Karlin, S. and Altschul, S.E., "Methods for Assessing the Statistical Significance of Molecular Sequence Features by using General Scoring Schemes," *Proceedings of the National Academy of Sciences USA*, 87(6):2264-2268, National Academy of Sciences, United States (Mar. 1990).

Karlin, S, and Altschul, S.F., "Applications and Statistics for Multiple High-scoring Segments in Molecular Sequences," *Proceedings of the National Academy of Sciences USA*, 90(12):5873-5877, National Academy of Sciences, United States (Jun. 1993).

Kasthuri, R.S., et al., "Role of Tissue Factor in Cancer," *Journal of Clinical Oncology*, 27(29):4834-4838, American Society of Clinical Oncology, United States (Oct. 2009).

Kettleborough, C.A., et al., "Isolation of Tumor Cell-specific Single-chain Fv From Immunized Mice Using Phage-antibody Libraries and the Re-construction of Whole Antibodies From These Antibody Fragments," *European Journal of Immunology*, 24(4):952-958, Wiley-VCH, Germany (1994).

Kohler, G. and Milstein, C., "Continuous Cultures of Fused Cells Secreting Antibody of Predefined Specificity," *Nature*, 256(5517):495-497, Macmillan Journals Ltd., England (Aug. 1975).

Kostelny, S.A., et al., "Formation of a Bispecific Antibody by the Use of Leucine Zippers," *The Journal of Immunology*, 148(5):1547-1553, American Association of Immunologists, United States (Mar. 1992).

Langer, R and Peppas, N., "Chemical and Physical Structure of Polymers as Carriers for Controlled Release of Bioactive Agents: A Review," *Journal of Macromolecular Science, Part C Polymer Reviews*, 23(1): 61-126, Marcel Dekker, Inc., New York (1983).

Langer, R., "New Methods of Drug Delivery," *Science*, 249(4976):1527-1533, American Association for the Advancement of Science, United States (Sep. 1990).

Lev, D.C., et al., "Selection of More Aggressive Variants of the GI101A Human Breast Cancer Cell Line: a Model for Analyzing the Metastatic Phenotype of Breast Cancer," *Clinical & Experimental Metastasis*, 20(6):515-523, Kluwer Academic Publishers, Netherlands (2003).

Levy, R.J., et al., "Inhibition of Calcification of Bioprosthetic Heart Valves by Local Controlled-release Diphosphonate," Science, 228(4696):190-192, American Association for the Advancement of Science, United States (Apr. 1985).

Lonberg, N. and Huszar, D., "Human Antibodies from Transgenic Mice," *International Reviews of Immunology*, 13(1):65-93, Informa Healthcare, England (1995).

Lopez-Berestein, G., et al., "Treatment of Systemic Fungal Infections with Liposomal Amphotericin B," in *Liposomes in the Therapy of Infectious Diseases and Cancer*, Lopez-Berestein, G. and Fidler, I.J., eds., pp. 317-327, Alan R. Liss, Inc., United States (1989).

Lopus, M., et al., "Maytansine and Cellular Metabolites of Antibody-maytansinoid Conjugates Strongly Suppress Microtubule Dynamics by Binding to Microtubules," *Molecular Cancer Therapeutics*, 9(10):2689-2699, American Association for Cancer Research, Inc, United States (Oct. 2010).

Maiese, W.M., et al., "Calicheamicins, a Novel Family of Antitumor Antibiotics: Taxonomy, Fermentation and Biological Properties," *The Journal of Antibiotics*, 42(4):558-563, Nature Publishing Group, Japan (Apr. 1989).

Manches, O., et al., "In Vitro Mechanisms of Action of Rituximab on Primary Non-hodgkin Lymphomas," *Blood*, 101:949-954, American Society of Hematology, United States (Feb. 2003).

Marks, J.D., et al., "By-Passing Immunization: Building High Affinity Human Antibodies by Chain Shuffling," *Biotechnology*, 10(7):779-783, Nature Publishing Company, United States (Jul. 1992).

Moldenhauer, G., et al., "Therapeutic Potential of Amanitin-conjugated Anti-epithelial Cell Adhesion Molecule Monoclonal Antibody Against Pancreatic Carcinoma," *Journal of the National Cancer Institute*, 104(8):622-634, Oxford University Press, United States (Apr. 2012).

Morrison, S.L., "Transfectomas Provide Novel Chimeric Antibodies," *Science*, 229(4719):1202-1207, Association for the Advancement of Science, United States (Sep. 1985).

(56) References Cited

OTHER PUBLICATIONS

Morrissey, J.H., et al., "Monoclonal Antibody Analysis of Purified and Cell-associated Tissue Factor," *Thrombosis Research*, 52(3):247-261, Pergamon Press, United States (Nov. 1988).

Moses, M.A and Langer, R., "Inhibitors of Angiogenesis," *Biotechnology*, 9(7):630-634, Nature Publishing, United States (Jul. 1991).

Myers, E.W and Miller, W., "Optical Alignments in linear space," *Computer Applications in the Biosciences*, 4(1):11-17, Oxford University Press, England (1988).

Naramura, M., et al., "Mechanisms of Cellular Cytotoxicity Mediated by a Recombinant Antibody-IL2 Fusion Protein Against Human Melanoma Cells," *Immunology Letters*, 39(1):91-99, Elsevier, Netherlands (Dec. 1993).

NCBI Reference Sequence: NP_001171567.1, "Tissue factor isoform 2 precursor [*Homo sapiens*]," Genpept, available at: https://www.ncbi.nlm.nih.gov/protein/np_001171567, 3 pages.

NCBI Reference Sequence: NP_001984.1, tissue factor isoform 1 precursor [*Homo sapiens*], Genpept, available at: https://www.ncbi.nlm.nih.gov/protein/np_001984, 3 pages.

Needleman, S.B. and Wunsch, C.D., "A General Method Applicable to the Search for Similarities in the Amino Acid Sequence of Two Proteins," *Journal of Molecular Biology*, 48(3):443-453, Academic Press, England (Mar. 1970).

Neuberger, M.S., et al., "Recombinant Antibodies Possessing Novel Effector Functions," *Nature*, 312(5995):604-608, Nature Publishing Group, England (1984).

Ogawa, K., et al., "Establishment of Rat Hepatocellular Carcinoma Cell Lines With Differing Metastatic Potential in Nude Mice," *International Journal of Cancer*, 91(6):797-802, Wiley-Liss, United States (Mar. 2001).

Ohta, S., et al., "Antitumor Effects of a Novel Monoclonal Antibody With High Binding Affinity to Ganglioside Gd3," *Cancer Immunology, Immunotherapy*, 36(4):260-266, Springer Verlag, Germany (1993).

Oi, V.T. and Morrison, S.L., "Chimeric Antibodies," *BioTechniques*, 4(3):214-221, Future Science Group, United Kingdom (1986).

Padlan, E.A., "A Possible Procedure for Reducing the Immunogenicity of Antibody Variable Domains While Preserving their Ligand-binding Properties," *Molecular Immunology*, 28(4-5):489-498, Pergamon Press., England (Apr. 1991).

Patz, A., "Clinical and Experimental Studies on Retinal Neovascularization. XXXIX Edward Jackson Memorial Lecture," *American Journal of Ophthalmology*, 94(6):715-743, Elsevier Science, United States (Dec. 1982).

Pasquier. L., "Evolution of the Immune System," in Fundamental Immunology, 2$^{nd}$ edition, Chapter 7, pp. 139-165, Paul, W.E., ed., Raven Press, New York (1989).

Perez, H.L., et al., "Antibody-drug Conjugates: Current Status and Future Directions," *Drug Discovery Today*, 19(7):869-881, Elsevier Science Ltd., England (Jul. 2014).

Persic, L., et al., "An Integrated Vector System for the Eukaryotic Expression of Antibodies or Their Fragments After Selection From Phage Display Libraries," *Gene*, 187(1):9-18, Elsevier/North-Holland, Netherlands (1997).

Polakis, P., "Antibody Drug Conjugates for Cancer Therapy," *Pharmacological Reviews*, 68(1):3-19, American Society for Pharmacology and Experimental Therapeutics, United States (2016).

Rastinejad, F., et al., "Regulation of the Activity of a New Inhibitor of Angiogenesis by a Cancer Suppressor Gene," *Cell*, 56(3):345-355, Cell Press, United States (Feb. 1989).

Reff, M.E., et al., "Depletion of B Cells in Vivo by a Chimeric Mouse Human Monoclonal Antibody to CD20," *Blood*, 83(2):435-445, American Society of Hematology, United States (Jan. 1994).

Riechmann, L., et al., "Reshaping Human Antibodies For Therapy," *Nature*, 332(6162):323-327, Nature Publishing Group, England (Mar. 1988).

Roguska, M.A., et al., "A Comparison of Two Murine Monoclonal Antibodies Humanized by Cdr-grafting and Variable Domain Resurfacing," *Protein Engineering*, 9(10):895-904, Oxford University Press, England (Oct. 1996).

Roguska, M.A., et al., "Humanization of Murine Monoclonal Antibodies Through Variable Domain Resurfacing," *Proceedings of the National Academy of Sciences of the United States of America*, 91(3):969-973, National Academy of Sciences, United States (Feb. 1994).

Ruf, W., et al., "Tissue Factor and Cell Signalling in Cancer Progression and Thrombosis," *Journal of Thrombosis and Haemostasis*, 9(Suppl 1): 306-315, Blackwell Pub, England (Jul. 2011).

Sato, R., et al., "Preparation and Characterization of Anti-tissue Factor Single-chain Variable Fragment Antibody for Cancer Diagnosis," *Cancer Science*, 105(12):1631-1637, Wiley Publishing on behalf of the Japanese Cancer Association, England (Dec. 2014).

Saudek, C.D., et al., "A Preliminary Trial of the Programmable Implantable Medication System for Insulin Delivery," *The New England Journal of Medicine*, 321(9):574-579, Massachusetts Medical Society, United States (Aug. 1989).

Sefton, M.V., "Implantable Pumps," *Critical Reviews in Biomedical Engineering*, 14(3):201-240, Begell House, United States (1987).

Shopes, B., "A Genetically Engineered Human Igg Mutant With Enhanced Cytolytic Activity," *Journal of Immunology*, 148(9):2918-2922, American Association of Immunologists, United States (May 1992).

Shu, L., et al., "Secretion of a Single-gene-encoded Immunoglobulin From Myeloma Cells," *Proceedings of the National Academy of Sciences of the USA*, 90(17):7995-7999, National Academy of Sciences, United States (1993).

Skerra, A. and Pluckthun, A., "Assembly of a Functional Immunoglobulin Fv Fragment in *Escherichia coli*," *Science*, 240(4855):1038-1041, Association for the Advancement of Science, United States (May 1988).

Smith, T.F. and Waterman, M.S., "Comparison of Biosequences," *Advances in Applied Mathematics*, 2(4):482-489, Academic Press, Inc., United States (Dec. 1981).

Songsivilai, S. and Lachmann, P.J., "Bispecific Antibody: A Tool for Diagnosis and Treatment of Disease," *Clinical and Experimental Immunology*, 79(3):315-321, Blackwell Scientific Publications, England (1990).

Stevenson, G.T., et al., "A Chimeric Antibody With Dual Fc Regions (bisFabFc) Prepared by Manipulations at the IgG Hinge," *Anti-cancer Drug Design*, 3(4):219-230, Oxford University Press, United States (1989).

Studnicka, G.M., et al., "Human-Engineered Monoclonal Antibodies Retain Full Specific Binding Activity By Preserving Non-CDR Complementarity-Modulating Residues," *Protein Engineering*, 7(6):805-814, Oxford University Press, England (1994).

Takahashi, T., et al., "Human Fas Ligand: Gene Structure, Chromosomal Location and Species Specificity," *International Immunology*, 6(10):1567-1574, Oxford University Press, England (Oct. 1994).

Takeda, S., et al., "Construction of Chimaeric Processed Immunoglobulin Genes Containing Mouse Variable and Human Constant Region Sequences," *Nature*, 314(6010):452-454, Nature Publishing Group, England (1985).

Thorpe, P.E. and Ross, W.C., "The Preparation and Cytotoxic Properties of Antibody-toxin Conjugates," *Immunological Reviews*, 62:119-158, Blackwell, England (1982).

Tian, F., et al., "Reduction in Smad2/3 Signaling Enhances Tumorigenesis but Suppresses Metastasis of Breast Cancer Cell Lines," *Cancer Research*, 63(23):8284-8292, American Association for Cancer Research, United States (Dec. 2003).

Traunecker, A., et al., "Bispecific single chain molecules (Janusins) target cytotoxic lymphocytes on HIV infected cells," The EMBO Journal, 10(12):3655-3659, Wiley Blackwell, England (Dec. 1991).

Traunecker, A., et al., "Janusin: New Molecular Design for Bispecific Reagents," *International Journal of Cancer*, 7:51-52, Alan R. Liss, Inc., United States (1992).

Ulukan, H and Swaan, P.W., "Camptothecins: a review of their chemotherapeutic potential," *Drugs*, 62(14):2039-2057, Springer International, New Zealand (2002).

Vera, G., et al., "Cernunnos Deficiency Reduces Thymocyte Life Span and Alters the T Cell Repertoire in Mice and Humans," *Molecular and Cellular Biology*, 33(4):701-711, American Society for Microbiology, United States (Feb. 2013).

(56) References Cited

OTHER PUBLICATIONS

Verhoeyen, M., et al., "Reshaping Human Antibodies: Grafting an Antilysozyme Activity," *Science*, 239(4847):1534-1536, American Association for the Advancement of Science, United States (Mar. 1988).

Wang, B., et al., "Human Single-chain Fv Immunoconjugates Targeted to a Melanoma-associated Chondroitin Sulfate Proteoglycan Mediate Specific Lysis of Human Melanoma Cells by Natural Killer Cells and Complement," *Proceedings of the National Academy of Sciences of the United States of America*, 96(4):1627-1632, National Academy of Sciences, United States (Feb. 1999).

Watanabe, C.M., et al., "Transcriptional Effects of the Potent Enediyne Anti-cancer Agent Calicheamicin Gamma(I)(1)," *Chemistry & Biology*, 9(2):245-251, Elsevier, United States (Feb. 2002).

Wolff, E.A., et al., "Monoclonal Antibody Homodimers: Enhanced Antitumor Activ monoclonal Antibody Homodimers: Enhanced Antitumor Activity in Nude Mice Ity in Nude Mice," *Cancer Research*, 53(11):2560-2555, American Association for Cancer Research, United States (Jun. 1993).

Wu, G.Y and Wu, C.H., "Receptor-Mediated In Vitro Gene Transformation by a Soluble DNA Carrier System," *Journal of Biological Chemistry*, 262(10):4429-4432, American Society for Biochemistry and Molecular Biology, United States (Apr. 1987).

Zhang, Q., "Factor Vii Light Chain-targeted Lidamycin Targets Tissue Factor-overexpressing Tumor Cells for Cancer Therapy," *International Journal of Molecular Medicine*, 29(3):409-415, D.A. Spandidos, Greece (Mar. 2012).

Zisman, A., et al., "LABAZ1: a Metastatic Tumor Model for Renal Cell Carcinoma Expressing the Carbonic Anhydrase Type 9 Tumor Antigen," *Cancer Research*, 63(16):4952-4959, American Association for Cancer Research, United States (Aug. 2003).

Crown Bioscience Symposium on Translational Oncology and the Impact of Immuno-Oncology on Drug Discovery and Clinical Development—Agenda (Munich, Germany, Nov. 28, 2016).

Guggi, D. "B278—an Antibody Drug Conjugate on the pathway to the clinic," presentation at the Crown Bioscience Symposium on Translational Oncology and the Impact of Immuno-Oncology on Drug Discovery and Clinical Development (Munich, Germany, Nov. 28, 2016).

\* cited by examiner

```
ATGGAGACCCCTGCCTGGCCCCGGTCCCCGCGCCCGAGACCGCGTCGCTCGGACGCTC
 M   E   T   P   A   W   P   R   V   P   R   P   E   T   A   V   A   R   T   L
CTGCTCGGCTGGGTCTTCGCCCAGTGCGGCCGCGCTTCAGGCACTACAAATACTGTGCA
 L   G   W   V   F   A   Q   V   A   G   A   S   G   T   N   T   V   A
GCATATAATTTAACTTGGAAATCAACTAATTTCAAGACAATTTGGAGTGGAACCCAAA
 A   Y   N   L   T   W   K   S   T   N   F   K   T   I   L   E   W   E   P   K
CCCGTCAATCAAGTCTACACTGTTCAAATAAGCACTAAGTCAGGAGATTGGAAAGCAAA
 P   V   N   Q   V   Y   T   V   Q   I   S   T   K   S   G   D   W   K   S   K
TGCTTTTACACAGACACAGAGTGTGACCTCACCGAGATTGTGAAGGATGTGAAG
 C   F   Y   T   D   T   E   C   D   L   T   D   E   I   V   K   D   V   K
CAGACGTACTTGGCACGGGTCTTCTCCCAGAGTTCACCACCTTACCTGGAGACAAACCTC
 Q   T   Y   L   A   R   V   F   S   Y   P   A   G   N   V   E   S   T   G   S
GCTGGGGAGCCTCTGTATGAGAACTCCCCAGAGTTCACCACCTTACCTGGAGACAAACCTC
 A   G   E   P   L   Y   E   N   S   P   E   F   T   P   Y   L   E   T   N   L
GGACAGCCAACAATTCAGAGTTTGAACAGTTGGAACAAAAGTGAATGTGACCGTAGAA
 G   Q   P   T   I   Q   S   F   E   Q   V   G   T   K   V   N   V   T   V   E
GATGAACGGACTTTAGTCAGAAGGAACAACACTTTCCTAAGCCTCCGGGATGTTTTGGC
 D   E   R   T   L   V   R   R   N   N   T   F   L   S   L   R   D   V   F   G
AAGGACTTAATTTATACACTTTATTATTGGAAATCTTCAAGTTCAGGAAAGAAAACAGCC
 K   D   L   I   Y   T   L   Y   Y   W   K   S   S   S   G   K   K   T   A
AAAACAAACACTAATGAGTTTTTGATTGATGTGGATAAAGGAGAAAACTACTGTTTCAGT
 K   T   N   E   F   L   I   D   V   D   K   G   E   N   Y   C   F   S
GTTCAAGCAGTGATTCCCTCCGAACAGTTAACCGGAAGAGTACAGACCCGGTAGAG
 V   Q   A   V   I   P   S   R   T   V   N   R   K   S   T   D   S   P   V   E
TGTATGGGCCAGGAGAAAGGGGAATTCAGAGAAAGAGGATCCCACCATCACCATCACCAT
 C   M   G   Q   E   K   G   E   F   R   E   R   G   S   H   H   H   H   H   H
TAA
 *
```

FIG. 3A

GAG GTC CAG CTG CAG CAA TCT GGA GCT GAG CTG ATG AAG
E   V   Q   L   Q   Q   S   G   A   E   L   M   K

CCT GGG GCC TCA GTG AAG ATA TCC TGC AAG GCT ACT GGC
P   G   A   S   V   K   I   S   C   K   A   T   G

TAC ACA TTC AGT AGC TAC TGG ATA GAG TGG GTA AAG CAG
Y   T   F   S   S   Y   W   I   E   W   V   K   Q

AGG CCT GGA CAT GGC CTT GAG TGG ATT GGA GAG ATT TTA
R   P   G   H   G   L   E   W   I   G   E   I   L

CCT GGA AGT AGT ACT AAG TAC AAT GAG AAG TTC AAG
P   G   S   S   T   K   Y   N   E   K   F   K

GGC AAG GCC ACA TTC ACT GCA GAT ACA TCC TCC AAC ACA
G   K   A   T   F   T   A   D   T   S   S   N   T

GCC TAC ATG CAA CTC AGC AGC CTG ACA TCT GAG GAC TCT
A   Y   M   Q   L   S   S   L   T   S   E   D   S

GCC GTC TAT TAC TGT GCA AGA GAT TAT TAC TAC GGT AGT
A   V   Y   Y   C   A   R   D   Y   Y   Y   G   S

AGC TAC GGG TTT GCT TAC TGG GGC CAA GGG ACT CTG GTC
S   Y   G   F   A   Y   W   G   Q   G   T   L   V

ACT GTC TCG AGT
T   V   S   S

FIG. 3B

```
CAG GCT GTT GTG ACT CAG GAA TCT GCA CTC ACC ACA TCA
 Q   A   V   V   T   Q   E   S   A   L   T   T   S
CCT GGT GAA ACA GTC ACA CTC ACT TGT CGC TCA AGT ACT
 P   G   E   T   V   T   L   T   C   R   S   S   T
GGG GCT GTT ACA ACT AGT AAC TAT GCC AAC TGG GTC CAA
 G   A   V   T   T   S   N   Y   A   N   W   V   Q
GAA AAA CCA GAT CAT TTA TTC ACT GGT CTA ATA GGT GGT
 E   K   P   D   H   L   F   T   G   L   I   G   G
ACC AAC AAC CGA GGT CCA GGT GTT CCT GCC AGA TTC TCA
 T   N   N   R   G   P   G   V   P   A   R   F   S
GGC TCC CTG ATT GGA GAC AAG GCT GCC CTC ACC ATC ACA
 G   S   L   I   G   D   K   A   A   L   T   I   T
GGG GCA CAG ACT GAG GAT GAG GCA GTA TAT TTC TGT GCT
 G   A   Q   T   E   D   E   A   V   Y   F   C   A
CTA TGG TAC AGC AAC CAT TGG GTG TTC GGT GGA GGA ACC
 L   W   Y   S   N   H   W   V   F   G   G   G   T
AAA CTG ACT GTC CTA GGT
 K   L   T   V   L   G
```

FIG. 4A

GAGGTCCAGCTGCAACAGTCGGGAGCAGAGGTGATGAAGCCTCAGTGAAGATT
E  V  Q  L  Q  Q  S  G  A  E  V  M  K  P  G  A  S  V  K  I
AGCTGCAAAGCCTCGGGATACACTTTCTCGTCATACTGGATTGAATGGGTCAAACAGGCC
S  C  K  A  S  G  Y  T  F  S  S  Y  W  I  E  W  V  K  Q  A
CCCGGCCAAGGACTGGAGTGGATTGGCGAAATCCTTCCTGGGAGCGCCTCGACCAAGTAC
P  G  Q  G  L  E  W  I  G  E  I  L  P  G  S  A  S  T  K  Y
AACGAGAAGTTCAAGGGACGCGTGACATTCACCGCCGATACATCCACCAACACTGCCTAC
N  E  K  F  K  G  R  V  T  F  T  A  D  T  S  T  N  T  A  Y
ATGGAGCTTAGCTCATTGCGGTCCGAGGATACCGCTGTATTGTGCGCGGGACTAC
M  E  L  S  S  L  R  S  E  D  T  A  V  Y  Y  C  A  R  D  Y
TATTACGGCTCCCTCATACGGCTTCGCATACTGGGACAGGGTACCTTGGTCACGGTGTCC
Y  Y  G  S  S  Y  G  F  A  Y  W  G  Q  G  T  L  V  T  V  S
TCC
S

FIG. 4B

```
CAGGCTGTGGTCACTCAGGAGCCTTCGCTGACTGTCAGCCCGTGACCCTG
 Q   A   V   V   T   Q   E   P   S   L   T   V   S   P   G   G   T   V   T   L
ACCTGTCGCTCCCTCAACTGGAGCAGTGACCACCTCCAACTACGCGAACTGGGTGCAGCAG
 T   C   R   S   S   T   G   A   V   T   S   N   Y   A   N   W   V   Q   Q
AAACCCGGCCAACTTCCTAAGGGACTGATCTCCGGCACTAACAACAGGGACCTTGGACC
 K   P   G   Q   L   P   K   G   L   I   S   G   T   N   N   R   G   P   W   T
ACCGCCCGGTTCTCCGGTTCCATCCTTGGGGACAAGGCGGTGCTGACACTGTGGGGGCC
 T   A   R   F   S   G   S   I   L   G   D   K   A   V   L   T   L   W   G   A
CACACGGAGGACGAGGCCGTCTACTACTGCGCTCTGGTACTCCAACCATTGGGTGTTT
 H   T   E   D   E   A   V   Y   Y   C   A   L   W   Y   S   N   H   W   V   F
GGCGGAGGCACTAAGTTGACCGTGCTGGGC
 G   G   G   T   K   L   T   V   L   G
```

FIG. 5A

```
                        VL-CDR1                                                    50
        1
VL0  (1) QAVVTQESALTTSPGETVTLTCRSSTGAVTTSNYANWVQEKPDHLFTGLI
VL3  (1) QAVVTQEPSLTVSPGGSVTLTCRSSTGAVTTSNYANWIQQKPGQGPKTLI
VL5  (1) QAVVTQEPSLTVSPGGSVTLTCRSSTGAVTTSNYANWVQQKPGQTPTSLI
VL6  (1) QAVVTQEPSLTVSPGGTVTLTCRSSTGAVTTSNYANWVQEKPGHGFKGLI
VL7  (1) QAVVTQEPSLTVSPGGTVTLTCRSSTGAVTTSNYANWVQQKPGQLPKGLI
VL8  (1) QSALIQPPSVSGSPGQSVTISCRSSTGAVTTSNYANWVQQHPGTVPKPMI

VL-CDR2                                         VL-CDR3
        51                                                           100
VL0 (51) GGTNNRGPGVPARFSGSLIGDKAALTITGAQTEDEAVYFCALWYSNHWVF
VL3 (51) SGTNNRGPWTTARFSGSILGDKAVLTLWGAHAEDEADYCALWYSNHWVF
VL5 (51) SGTNNRGPWTPARFSGSILGDKAVLTLWGAHAEDEADYFCALWYSNHWVF
VL6 (51) SGTNNRGPWTTARFSGSILGDKAVLTLWGAHAEDEADYFCALWYSNHWVF
VL7 (51) SGTNNRGPWTTARFSGSILGDKAVLTLWGAHTEDEAVYYCALWYSNHWVF
VL8 (51) YGTNNRGPGVPDRFSGSKSGNTASMTISGLQAEDEADYFCALWYSNHWVF

101
VL0 (101) GGGTKLTVLG
VL3 (101) GGGTHLTVQG
VL5 (101) GGGTKLTVLG
VL6 (101) GGGTKLTVLG
VL7 (101) GGGTKLTVLG
VL8 (101) GGGTKLTVLG
```

FIG. 5B

```
                                                                VH-CDR1
         1                                          50
VH0   (1) EVQLQQSGAELMKPGASVKISCKATGYTFSSYWIEWVKQRPGHGLEWIGE
VH4   (1) QVQLQESGAEVKKPGASVKVSCKASGYTFSSYWIEWVRQAPGQGLEWMGE
VH5   (1) QVQLQESGAEVKKPGASVKVSCKASGYTFSSYWIEWVRQAPGQGLEWMGE
VH6   (1) EVQLQQSGAEVMKPGASVKISCKASGYTFSSYWIEWVKQAPGQGLEWIGE

VH-CDR2                         100
VH0  (51) ILPGSASTKYNEKFKGKATFTADTSSNTAYMQLSSLTSEDSAVYYCARDY
VH4  (51) ILPGSASTKYNEKFKGRVTMTRDTSTSTVYMELSSLRSEDTAVYYCARDY
VH5  (51) ILPGSASTKYNEKFKGRVTMTADTSTNTVYMELSSLRSEDTAVYYCARDY
VH6  (51) ILPGSASTKYNEKFKGRVTFTADTSTNTAYMELSSLRSEDTAVYYCARDY

VH-CDR3    121
VH0 (101) YYGSSYGFAYWGQGTLVTVSS
VH4 (101) YYGSSYGFAYWGQGTLVTVSS
VH5 (101) YYGSSYGFAYWGQGTLVTVSS
VH6 (101) YYGSSYGFAYWGQGTLVTVSS
```

HUMANIZED ANTIBODIES TARGETING HUMAN TISSUE FACTOR

BACKGROUND OF THE INVENTION

Field of the Invention

The present disclosure is in the fields of humanized antibodies, antibody-drug conjugates, and cancer therapy. In particular, the disclosure relates to humanized antibodies capable of specifically binding human tissue factor without inhibiting normal tissue factor-mediated blood coagulation, methods of making and methods of use thereof, including use as antibody-drug conjugates, in the treatment of cancer.

Related Art

Tissue factor (TF), also known as thromboplastin, coagulation factor III, or CD142, is a 47-kDa transmembrane glycoprotein that, together with its native ligand, Factor VIIa, initiates the blood coagulation cascade in vivo. TF has a 219 amino acid extracellular region, a 23 amino acid transmembrane region, and a 21 amino acid cytoplasmic region. The extracellular region of TF is required for procoagulant function and consists of two fibronectin III-like domains and a distribution of disulfide bridges characteristic of class-II cytokine and interferon receptors. The cytoplasmic region of TF contains three serine residues that can be phosphorylated and have been implicated in cell signaling. Aberg, M. and Siegbahn, A., *J Thromb Haemost* 11: 817-825 (2013).

TF is expressed by cells that are normally not exposed to flowing blood, such as subendothelial cells (e.g., smooth muscle cells) and cells surrounding blood vessels (e.g., fibroblasts). TF is, however, expressed by many types of tumor cells including tumor associated vascular endothelial cells, where TF is exposed to blood proteins. TF may contribute to metastasis, tumor growth, and tumor angiogenesis. See, van den Berg, Y. W., *Blood* 119:924-32 (2012); Kasthuri, R. S. et al., *J Clin Oncol.* 27:4834-8 (2009). Importantly, TF dependent activation of coagulation has been implicated in cancer associated thrombosis and metastasis. Id. In addition to its procoagulant activity, TF has cell signaling properties. Formation of the TF:FVIIa complex on the surface of tumor cells leads to cleavage and activation of the G-protein-coupled receptor PAR2. The TF:FVIIa-PAR2 signaling pathway appears to promote tumor growth and tumor angiogenesis. Id.

Expression levels of TF have also been correlated with tumor cell aggressiveness. Lima, L. G. and Monteiro R. Q., *Biosci. Rep.* 33: 701-710 (2013); Ruf, W. et al., *J Thromb Haemost.*: 9 (Suppl 1): 306-315 (2011). Furthermore, human TF also exists in a soluble alternatively-spliced form, asHTF. It has been found that asHTF promotes tumor growth (Hobbs et al., *Thrombosis Res.* 120: S13-S21 (2007)).

Antibodies that bind to the TF-FVIIa interaction site can inhibit TF-FVIIa interaction, thus inhibiting or blocking blood coagulation. However, when large quantities of those antibodies are used for tumor therapy, effective bleeding control in patients may be compromised.

Although much progress has been made in the field of oncology, there remains a need for improved cancer treatments. Accordingly, the present disclosure provides humanized antibodies, antibody-drug conjugates, and pharmaceutical compositions that specifically target human tissue factor, for use in the treatment of cancer without inhibiting normal tissue factor-mediated blood coagulation.

SUMMARY OF THE INVENTION

In one aspect, the present invention provides a humanized antibody or antigen-binding fragment thereof that specifically binds to human tissue factor, wherein the humanized antibody comprises: (i) a heavy chain variable region or antigen binding fragment thereof that has at least 90% sequence identity to an amino acid sequence selected from SEQ ID NOs: 9-11; (ii) a light chain variable region or antigen-binding fragment thereof that has at least 90% sequence identity to an amino acid sequence selected from SEQ ID NOs: 12-16; and (iii) wherein said humanized antibody or antigen binding fragment thereof does not inhibit tissue factor mediated blood coagulation compared to a normal plasma control.

In some embodiments, the humanized antibody or antigen-binding fragment thereof comprises a heavy chain variable region having at least 95% sequence identity to an amino acid sequence selected from SEQ ID NOs: 9-11.

In some embodiments, the humanized antibody or antigen-binding fragment thereof comprises a heavy chain variable region having an amino acid sequence selected from SEQ ID NOs: 9-11.

In some embodiments, the humanized antibody or antigen-binding fragment thereof comprises a heavy chain variable region having the amino acid sequence of SEQ ID NO: 9.

In some embodiments, the humanized antibody or antigen-binding fragment thereof comprises a light chain variable region having at least 95% sequence identity to an amino acid sequence selected from SEQ ID NOs: 12-16.

In some embodiments, the humanized antibody or antigen-binding fragment thereof comprises a light chain variable region having the amino acid sequence selected from SEQ ID NOs: 12-16.

In some embodiments, the humanized antibody or antigen-binding fragment thereof comprises a light chain variable region having an amino acid sequence of SEQ ID NO: 12.

In some embodiments, the humanized antibody is a full-length antibody.

In some embodiments, the humanized antibody or antigen-binding fragment thereof specifically binds to human tissue factor with a $K_D$ from about 1.0 nM to about 10 nM.

In one aspect, the present disclosure provides an isolated polynucleotide encoding the light chain or heavy chain variable region of a humanized antibody or antigen binding fragment described herein. In some embodiments, the isolated polynucleotide encodes a full length light chain or full length heavy chain of a humanized antibody or antigen binding fragment disclosed herein.

In one aspect, the present disclosure provides a vector comprising a polynucleotide disclosed herein.

In one aspect, the present disclosure provides a host cell comprising a vector disclosed herein. In some embodiments, the host cell is genetically engineered to comprise an isolated polynucleotide as disclosed herein.

In one aspect, the present disclosure provides a method of making a humanized TF antibody comprising (i) culturing a cell expressing the humanized antibody; and (b) isolating the humanized antibody from the cultured cell.

In one aspect, the present disclosure provides an antibody-drug conjugate (ADC) of the formula Ab-(L-CA)$_n$, wherein: (i) Ab is a humanized antibody or antigen binding fragment thereof that specifically binds to human tissue factor, said antibody comprising a heavy chain variable region or antigen binding fragment thereof that has at least 90% sequence identity to an amino acid sequence selected from SEQ ID NOs: 9-11 and a light chain variable region or antigen-binding fragment thereof that has at least 90% sequence identity to an amino acid sequence selected from SEQ ID NOs: 12-16; and (ii) (L-CA)$_n$ is a linker-cytotoxic agent moiety, wherein L is a linker, CA is a cytotoxic agent, and n denotes a number from 1 to 8.

In some embodiments, the humanized antibody or antigen-binding fragment thereof does not inhibit tissue factor mediated blood coagulation compared to a normal plasma control.

In some embodiments, the antibody-drug conjugate comprises a humanized tissue factor antibody or antigen-binding fragment comprising a heavy chain variable region or antibody fragment thereof that has at least 95% sequence identity to an amino acid sequence selected from SEQ ID NOs: 9-11.

In some embodiments, the antibody-drug conjugate comprises a humanized tissue factor antibody or antigen-binding fragment thereof comprising a heavy chain variable region or antibody fragment thereof having the amino acid sequence selected from SEQ ID NOs: 9-11.

In some embodiments, the antibody-drug conjugate comprises a humanized tissue factor antibody or antigen-binding fragment thereof comprising a light chain variable region or antigen-binding fragment thereof that has at least 95% sequence identity to an amino acid sequence selected from SEQ ID NOs: 12-16.

In some embodiments, the antibody-drug conjugate comprises a humanized tissue factor antibody or antigen-binding fragment thereof comprising a light chain variable region or antigen-binding fragment thereof having the amino acid sequence selected from SEQ ID NOs: 12-16.

In some embodiments, the antibody-drug conjugate comprises a humanized antibody or antigen binding fragment thereof that binds to human tissue factor comprising a heavy chain variable region or antigen-binding fragment thereof having an amino acid sequence selected from SEQ ID NOs: 9-11 and a light chain variable region or antigen-binding fragment thereof having an amino acid sequence selected from SEQ ID NOs: 12-16.

In some embodiments, the cytotoxic agent in the antibody-drug conjugate is selected from the group consisting of an anti-mitotic agent, a topoisomerase inhibitor, a tubulin inhibitor, an RNA polymerase II inhibitor, a DNA alkylating agent, a DNA damaging agent, and a pyrrolobenzodiazepine. In some embodiments, the cytotoxic agent is selected from the group consisting of a maytansine, a maytansinoid, duocarmycin, camptothecin, an auristatin, an amatoxin, calicheamicin, tubulysin, and derivatives or analogs thereof.

In some embodiments, the cytotoxic agent in the antibody-drug conjugate is a maytansine. In some embodiments, the cytotoxic agent is a maytansinoid. In some embodiments, the cytotoxic agent is an auristatin. In some embodiments, the auristatin is monomethyl auristatin E (MMAE).

In some embodiments, the linker in the antibody-drug conjugate is selected from the group consisting of a hydrophilic linker, a urea linker, a sulfamide linker, and a dicarboxylic acid-based linker. In some embodiments, the linker is a cleavable linker. In some embodiments, the linker is a non-cleavable linker.

In some embodiments, the antibody-drug conjugate has a drug-to-antibody ratio (DAR) of 1 to 8. In some embodiments, the antibody-drug conjugate has a DAR of 4. In some embodiments, the antibody-drug conjugate has a DAR of 2.

In one aspect, the present invention provides a pharmaceutical composition comprising the antibody-drug conjugate and a pharmaceutically acceptable carrier. In some embodiments, the pharmaceutical composition has an average DAR within a range of 1 to 8.

In one aspect, the present invention provides a process for producing an antibody-drug conjugate comprising: (i) linking the linker to the cytotoxic agent; (ii) conjugating the linker-cytotoxic agent moiety to the antibody; and (iii) purifying the antibody-drug conjugate.

In one aspect, the present invention provides a method of treating cancer in a subject in need thereof, comprising administering to a subject in need thereof a therapeutically effective amount of a composition comprising a humanized antibody or antigen-binding fragment thereof, an antibody-drug conjugate, or a pharmaceutical composition.

In some embodiments, the cancer is a solid tumor. In some embodiments, the solid tumor is selected from the group consisting of breast cancer, ovarian cancer, thyroid cancer, colorectal cancer, esophageal cancer, gastric cancer, melanoma, brain cancer, head and neck cancer, epidermal, sarcoma, kidney cancer, pancreatic cancer, prostate cancer, liver cancer, urothelial, and lung cancer.

In some embodiments, the cancer is a hematologic malignancy. In some embodiments, the hematologic malignancy is leukemia, lymphoma, or myeloma. In some embodiments, the hematological malignancy is acute lymphocytic leukemia (ALL), acute myeloid leukemia (AML), chronic lymphocytic leukemia (CLL), small lymphocytic lymphoma (SLL), multiple myeloma (MM), Hodgkin's lymphoma (HL), non-Hodgkin's lymphoma (NHL), mantle cell lymphoma (MCL), follicular lymphoma (FL), Waldenstrom's macroglobulinemia (WM), diffuse large B-cell lymphoma (DLBCL), marginal zone lymphoma (MZL), hairy cell leukemia (HCL), Burkitt's lymphoma (BL), or Richter's transformation. In some embodiments, the hematological malignancy is Hodgkin's lymphoma, non-Hodgkin's lymphoma, acute lymphocytic leukemia (ALL), acute myeloid leukemia (AML), or chronic lymphocytic leukemia (CLL).

In some embodiments, the solid tumor is head and neck cancer. In some embodiments, the liver cancer is hepatocellular carcinoma (HCC). In some embodiments, the lung cancer is non-small cell lung cancer (NSCLC). In some embodiments, the lung cancer is small cell lung cancer (SCLC).

In some embodiments, the cancer overexpresses human tissue factor. In some embodiments, the subject in need thereof is a human subject.

BRIEF DESCRIPTION OF THE FIGURES

Figure 1:
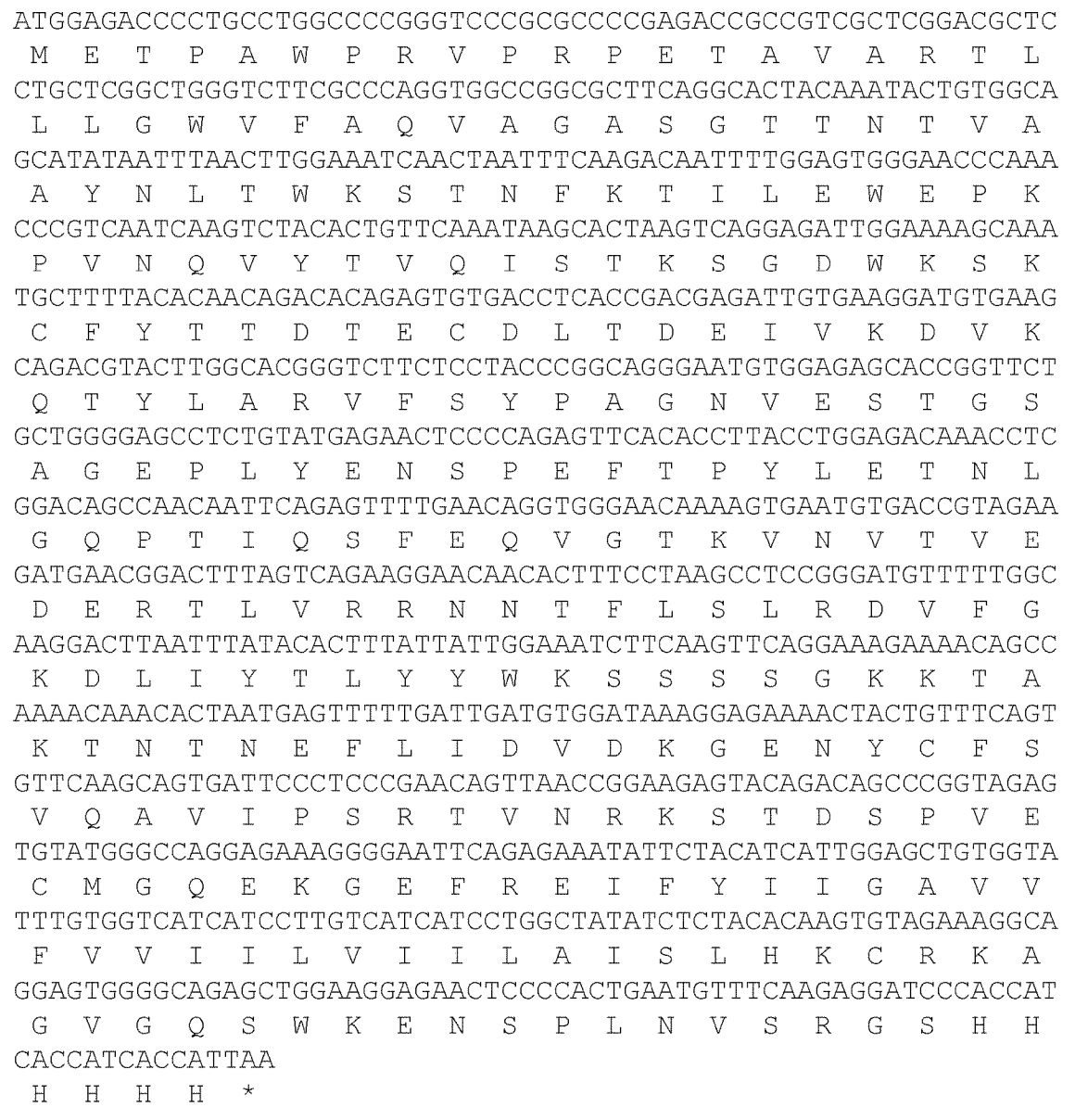

FIG. 1. Nucleotide (SEQ ID NO:1) and amino acid (SEQ ID NO:2) sequences of full length human tissue factor with a 32 amino acid N-terminal leader sequence and a 9 amino acid C-terminal RGS-His$_6$ tag sequence.

FIG. 2. Nucleotide (SEQ ID NO:3) and amino acid (SEQ ID NO:4) sequences of the extracellular domain of human tissue factor with a 32 amino acid N-terminal leader sequence and a 9 amino acid C-terminal RGS-His$_6$ tag sequence.

FIGS. 3A-3B. FIG. 3A. Nucleotide (SEQ ID NO:5) and amino acid (SEQ ID NO:6) sequences of the heavy chain variable region (VH0) of murine antibody TF278. FIG. 3B. Nucleotide (SEQ ID NO:7) and amino acid (SEQ ID NO:8)

sequences of the light chain variable region (VL0) of murine antibody TF278. The six CDR sequences are underlined.

FIGS. 4A-4B. FIG. 4A. Nucleotide (SEQ ID NO:25) and amino acid (SEQ ID NO:9) sequences of the heavy chain variable region (VH6) of humanized tissue factor antibody, known herein as the "B278-LC7HC6 variant." FIG. 4B. Nucleotide (SEQ ID NO:26) and amino acid (SEQ ID NO:12) sequences of the light chain variable region (VL7) of the humanized TF antibody B278-LC7HC6 variant. The six CDR sequences are underlined.

FIGS. 5A-5B. Alignment of light chain (FIG. 5A) and heavy chain (FIG. 5B) variable regions of the disclosed humanized TF antibody B278 variants. VL5, VL6, and VL7 are three variants based on VL3 with various mutations in the framework at key residues. VL8 is a new variant based on a different human subtype, but with physical similarity to the murine VL0. Two additional VH variants, VH5 and VH6, are based on VH4, each having a different set of mutations. The six CDRs are indicated in the boxes.

Figure 6:
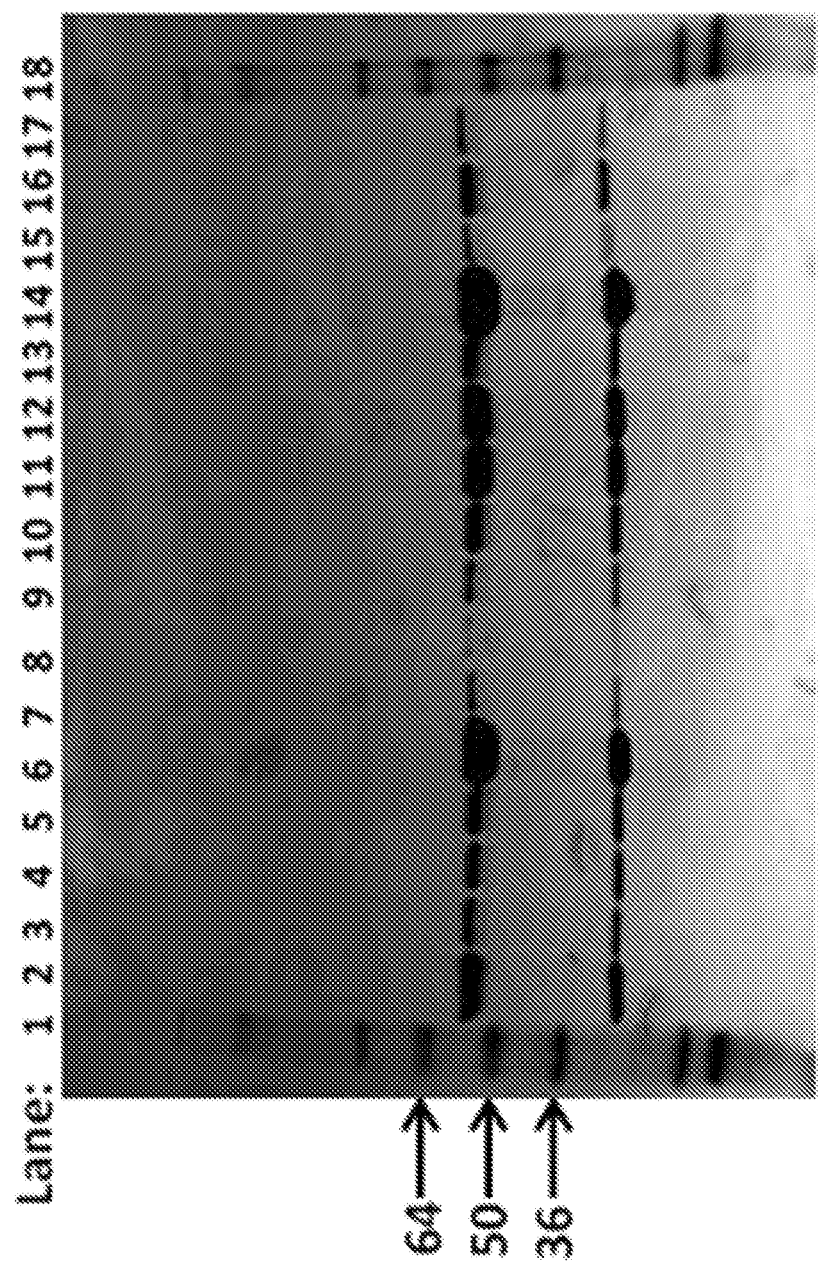

FIG. 6. Reducing SDS-PAGE (4-20% acrylamide gel) analysis of purified humanized B278 antibody variants. Lane 1: SeeBlue plus 2 (Invitrogen, CA), Lane 2: B278-LC3HC5 variant, Lane 3: B278-LC3HC6 variant, Lane 4: B278-LC5HC4 variant, Lane 5: B278-LC5HC5 variant, Lane 6: B278-LC5HC6 variant, Lane 7: B278-LC6HC4 variant #2, Lane 8: B278-LC6HC5 variant, Lane 9: B278-LC6HC6 variant, Lane 10: B278-LC7HC4 variant, Lane 11: B278-LC7HC4 variant #2, Lane 12: B278-LC7HC5 variant, Lane 13: B278-LC7HC6 variant, Lane 14: B278-LC7HC6 variant #2, Lane 15: B278-LC8HC4 variant #2, Lane 16: B278-LC8HC5 variant Lane 17: B278-LC8HC6 variant, Lane 18: SeeBlue plus 2 (Invitrogen, CA).

Figure 7:
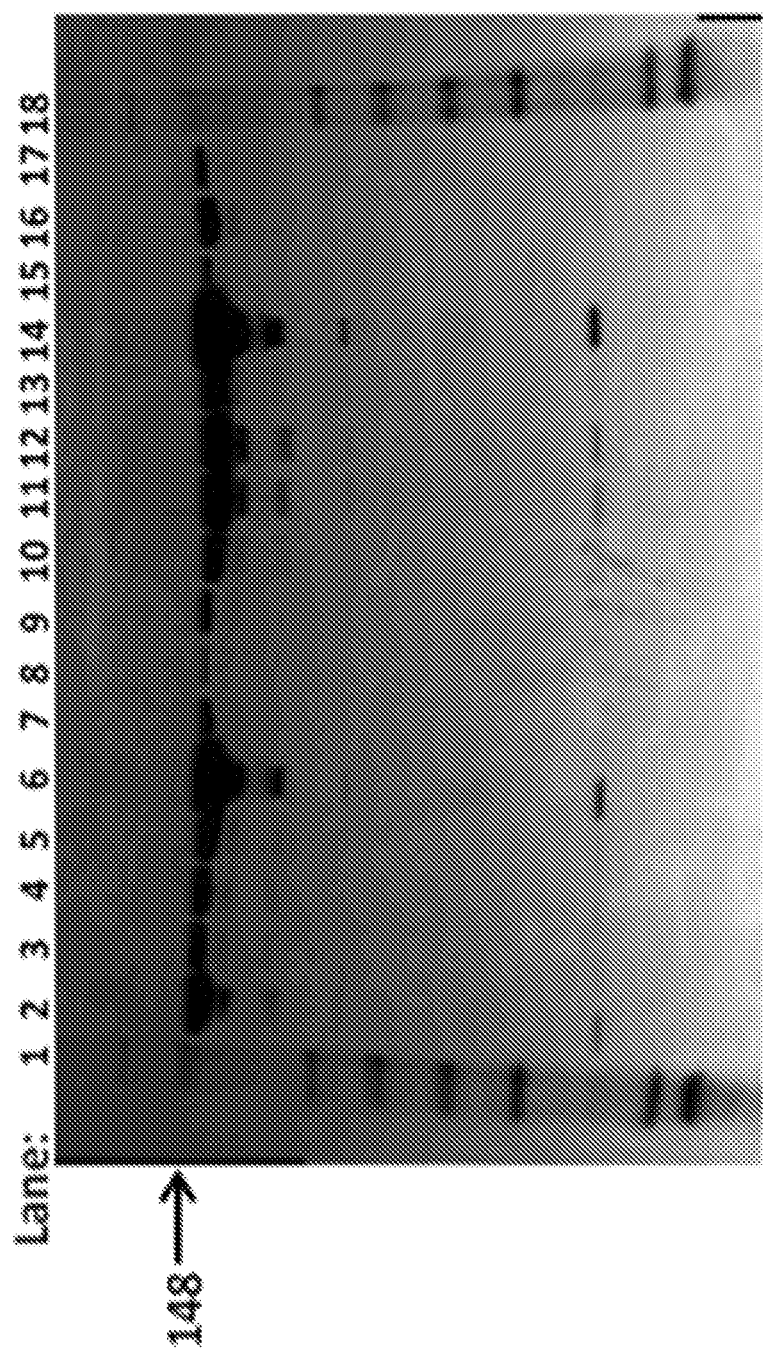

FIG. 7. Non-reducing SDS-PAGE (4-20% acrylamide gel) analysis of purified humanized B278 antibody variants. Lane 1: SeeBlue plus 2 (Invitrogen, CA), Lane 2: B278-LC3HC5 variant, Lane 3: B278-LC3HC6 variant, Lane 4: B278-LC5HC4 variant, Lane 5: B278-LC5HC5 variant, Lane 6: B278-LC5HC6 variant, Lane 7: B278-LC6HC4 variant #2, Lane 8: B278-LC6HC5 variant, Lane 9: B278-LC6HC6 variant, Lane 10: B278-LC7HC4 variant, Lane 11: B278-LC7HC4 variant #2, Lane 12: B278-LC7HC5 variant, Lane 13: B278-LC7HC6 variant, Lane 14: B278-LC7HC6 variant #2, Lane 15: B278-LC8HC4 variant #2, Lane 16: B278-LC8HC5 variant, Lane 17: B278-LC8HC6 variant, Lane 18: SeeBlue plus 2 (Invitrogen, CA).

Figure 8:
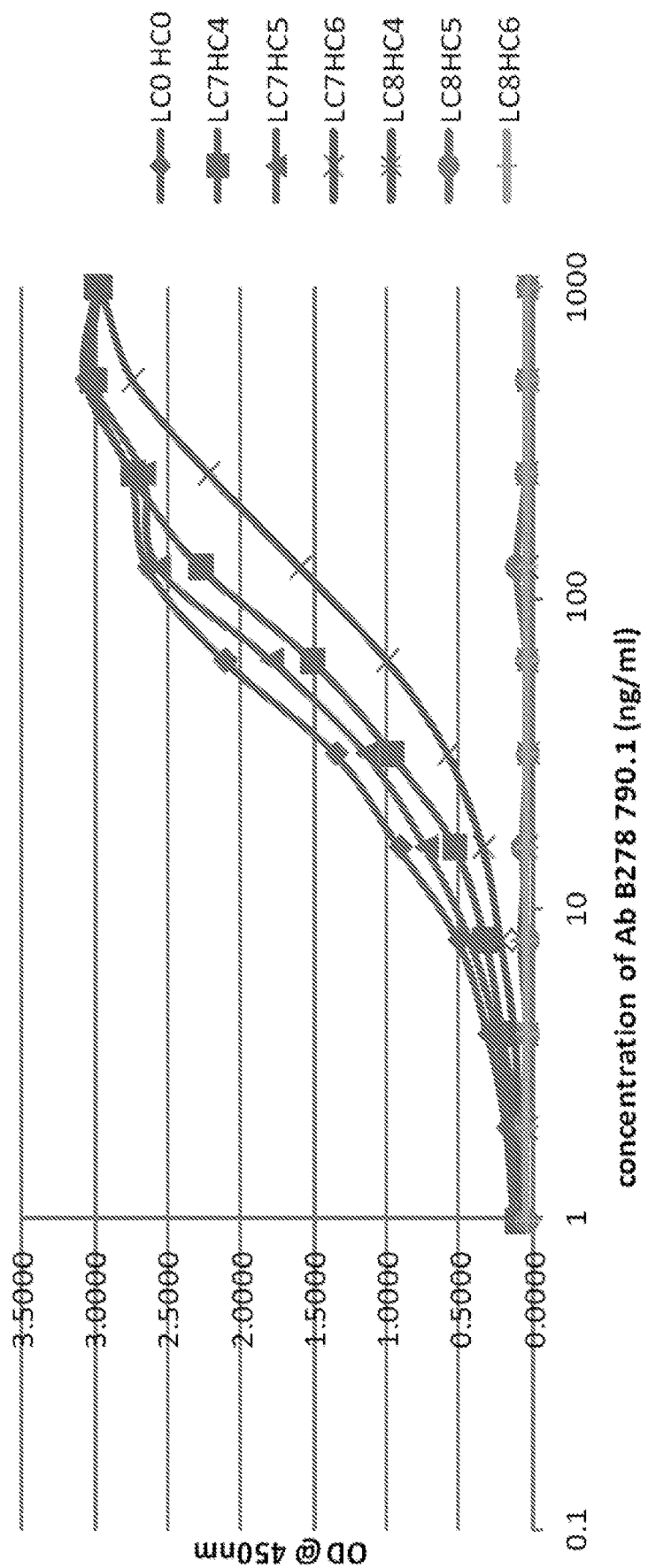

FIG. 8. Binding of the humanized B278 antibody LC7 and LC8 variants and chimeric B278-LC0HC0 to recombinant Human Coagulation Factor III (a.k.a. tissue factor). The chimeric control B278-LC0HC0 contains murine variable regions and human constant regions.

Figure 9A:
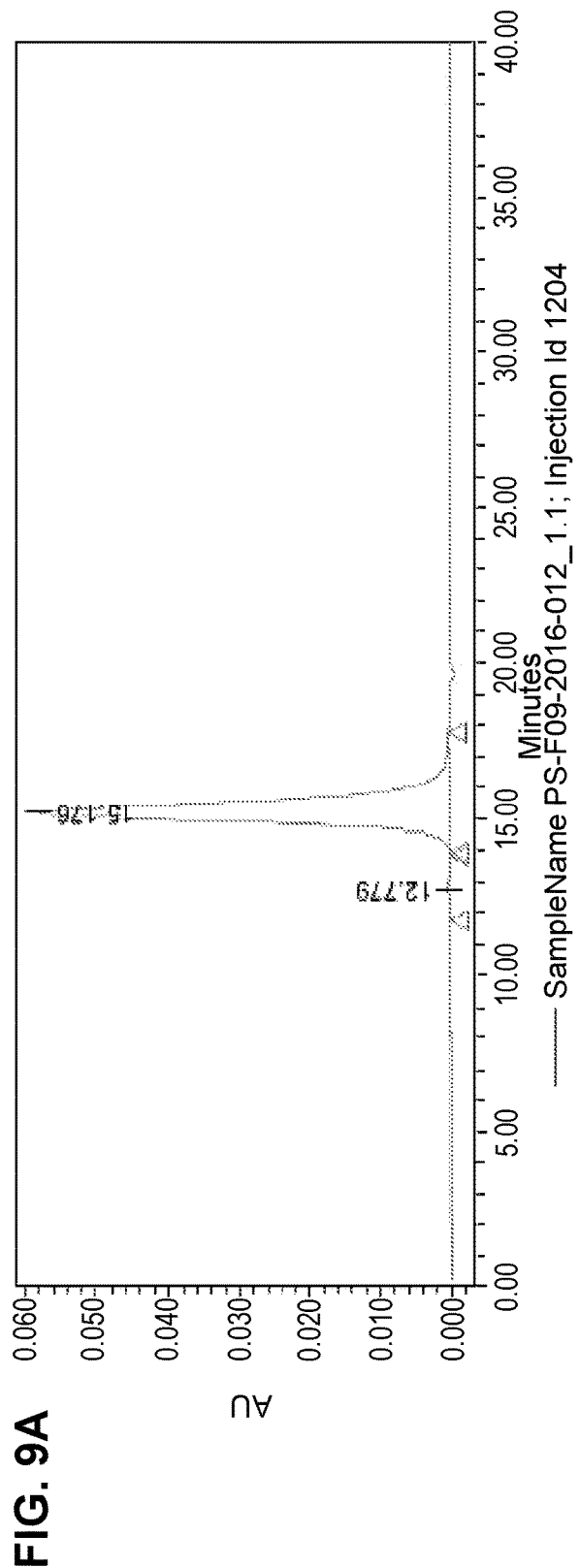
Figure 9B:
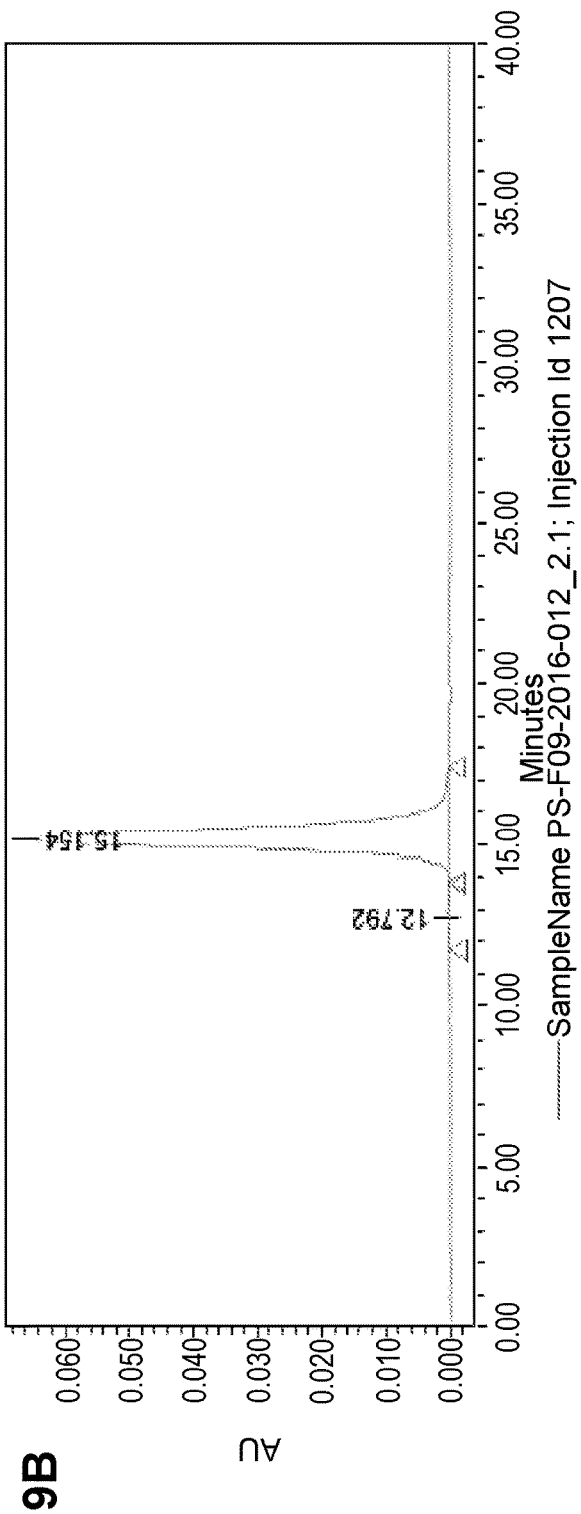

FIGS. 9A-9B. UV chromatograms (λ=280 nm) of both replicates of sample B278-LC7HC6 variant (sample name: PS-F09-2016-012) from Size Exclusion Chromatography (SEC) analysis.

Figure 10A:
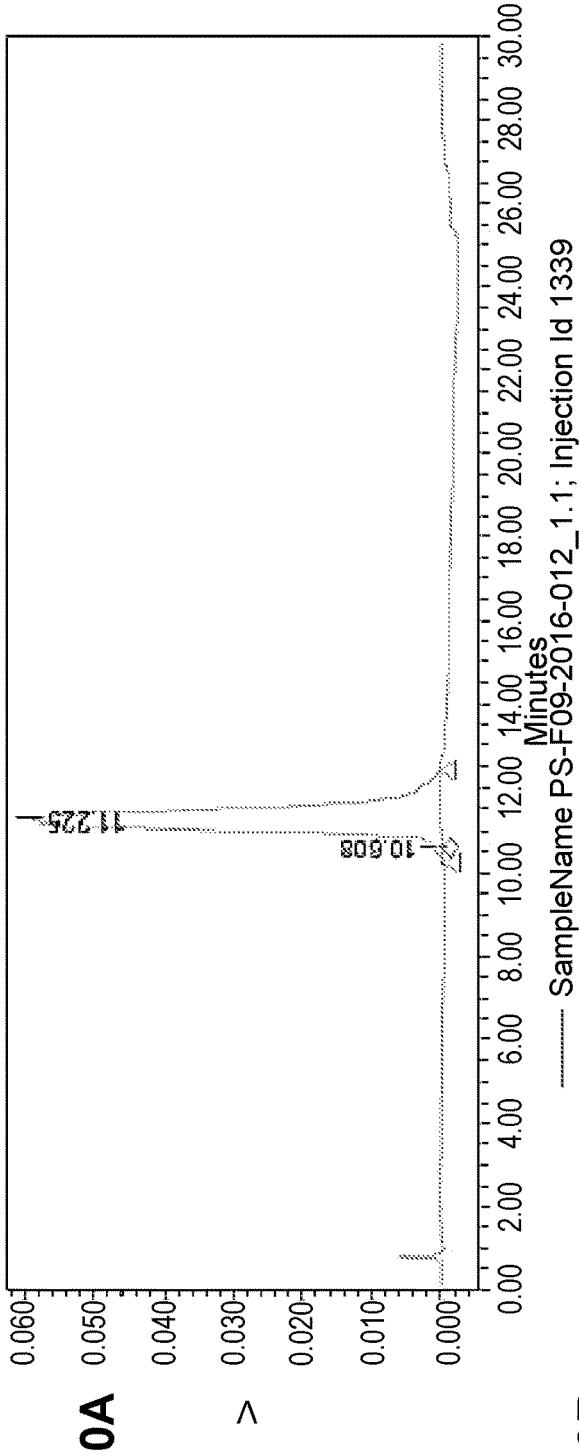
Figure 10B:
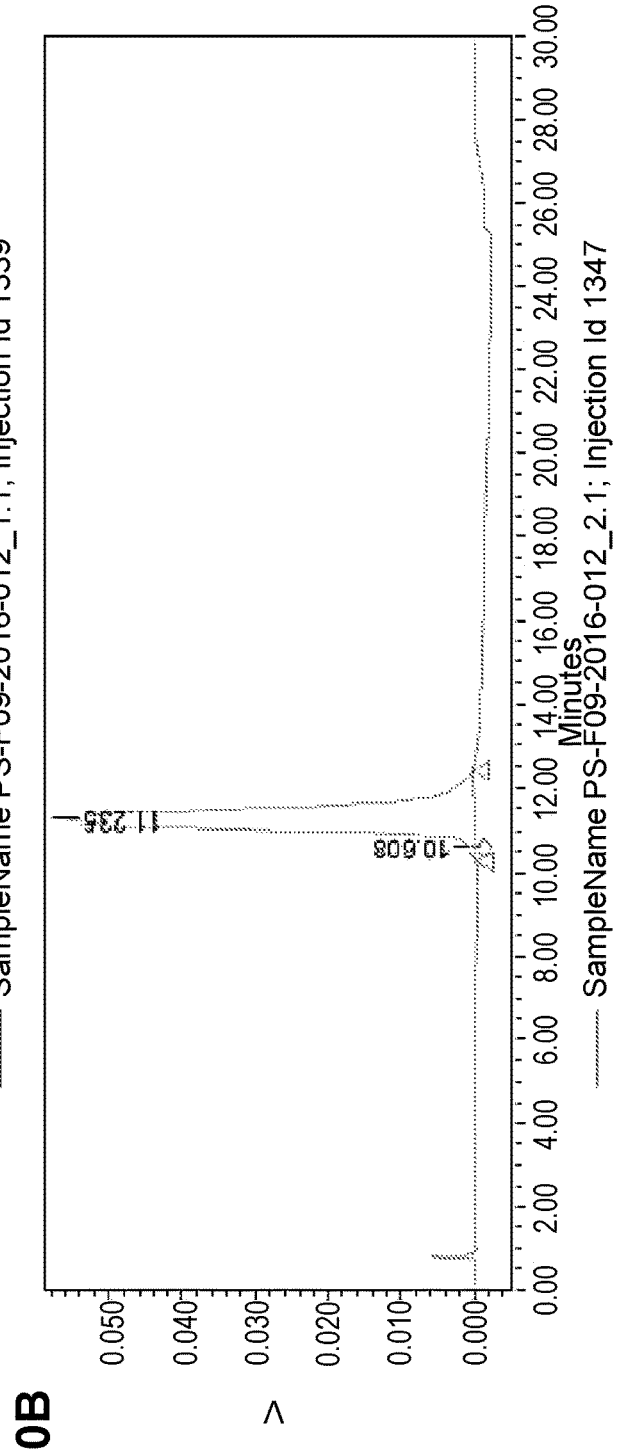

FIGS. 10A-10B. UV chromatograms (λ=280 nm) of both replicates of sample B278-LC7HC6 variant (PS-F09-2016-012) from Hydrophobic Interaction Chromatography (HIC) analysis.

Figure 11A:
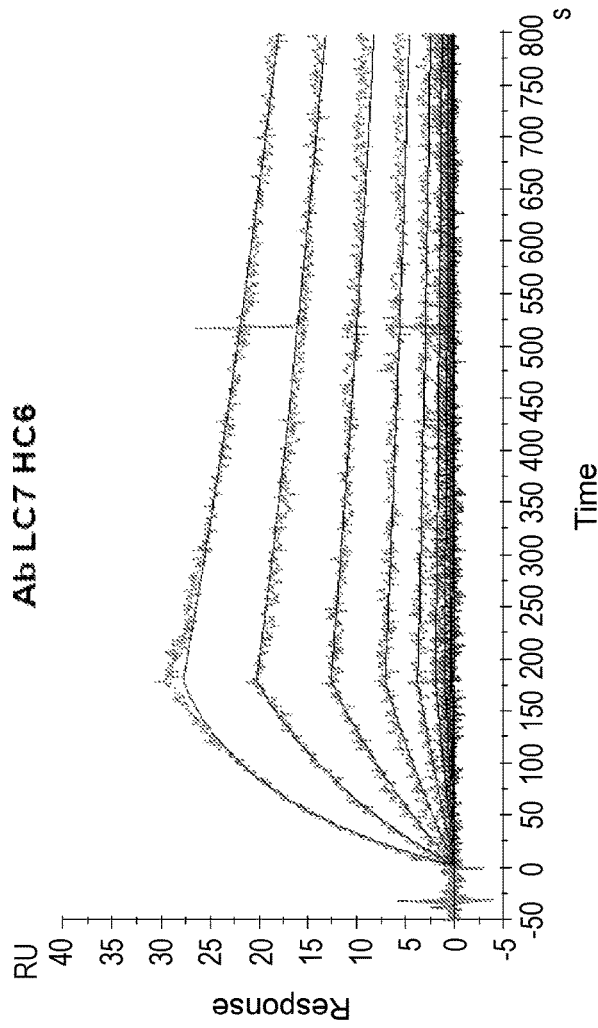
Figure 11B:
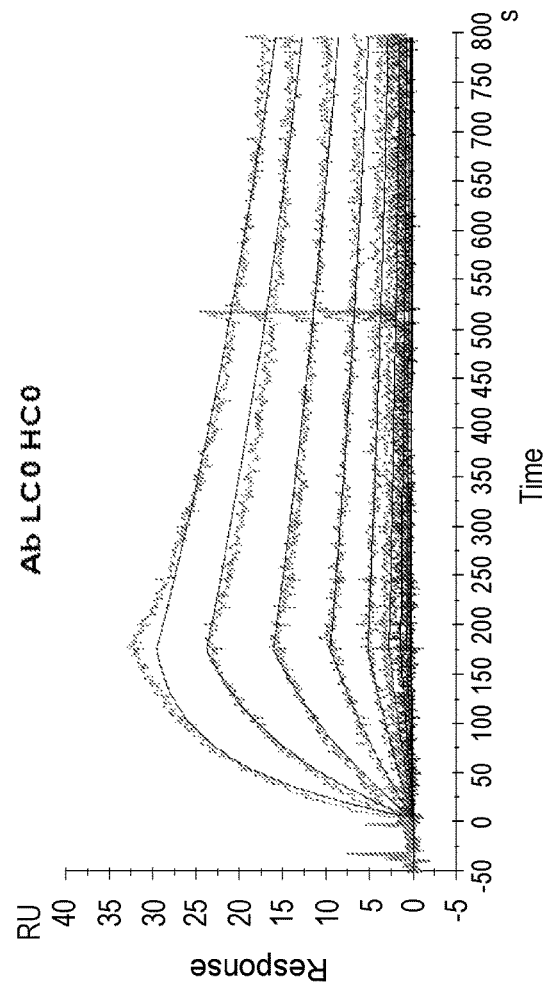

FIGS. 11A-11B. Biacore™/SPR binding analyses of humanized B278-LC7HC6 variant (FIG. 11A) and chimeric control B278-LC0HC0 (FIG. 11B) to assess the binding affinity and on- and off-rates.

Figure 12:
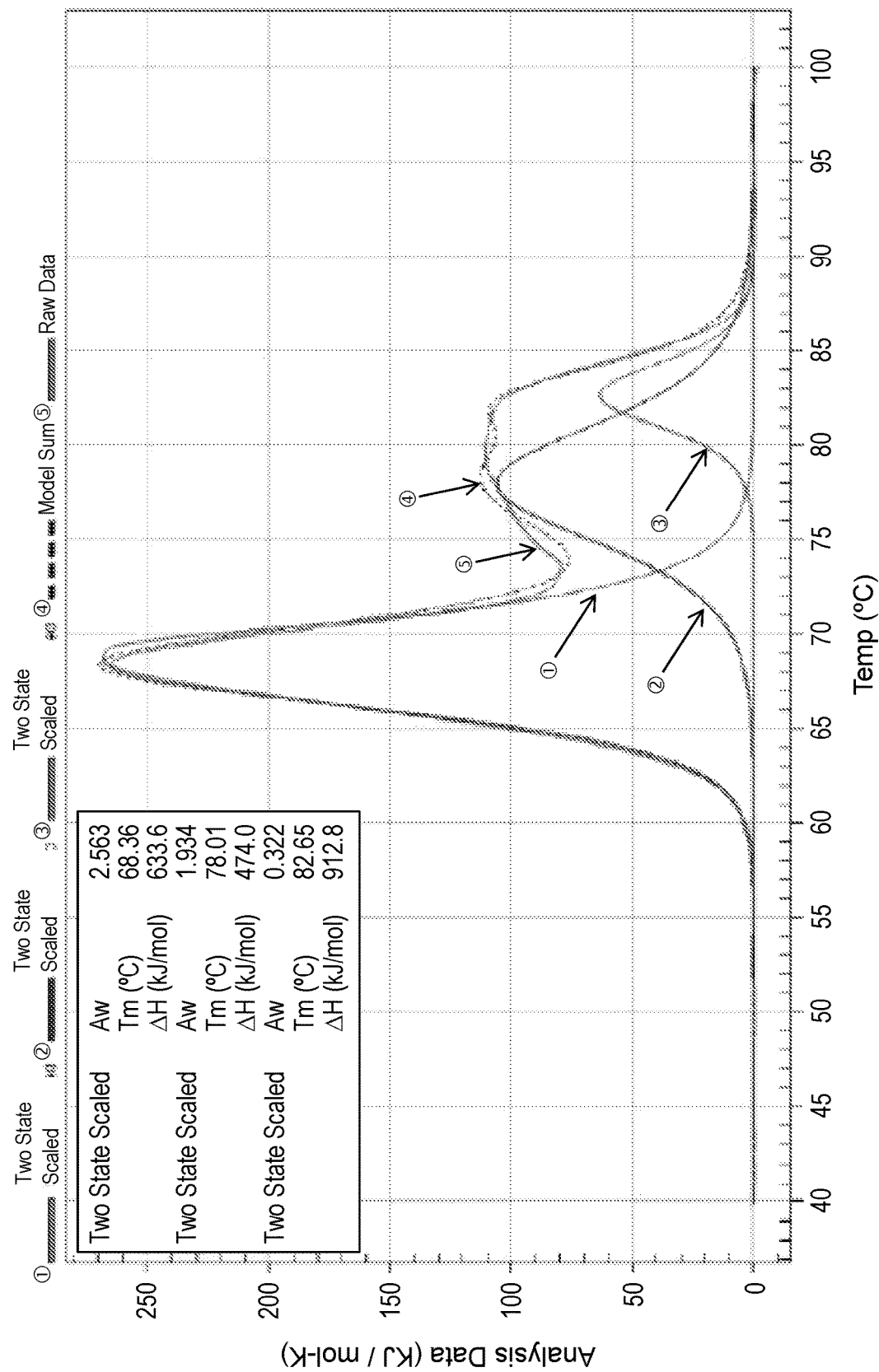

FIG. 12. Exemplary nano-DSC thermogram (first replicate) and fitting of sample B278-LC7HC6. The line indicated by number 5 represents the recorded data and the line indicated by number 4 represents the fit result. The individual transitions identified are shown in lines indicated by numbers 1, 2, and 3.

Figure 13:
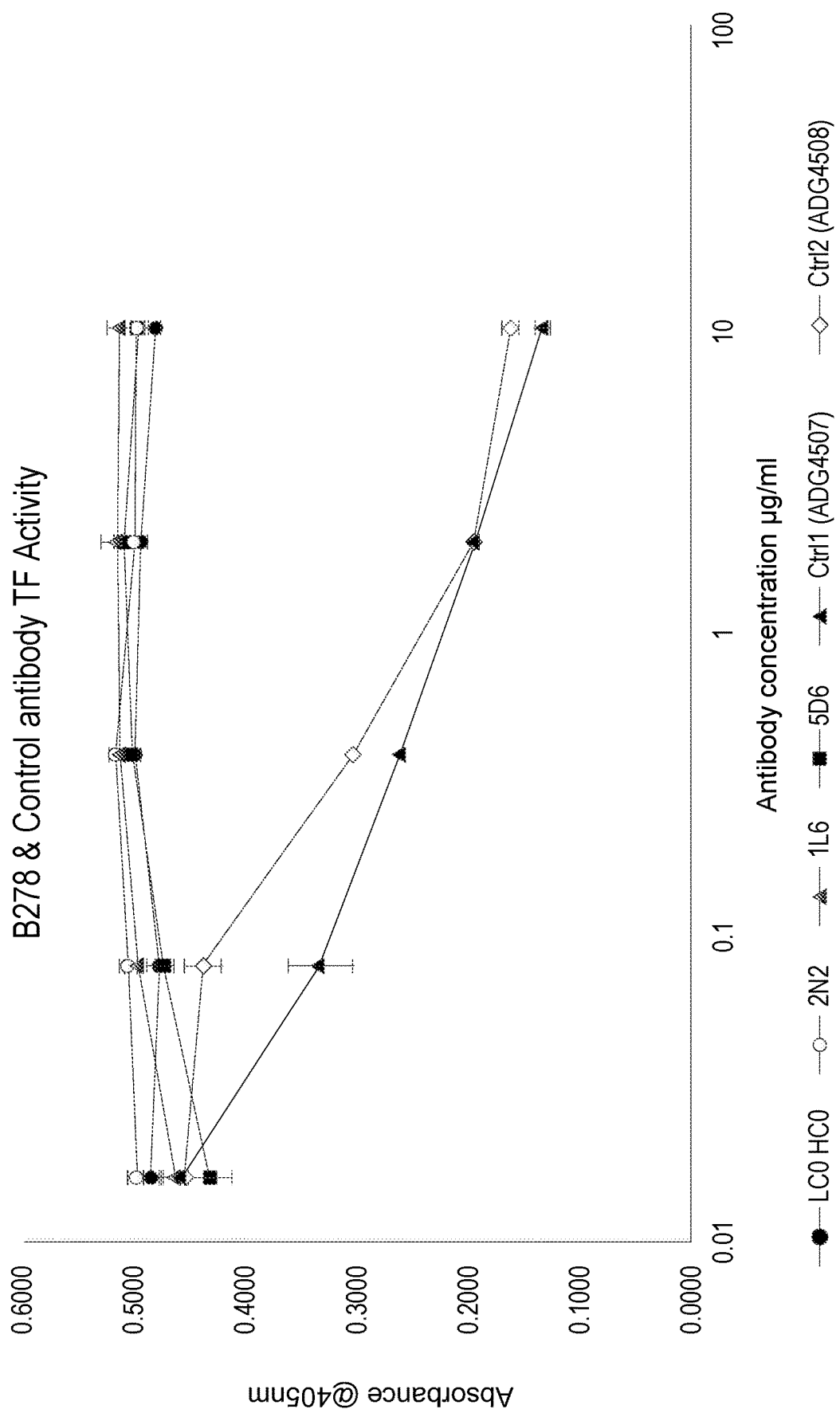

FIG. 13. Inhibition of tissue factor mediated blood coagulation by the humanized TF antibody B278-LC7HC6 variant. 2N2, 1L6, and 5D6 are subclones of the humanized B278-LC7HC6 variant-expressing CHO cell line, selected for optimal expression levels of the humanized LC7HC6 antibody. Ctrl 1 (ADG4507, Sekisui Diagnostics, MA) and Ctrl 2 (ADG4508, Sekisui Diagnostics, MA) are control antibodies known to inhibit tissue factor mediated activation of the blood coagulation cascade. LC0HC0 is the chimeric form of B278.

DETAILED DESCRIPTION OF THE PREFERRED EMBODIMENTS

Definitions

To facilitate an understanding of the present disclosure, a number of terms and phrases are defined below. Additional definitions are set forth throughout the detailed description.

As used herein, the term "human tissue factor" (interchangeably called "TF" or "hTF" herein) refers to any native human tissue factor or any splice variants, allelic variants, isoforms, and species homologs thereof, which are naturally expressed by cells, or are expressed by cells transfected with the human tissue factor gene. hTF may have the protein sequence in NCBI Reference Sequence: NP_001984 (isoform 1) or NCBI Reference Sequence: NP_001171567.1 (isoform 2). Human tissue factor is also known in the art as thromboplastin, coagulation factor III, or CD142. The term "hTF" encompasses "full-length" unprocessed hTF, as well as any form of hTF that results from processing in the cell. The hTF polypeptides described herein can be isolated from a variety of sources, such as from human tissue types or from another source, or prepared by recombinant or synthetic methods.

As used herein, the term "antibody" or "Ab" means an immunoglobulin molecule (or antigen-binding fragment thereof) that recognizes and specifically binds to a target (such as a protein, polypeptide, carbohydrate, polynucleotide, lipid, or combinations thereof) through at least one antigen binding site within the variable region of the immunoglobulin molecule. As used herein, the term "antibody" encompasses intact monoclonal antibodies, intact polyclonal antibodies, bi- or multi-specific antibodies generated from at least two intact antibodies, human antibodies, humanized antibodies, chimeric antibodies, modified antibodies, single chain antibodies, single-chain Fvs (scFv), disulfide-linked Fvs (dsFv), antibody fragments (such as Fab, F(ab'), F(ab')$_2$, and Fv fragments, fragments produced by a Fab expression library, and fragments comprising either a VL or VH domain), anti-idiotypic (anti-Id) antibodies (including, e.g., anti-Id antibodies to the TF antibodies disclosed herein), intracellularly-made antibodies (i.e., intrabodies), and antigen-binding antibody fragments.

The antibodies described herein can be of any of the five major classes of immunoglobulins (i.e., IgA, IgD, IgE, IgG, and IgM), or subclasses (isotypes) thereof (i.e., IgG1, IgG2, IgG3, IgG4, IgA1, and IgA2), based on the identity of their heavy-chain constant domains referred to as alpha, delta, epsilon, gamma, and mu, respectively. In some embodiments, the immunoglobulin is an IgG1 isotype. In some embodiments, the immunoglobulin is an IgG2 isotype. In some embodiments, the immunoglobulin is an IgG4 isotype. The different classes of immunoglobulins have different and well-known subunit structures and three-dimensional configurations. The antibodies described herein can be unmodified or conjugated to other molecules such as toxins, radioisotopes, etc.

The term "anti-TF antibody" or "an antibody that binds to TF" refers to an antibody that is capable of binding tissue factor with sufficient affinity such that the antibody is useful as a diagnostic and/or therapeutic agent in targeting human tissue factor. The extent of binding of an anti-TF antibody to an unrelated, non-hTF protein can be less than about 10% of the binding of the antibody to hTF as measured, e.g., by a radioimmunoassay (MA). In certain embodiments, an antibody that binds to hTF has a dissociation constant ($K_d$) of ≤1 µM, ≤100 nM, ≤10 nM, ≤1 nM, or ≤0.1 nM.

The term "antibody fragment" refers to a portion of an intact antibody which comprises the antigenic determining variable regions of an intact antibody. Examples of antibody fragments include, but are not limited to Fab, Fab', F(ab')2, and Fv fragments, linear antibodies, single chain antibodies, and multispecific antibodies formed from antibody fragments.

As used herein, the term "monoclonal antibody" is intended to be used as in the art, and refers to an antibody obtained from a population of substantially homogenous antibodies that bind to the same antigenic determinants (epitope). "Substantially homogeneous" means that the individual antibodies are identical except for possibly naturally-occurring mutations that may be present in minor amounts. This is in contrast to polyclonal antibodies that typically include different antibodies directed against various, different antigenic determinants (epitopes). The term "monoclonal antibody" encompasses both intact and full-length monoclonal antibodies, as well as antibody fragments (such as Fab, Fab', F(ab')2, Fv), single chain (scFv) mutants, fusion proteins comprising an antibody portion, and any other modified immunoglobulin molecule comprising an antigen recognition site. "Monoclonal antibodies" and antigen-binding fragments thereof are made in any number of manners including, but not limited to, by hybridoma, phage selection, recombinant expression, and transgenic animals.

As used herein, the term "humanized antibody" refers to forms of non-human (e.g. murine) antibodies that are specific immunoglobulin chains, chimeric immunoglobulins, or fragments thereof that contain minimal non-human (e.g., murine) sequences. Typically, humanized antibodies or antigen-binding fragments thereof are human immunoglobulins in which residues from the human complementarity determining region (CDR) are replaced by residues from the CDR of a non-human species (e.g., mouse, rat, rabbit, and hamster, etc.) that have the desired specificity, affinity, and functionality (Jones et al., *Nature* 321:522-525 (1986); Riechmann et al., *Nature* 332:323-327 (1988); Verhoeyen et al., *Science* 239:1534-1536 (1988)). In some instances, the Fv framework region (FR) residues of a human immunoglobulin are replaced with the corresponding residues in an antibody from a non-human species that has the desired specificity, affinity, and capability. The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically, two or three variable domains containing all or substantially all of the CDR regions that correspond to the non-human immunoglobulin whereas all or substantially all of the FR residues are those of a human immunoglobulin consensus sequence. The humanized antibody or antigen-binding fragment thereof can also comprise at least a portion of an immunoglobulin constant region or domain (Fc), typically that of a human immunoglobulin. Non-limiting examples of methods used to generate humanized antibodies are described in U.S. Pat. No. 5,225,539; Roguska et al., *Proc. Natl. Acad. Sci., USA* 91:969-973 (1994); and Roguska et al., *Protein Eng.* 9:895-904 (1996). In some embodiments, a "humanized antibody" is a resurfaced antibody.

A "variable region" of an antibody refers to the variable region of the antibody light chain or the variable region of the antibody heavy chain, either alone or in combination. The variable regions of the heavy and light chain each consist of four relatively conserved framework regions (FR) connected by three complementarity determining regions (CDRs), also known as hypervariable regions. The CDRs in each chain are held together in close proximity by the FRs and, with the CDRs from the other chain, contribute to the formation of the antigen-binding site of the antibody.

There are at least two techniques for determining CDRs: (1) an approach based on cross-species sequence variability (i.e., Kabat et al., Sequences of Proteins of Immunological Interest, 5$^{th}$ ed., National Institutes of Health, Bethesda, Md. (1991)); and (2) an approach based on crystallographic studies of antigen-antibody complexes (Al-lazikani et al., *J. Molec. Biol.* 273:927-948 (1997)). In addition, combinations of these two approaches are sometimes used in the art to determine CDRs. The Kabat numbering system is generally used when referring to a residue in the variable domain (approximately residues 1-107 of the light chain and residues 1-113 of the heavy chain) (e.g., Kabat et al., Sequences of Immunological Interest, 5$^{th}$ ed., National Institutes of Health, Bethesda, Md. (1991)).

The amino acid position numbering as in Kabat, refers to the numbering system used for heavy chain variable domains or light chain variable domains of the compilation of antibodies in Kabat et al., Sequences of Proteins of Immunological Interest, 5$^{th}$ ed., Public Health Service, National Institutes of Health, Bethesda, Md. (1991). Using this numbering system, the actual linear amino acid sequence can contain fewer or additional amino acids corresponding to a shortening of, or insertion into, respectively, a FR or CDR of the variable domain. For example, a heavy chain variable domain can include a single amino acid insert (e.g., residue 52a according to Kabat) after residue 52 of H2 and inserted residues (e.g., residues 82a, 82b, and 82c, etc. according to Kabat) after heavy chain FR residue 82. The Kabat numbering of residues can be determined for a given antibody by alignment at regions of homology of the sequence of the antibody with a "standard" Kabat numbered sequence.

Chothia refers instead to the location of the structural loops (Chothia and Lesk, *J. Mol. Biol.* 196:901-917 (1987)). The end of the Chothia CDR-H1 loop, when numbered using the Kabat numbering convention, varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

| Loop | Kabat | AbM | Chothia |
|------|-------|-----|---------|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 . . . 34 |
| | | (Kabat Numbering) | |
| H1 | H31-H35 | H26-H35 | H26-H32 |
| | | (Chothia Numbering) | |
| H2 | H50-H65 | H50-H58 | H52-H56 |
| H3 | H95-H102 | H95-H102 | H95-H102 |

As used herein, the term "humanized tissue factor antibodies" refers to humanized antibodies (defined above) that are capable of specifically binding to human tissue factor, without inhibiting TF-mediated blood coagulation compared to a normal plasma control. Generally, the humanized tissue factor antibodies described herein are capable of binding tissue factor with sufficient affinity such that the antibody is useful as a diagnostic and/or therapeutic agent in targeting human tissue factor. The extent of binding of an anti-hTF antibody as disclosed herein to an unrelated, non-hTF protein can be less than about 10% of the binding of the antibody to hTF as measured, e.g., by a radioimmunoassay (MA). In certain embodiments, an antibody that binds to hTF has a dissociation constant (Kd) of ≤1 µM, ≤100 nM, ≤10 nM, ≤1 nM, or ≤0.1 nM. See also "binding affinity" below.

The humanized tissue factor antibodies disclosed herein can comprise the variable region(s) alone or in combination with the entirety or a portion of the hinge region, CH1, CH2, CH3, and/or Fc domain(s).

As used herein, the term "human antibody" means an antibody produced by a human or an antibody having an amino acid sequence corresponding to an antibody produced by a human, prepared using any technique known in the art. This definition of a human antibody includes intact (or full-length) antibodies, and fragments thereof.

As used herein, the term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g. mouse, rat, rabbit, etc.) with the desired specificity, affinity, and capability, while the constant regions are homologous to the sequences in antibodies derived from another species (usually human) to reduce the chance of eliciting an immune response in that species.

As used herein, the term "modified antibody" refers to an antibody that has been modified with respect to effector function, so as to enhance the effectiveness of the antibody at mediating antibody-dependent cellular cytotoxicity (ADCC) and/or complement-dependent cytotoxicity (CDC) (also known as complement-mediated cell killing). For example, cysteine residue(s) can be introduced in the Fc region, thereby allowing interchain disulfide bond formation in this region. The homodimeric antibody thus generated can have improved internalization capability and/or increased ADCC and CDC. See Caron et al., *J. Exp. Med.* 176:1191-1195 (1992) and Shopes, B., *J. Immunol.* 148: 2918-2922 (1992). Homodimeric antibodies with enhanced anti-tumor activity can also be prepared using heterobifunctional cross-linkers as described in Wolff et al., *Cancer Research* 53: 2560-2565 (1993). Alternatively, an antibody can be modified such that it has dual Fc regions and can thereby have enhanced complement-mediated lysis and ADCC capabilities. See Stevenson et al., *Anti-Cancer Drug Design* 3:219-230 (1989). Additionally, an antibody can be engineered to produce glycoforms, which have altered glycosylation patterns that result in enhanced ADCC activity. See U.S. Pat. No. 6,602,684.

The present disclosure also encompasses bispecific or bifunctional antibodies that specifically recognize a hTF. Bispecific antibodies are antibodies that are capable of specifically recognizing and binding to at least two different epitopes. The different epitopes can either be within the same molecule (e.g., the same hTF) or on different molecules, such that, for example, the antibodies can specifically recognize and bind a hTF, as well as, for example, a coagulation factor. A bispecific or bifunctional antibody is an artificial hybrid antibody having two different heavy/light chain pairs and two different binding sites. Bispecific antibodies can be produced by a variety of methods including fusion of hybridomas or linking of F(ab') fragments. See, e.g., Songsivilai & Lachmann, *Clin. Exp. Immunol.* 79:315 321 (1990), Kostelny et al., *J. Immunol.* 148:1547-1553 (1992). In addition, bispecific antibodies can be formed as "diabodies" (Holliger et al., *PNAS USA* 90:6444 6448 (1993)) or "Janusins" (Traunecker et al., *EMBO J.* 10:3655 3659 (1991) and Traunecker et al., *Int. J. Cancer Suppl.* 7:51 52 (1992)).

Similarly, a multi-specific antibody is a molecule having binding specificities for at least two different antigens. While such molecules normally bind two antigens (i.e., bispecific antibodies), antibodies with additional specificities, such as trispecific antibodies are also encompassed by the present disclosure.

The terms "epitope" and "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences.

In some embodiments, the sequence alignment algorithm is the algorithm described in Karlin et al., *Proc. Natl. Acad. Sci.* 87:2264-2268 (1990), as modified in Karlin et al., *Proc. Natl. Acad. Sci.* 90:5873-5877 (1993), and incorporated into the NBLAST and)(BLAST programs (Altschul et al., *Nucleic Acids Res.* 25:3389-3402 (1991). In some embodiments, gapped BLAST is used, as described in Altschul et al., *Nucleic Acids Res.* 25:3389-3402 (1997). BLAST-2, WU-BLAST-2 (Altschul et al., *Methods in Enzymology* 266:460-480 (1996), ALIGN, ALIGN-2 (Genentech, South San Francisco, Calif.) or Megalign (DNASTAR) are additional publicly available software programs that can be used to align sequences.

In some embodiments, the percent identity between two nucleotide sequences is determined using the GAP program in GCG software (e.g., using a NWSgapdna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (*J. Mol. Biol.* 48:444-453 (1970)) can be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (*CABIOS* 4:11-17 (1989)). For example, the percent identity can be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain embodiments, the default parameters of the alignment software are used. In certain embodiments, the percentage identity "X" of a first amino acid sequence to a second amino acid sequence is calculated as 100×(Y/Z), where Y is the number of amino acid residues scored as identical matches in the alignment of the first and second sequences (as aligned by visual inspection or a particular sequence alignment program) and Z is the total number of residues in the second sequence.

In some embodiments, whether any particular polynucleotide has a certain percentage sequence identity (e.g., is at least 80% identical, at least 85% identical, at least 90% identical, and in some embodiments, at least 95%, 96%, 97%, 98%, or 99% identical) to a reference sequence can be determined using the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2: 482-489 (1981), to find the best segment of homology between two sequences. When using Bestfit (or any other sequence alignment program to determine whether a particular sequence is, for instance, 95% identical to a reference sequence according to the present disclosure), the parameters are set such that the percentage of identity is calculated over the full length of the reference nucleotide sequence and that gaps in homology of up to 5% of the total number of nucleotides in the reference sequence are allowed.

In some embodiments, two nucleic acids or polypeptides of the invention are "substantially identical," meaning they have at least 70%, at least 75%, at least 80%, at least 85%, at least 90%, and in some embodiments, at least 95%, 96%, 97%, 98%, 99% nucleotide or amino acid residue identity, when compared and aligned for maximum correspondence, as measured using a sequence comparison algorithm, such as Bestfit, or by visual inspection. Identity can exist over a region of the sequences that is at least about 10, about 20, about 40-60 residues in length or any integral value therebetween, and can be over a longer region than 60-80 residues, for example, at least about 90-100 residues, and in some embodiments, the sequences are substantially identical over the full length of the sequences being compared, such as the coding region of a nucleotide sequence for example.

The term "binding affinity" generally refers to the strength of the sum total of noncovalent interactions between a single binding site of a molecule (e.g., an antibody) and its binding partner (e.g., an antigen). Unless indicated otherwise, "binding affinity," as used herein, refers to intrinsic binding affinity which reflects a 1:1 interaction between an antigen and an antibody. The affinity of an antibody for its antigen can generally be represented by the dissociation constant ($K_D$). $K_D$ is the ratio of the rate of disassociation ("off rate" or $k_{off}$, or $k_d$) to the rate of association ("on rate" or $k_{on}$ or $k_a$), and is generally expressed as a molar concentration (M).

Affinity can be measured by common methods known in the art, including those described herein. Low-affinity antibodies generally bind antigen slowly and tend to dissociate readily, whereas high-affinity antibodies generally bind antigen faster and tend to remain bound longer. Alternatively stated, the smaller the $K_D$, the stronger the binding affinity. A variety of methods of measuring binding affinity are known in the art, any of which can be used for purposes of the present disclosure. In some embodiments, the method for determining the $K_D$ of an antibody is by using surface plasmon resonance (SPR), typically using a biosensor system such as a Biacore system. See Example 6, below.

"Or better" when used herein to refer to binding affinity refers to a stronger binding between a molecule and its binding partner. "Or better" when used herein refers to a stronger binding, represented by a smaller numerical $K_D$ value. For example, an antibody that has an affinity for an antigen of "0.6 nM or better," the antibody's affinity for the antigen is represented by a $K_D$ of ≤0.6 nM, i.e., 0.59 nM, 0.58 nM, 0.57 nM etc., or any binding affinity value less than 0.6 nM.

The term "specifically binds" generally means that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

An antibody is said to "competitively inhibit" binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

The phrase "substantially similar," or "substantially the same", as used herein, denotes a sufficiently high degree of similarity between two numeric values (generally one associated with an antibody of the invention and the other associated with a reference/comparator antibody) such that one of skill in the art would consider the difference between the two values to be of little or no biological and/or statistical significance within the context of the biological characteristic measured by said values (e.g., $K_D$ values). The difference between said two values can be less than about 50%, less than about 40%, less than about 30%, less than about 20%, or less than about 10% as a function of the value for the reference/comparator antibody.

A polypeptide, antibody, polynucleotide, vector, or cell that is "isolated" is a polypeptide, antibody, polynucleotide, vector, or cell that is in a form not found in nature. Isolated polypeptides, antibodies, polynucleotides, vectors, or cells include those that have been purified to a degree that they are no longer in a form in which they are found in nature. In some embodiments, a polypeptide, an antibody, polynucleotide, vector, or cell that is isolated is substantially pure.

As used herein, "substantially pure" refers to material which is at least 50% pure (i.e., free from contaminants), at least 90% pure, at least 95% pure, at least 98% pure, or at least 99% pure.

As used herein, the term "antibody-drug conjugate" (ADC), refers to a composition in which at least one compound is linked or conjugated to a humanized tissue factor antibody or antigen-binding fragment thereof, as disclosed herein. The terms antibody-drug conjugate and immunoconjugate are used interchangeably herein. In some embodiments, the compound linked to the humanized tissue factor antibody or antigen-binding fragment thereof is a cytotoxic agent.

As used herein, a "cytotoxic agent" refers to a compound, or drug, that is conjugated to the humanized tissue factor antibody or antigen-binding fragment disclosed herein, that, when administered, results in the death of a cell, induces cell death, or otherwise decreases cell viability. In some embodiments, the cell is a cancer cell or a tumor cell. The cytotoxic agent that is conjugated to the humanized tissue factor antibody described herein is also called the "payload" or "cytotoxic payload."

The cytotoxic agent that can be conjugated to the humanized tissue factor antibody disclosed herein can be selected from various classes of agents. In some embodiments, the cytotoxic agent is a tubulin inhibitor, such as auristatin and maytansinoids. In some embodiments, the cytotoxic agent is a maytansinoid or a maytansinoid analog. In some embodiments, the cytotoxic agent is an RNA polymerase II inhibitor, such as Amanitin. In some embodiments, the cytotoxic agent is a Topoisomerase I inhibitor, such as Camptothecin. In some embodiments, the cytotoxic agent is a DNA alkylating agent, such as Duocarmycin. Other cytotoxic agents are described herein.

As used herein, the terms "linker," "linking group," and "linker sequences" are used interchangeably and refer to any chemical moiety that is capable of linking a compound, such as a cytotoxic agent (e.g., auristatin, amanitin, or a maytansinoid) to a humanized tissue factor antibody, as disclosed herein. Linkers can be susceptible to or substantially resistant to, e.g., disulfide bond cleavage, at conditions under which the compound or the antibody remains active. Linkers can be cleavable or not cleavable. Suitable linkers are known in the art and include, for example, disulfide groups, thioether groups, acid labile groups, photolabile groups, peptide labile groups, and esterase labile groups. In one embodiment, the linker is cleavable.

In some embodiments, the antibody-drug conjugate can contain multiple cytotoxic agents per antibody or antigen-binding fragment thereof and/or multiple linkers per antibody or antigen-binding fragment thereof.

As used in the present disclosure and claims, the singular forms "a," "an," and "the" include plural forms unless the context clearly dictates otherwise.

As used herein, the terms "about" and "approximately," when used to modify a numeric value or numeric range, indicate that deviations of up to 10% above and 5 up to 10% below the value or range remain within the intended meaning of the recited value or range.

The term "and/or" as used in a phrase such as "A and/or B" herein is intended to include both "A and B," "A or B," "A," and "B."

Open terms such as "include," "including," "contain," "containing" and the like mean "comprising." These open-ended transitional phrases are used to introduce an open ended list of elements, method steps, or the like that does not exclude additional, unrecited elements or method steps. Wherever aspects are described herein with the language "comprising," otherwise analogous aspects described in terms of "consisting of" and/or "consisting essentially of" are also provided.

Humanized Tissue Factor Antibodies

The present disclosure provides antibodies, antigen-binding fragments thereof, and antibody-drug conjugates, all of which specifically bind human TF (hTF).

The present disclosure also provides an isolated humanized antibody capable of binding to hTF, wherein the antibody does not inhibit TF-mediated blood coagulation compared to a normal plasma control, and wherein the antibody can initiate one or more Fc-mediated mechanisms. Because the humanized TF antibodies disclosed herein do not inhibit normal TF-mediated blood coagulation, normal plasma clotting is not affected in patients treated with the humanized TF antibodies disclosed herein. In certain embodiments, the humanized TF antibody is isolated.

The full-length nucleotide and amino acid sequences of human tissue factor with a 32 amino acid N terminal leader sequence and a 9 amino acid C-terminal RGS-His6 tag sequence are provided herein as represented by SEQ ID NOs: 1 and 2, respectively.

```
SEQ ID NO: 1: Nucleotide sequence of full
length human tissue factor with a 32 amino
acid N terminal leader sequence and a 9
amino acid C-terminal RGS-His6 tag sequence.
ATGGAGACCCCTGCCTGGCCCCGGGTCCCGCGCCCCGAGACCGCCGTCGC

TCGGACGCTCCTGCTCGGCTGGGTCTTCGCCCAGGTGGCCGGCGCTTCAG

GCACTACAAATACTGTGGCAGCATATAATTTAACTTGGAAATCAACTAAT

TTCAAGACAATTTTGGAGTGGGAACCCAAACCCGTCAATCAAGTCTACAC

TGTTCAAATAAGCACTAAGTCAGGAGATTGGAAAAGCAAATGCTTTTACA

CAACAGACACAGAGTGTGACCTCACCGACGAGATTGTGAAGGATGTGAAG

CAGACGTACTTGGCACGGGTCTTCTCCTACCCGGCAGGGAATGTGGAGAG

CACCGGTTCTGCTGGGGAGCCTCTGTATGAGAACTCCCCAGAGTTCACAC

CTTACCTGGAGACAAACCTCGGACAGCCAACAATTCAGAGTTTTGAACAG

GTGGGAACAAAAGTGAATGTGACCGTAGAAGATGAACGGACTTTAGTCAG

AAGGAACAACACTTTCCTAAGCCTCCGGGATGTTTTTGGCAAGGACTTAA

TTTATACACTTTATTATTGGAAATCTTCAAGTTCAGGAAAGAAAACAGCC

AAAACAAACACTAATGAGTTTTTGATTGATGTGGATAAAGGAGAAAACTA

CTGTTTCAGTGTTCAAGCAGTGATTCCCTCCCGAACAGTTAACCGGAAGA
```

GTACAGACAGCCCGGTAGAGTGTATGGGCCAGGAGAAAGGGGAATTCAGA

GAAATATTCTACATCATTGGAGCTGTGGTATTTGTGGTCATCATCCTTGT

CATCATCCTGGCTATATCTCTACACAAGTGTAGAAAGGCAGGAGTGGGGC

AGAGCTGGAAGGAGAACTCCCCACTGAATGTTTCAAGAGGATCCCACCAT

CACCATCACCATTAA

SEQ ID NO: 2: Amino acid sequence of full
length human tissue factor with a 32 amino
acid N-terminal leader sequence and a 9
amino acid C-terminal RGS-His6 tag sequence.
METPAWPRVPRPETAVARTLLLGWVFAQVAGASGTTNTVAAYNLTWKSTN

FKTILEWEPKPVNQVYTVQISTKSGDWKSKCFYTTDTECDLTDEIVKDVK

QTYLARVFSYPAGNVESTGSAGEPLYENSPEFTPYLETNLGQPTIQSFEQ

VGTKVNVTVEDERTLVRRNNTFLSLRDVFGKDLIYTLYYWKSSSSGKKTA

KTNTNEFLIDVDKGENYCFSVQAVIPSRTVNRKSTDSPVECMGQEKGEFR

EIFYIIGAVVFVVIILVIILAISLHKCRKAGVGQSWKENSPLNVSRGSHH

HHHH

The basic antibody structural unit is known to comprise a tetramer composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxyl-terminal portion of each chain defines a constant region primarily responsible for Fc-mediated mechanisms. Human light chains are classified as kappa and lambda light chains. Heavy chains are classified as mu, delta, gamma, alpha, or epsilon, and define the antibody's isotype as IgM, IgD, IgG, IgA, and IgE, respectively. See generally, *Fundamental Immunology*, Ch. 7 (Paul, W., ed., 2nd ed. Raven Press, N.Y. (1989)). The variable regions of each light/heavy chain pair form the antigen binding site. Thus, an intact IgG antibody has two binding sites. Except in bifunctional or bispecific antibodies, the two binding sites are the same.

The humanized TF antibodies disclosed herein are derived from a murine parent antibody TF278 disclosed in U.S. Pat. No. 7,993,644, which is incorporated herein by reference in its entirety. The nucleotide and amino acid sequences of the heavy chain and light chain variable regions of the murine antibody TF278 are provided as SEQ ID NOs: 5-8, respectively, and shown in FIGS. 3A and 3B.

SEQ ID NO: 5: Nucleotide sequence of the
variable heavy chain domain (VH) of murine
antibody TF278 (VH0):
GAGGTCCAGCTGCAGCAATCTGGAGCTGAGCTGATGAAGCCTGGGGCCTC

AGTGAAGATATCCTGCAAGGCTACTGGCTACACATTCAGTAGCTACTGGA

TAGAGTGGGTAAAGCAGAGGCCTGGACATGGCCTTGAGTGGATTGGAGAG

ATTTTACCTGGAAGTGCTAGTACTAAGTACAATGAGAAGTTCAAGGGCAA

GGCCACATTCACTGCAGATACATCCTCCAACACAGCCTACATGCAACTCA

GCAGCCTGACATCTGAGGACTCTGCCGTCTATTACTGTGCAAGAGATTAT

TACTACGGTAGTAGCTACGGGTTTGCTTACTGGGGCCAAGGGACTCTGGT

CACTGTCTCGAGT

SEQ ID NO: 6: Amino acid sequence of the
variable heavy chain domain (VH) of murine
antibody TF278 (VH0):
EVQLQQSGAELMKPGASVKISCKATGYTFSSYWIEWVKQRPGHGLEWIGE

ILPGSASTKYNEKFKGKATFTADTSSNTAYMQLSSLTSEDSAVYYCARDY

YYGSSYGFAYWGQGTLVTVSS

SEQ ID NO: 7: Nucleotide sequence of the
variable light chain domain (VL) of murine
antibody TF278 (VL0):
CAGGCTGTTGTGACTCAGGAATCTGCACTCACCACATCACCTGGTGAAAC

AGTCACACTCACTTGTCGCTCAAGTACTGGGGCTGTTACAACTAGTAACT

ATGCCAACTGGGTCCAAGAAAAACCAGATCATTTATTCACTGGCCTAATA

GGTGGTACCAACAACCGAGGTCCAGGTGTTCCTGCCAGATTCTCAGGCTC

CCTGATTGGAGACAAGGCTGCCCTCACCATCACAGGGGCACAGACTGAGG

ATGAGGCAGTATATTTCTGTGCTCTATGGTACAGCAACCATTGGGTGTTC

GGTGGAGGAACCAAACTGACTGTCCTAGGT

SEQ ID NO: 8: Amino acid sequence of the
variable light chain domain (VL) of murine
antibody TF278 (VL0):
QAVVTQESALTTSPGETVTLTCRSSTGAVTTSNYANWVQEKPDHLFTGLI

GGTNNRGPGVPARFSGSLIGDKAALTITGAQTEDEAVYFCALWYSNHWVF

GGGTKLTVLG

The humanized TF antibody disclosed herein comprises the heavy chain variable region selected from SEQ ID NOs: 9-11 or the light chain variable region selected from SEQ ID NOs: 12-16. The present disclosure also provides an isolated anti-TF antibody capable of interfering with the binding of the humanized TF antibody disclosed herein to hTF, wherein said anti-TF antibody does not inhibit TF-mediated blood coagulation compared to a normal plasma control.

In some embodiments, the humanized TF antibodies or antigen-binding fragment thereof disclosed herein bind polypeptides having at least about 95%, at least about 90%, at least about 85%, at least about 80%, at least about 75%, at least about 70%, at least about 65%, at least about 60%, at least about 55%, at least about 50%, at least about 45%, or at least about 40% amino acid sequence identity to a human TF polypeptide (e.g., SEQ ID NO:2).

The humanized TF antibodies disclosed herein can bind immunospecifically to a hTF polypeptide or a polypeptide fragment of hTF. In some embodiments, the humanized TF antibodies disclosed herein bind immunospecifically to hTF. In other embodiments, the humanized TF antibodies disclosed herein bind immunospecifically to the extracellular domain of hTF. As used herein, the "extracellular domain of hTF" is intended to refer to the 219 amino acid residue portion of hTF that is localized on the outside surface of the cell (see e.g., FIG. 2, providing the nucleotide (SEQ ID NO:3) and amino acid (SEQ ID NO:4) sequences of the extracellular domain of human tissue factor.

SEQ ID NO: 3: Nucleotide sequence of the
extracellular domain of human tissue factor
with a 32 amino acid N-terminal leader
sequence and a 9 amino acid C-terminal
RGS-His6 tag sequence:
ATGGAGACCCCTGCCTGGCCCCGGGTCCCGCGCCCCGAGACCGCCGTCGC

TCGGACGCTCCTGCTCGGCTGGGTCTTCGCCCAGGTGGCCGGCGCTTCAG

GCACTACAAATACTGTGGCAGCATATAATTTAACTTGGAAATCAACTAAT

TTCAAGACAATTTTGGAGTGGGAACCCAAACCCGTCAATCAAGTCTACAC

TGTTCAAATAAGCACTAAGTCAGGAGATTGGAAAAGCAAATGCTTTTACA

CAACAGACACAGAGTGTGACCTCACCGACGAGATTGTGAAGGATGTGAAG

CAGACGTACTTGGCACGGGTCTTCTCCTACCCGGCAGGGAATGTGGAGAG

CACCGGTTCTGCTGGGGAGCCTCTGTATGAGAACTCCCCAGAGTTCACAC

CTTACCTGGAGACAAACCTCGGACAGCCAACAATTCAGAGTTTTGAACAG

GTGGGAACAAAAGTGAATGTGACCGTAGAAGATGAACGGACTTTAGTCAG

AAGGAACAACACTTTCCTAAGCCTCCGGGATGTTTTTGGCAAGGACTTAA

TTTATACACTTTATTATTGGAAATCTTCAAGTTCAGGAAAGAAAACAGCC

AAAACAAACACTAATGAGTTTTTGATTGATGTGGATAAAGGAGAAAACTA

CTGTTTCAGTGTTCAAGCAGTGATTCCCTCCCGAACAGTTAACCGGAAGA

GTACAGACAGCCCGGTAGAGTGTATGGGCCAGGAGAAAGGGGAATTCAGA

GAAAGAGGATCCCACCATCACCATCACCATTAA

SEQ ID NO: 4: Amino acid sequence of the
extracellular domain of human tissue factor
with a 32 amino acid N-terminal leader
sequence and a 9 amino acid C-terminal
RGS-His6 tag sequence:
METPAWPRVPRPETAVARTLLLGWVFAQVAGASGTTNTVAAYNLTWKSTN

FKTILEWEPKPVNQVYTVQISTKSGDWKSKCFYTTDTECDLTDEIVKDVK

QTYLARVFSYPAGNVESTGSAGEPLYENSPEFTPYLETNLGQPTIQSFEQ

VGTKVNVTVEDERTLVRRNNTFLSLRDVFGKDLIYTLYYWKSSSSGKKTA

KTNTNEFLIDVDKGENYCFSVQAVIPSRTVNRKSTDSPVECMGQEKGEFR

ERGSHHHHHH

In some embodiments, the humanized TF antibodies disclosed herein preferentially bind to hTF. In other embodiments, the humanized TF antibodies disclosed herein immunospecifically bind to hTF and do not cross-react with any other antigens. The humanized TF antibodies disclosed herein do not inhibit TF-mediated blood coagulation compared to a normal plasma control. In some embodiments, the humanized TF antibodies disclosed herein initiate one or more Fc-mediated mechanisms.

As used herein, the term "antigen-binding antibody fragment" (or "antigen-binding fragment") refers to a polypeptide, which is a portion or part of a polypeptide sequence, as compared to a corresponding full-length or native polypeptide sequence of the humanized antibody disclosed herein. The portion or part of a polypeptide sequence can be at least about 10%, at least about 20%, at least about 30%, at least about 40%, at least about 50%, at least about 60%, at least about 70%, at least about 80%, at least about 90%, at least about 95%, or at least about 99% of the full length polypeptide sequence of a full length humanized TF antibody disclosed herein, but which retains at least some degree of binding specificity of the full length antibody, and does not inhibit TF-mediated blood coagulation compared to a normal plasma control. The antigen-binding fragment may also be capable of initiating an Fc-mediated mechanism.

Antigen-binding antibody fragments (including derivatives) of the antibody molecules (e.g., the VH domains and/or VL domains) disclosed herein include, but are not limited to, fragments (including derivatives) having at least 20, at least 40, at least 60, at least 80, at least 100, at least 120, at least 140, at least 160, or more than 160 amino acids of the full-length antibody, and may include the VH domain, VH-CDR1, VH-CDR2, VH-CDR3, VL domain, VL-CDR1, VL-CDR2, and/or VL-CDR3. The resultant antibody or antigen-binding antibody fragments can be screened for biological activity to identify fragments that retain the desired activity (e.g., the ability to bind hTF).

In some embodiments, the humanized TF antibody as disclosed herein comprises a heavy chain variable sequence selected from the SEQ ID NOs:9-11. In some embodiments, the humanized tissue factor antibody comprises a light chain variable sequence selected from the SEQ ID NOs: 12-16. The heavy chain and light chain variable sequences are provided in Tables 1 and 2, respectively.

TABLE 1

Amino acid sequences of heavy chain variable region of humanized variants of TF antibody B278

| Brief description | Sequence (SEQ ID NO) |
|---|---|
| Amino acid sequence of heavy chain variable region VH6 of humanized TF antibody B278 | EVQLQQSGAEVMKPGASVKISCKASGYTFSSYWIEWVKQAPG QGLEWIGEILPGSASTKYNEKFKGRVTFTADTSTNTAYMELS SLRSEDTAVYYCARDYYYGSSYGFAYWGQGTLVTVSS (SEQ ID NO: 9) |
| Amino acid sequence of heavy chain variable region VH4 of humanized TF antibody B278 | QVQLQESGAEVKKPGASVKVSCKASGYTFSSYWIEWVRQAPG QGLEWMGEILPGSASTKYNEKFKGRVTMTRDTSTSTVYMELS SLRSEDTAVYYCARDYYYGSSYGFAYWGQGTLVTVSS (SEQ ID NO: 10) |
| Amino acid sequence of heavy chain variable region VH5 of humanized TF antibody B278 | QVQLQESGAEVKKPGASVKVSCKASGYTFSSYWIEWVRQAPG QGLEWMGEILPGSASTKYNEKFKGRVTMTADTSTNTVYMELS SLRSEDTAVYYCARDYYYGSSYGFAYWGQGTLVTVSS (SEQ ID NO: 11) |

TABLE 2

Amino acid sequences of light chain variable region of humanized variants of TF antibody B278

| Brief description | Sequence (SEQ ID NO) |
|---|---|
| Amino acid sequence light chain variable region VL7 of humanized TF antibody B278 | QAVVTQEPSLTVSPGGTVTLTCRSSTGAVTTSNYANWVQQKP GQLPKGLISGTNNRGPWTTARFSGSILGDKAVLTLWGAHTED EAVYYCALWYSNHWVFGGGTKLTVLG(SEQ ID NO: 12) |
| Amino acid sequence light chain variable region VL3 of humanized TF antibody B278 | QAVVTQEPSLTVSPGGSVTLTCRSSTGAVTTSNYANWIQQKP GQGPKTLISGTNNRGPWTTARFSGSILGDKAVLTLWGAHAED EADYYCALWYSNHWVFGGGTHLTVQG(SEQ ID NO: 13) |
| Amino acid sequence light chain variable region VL5 of humanized TF antibody B278 | QAVVTQEPSLTVSPGGSVTLTCRSSTGAVTTSNYANWVQQKP GQTPTSLISGTNNRGPWTPARFSGSILGDKAVLTLWGAHAED EADYFCALWYSNHWVFGGGTKLTVLG(SEQ ID NO: 14) |
| Amino acid sequence light chain variable region VL6 of humanized TF antibody B278 | QAVVTQEPSLTVSPGGTVTLTCRSSTGAVTTSNYANWVQEKP GHGFKGLISGTNNRGPWTTARFSGSILGDKAVLTLWGAHAED EADYFCALWYSNHWVFGGGTKLTVLG(SEQ ID NO: 15) |
| Amino acid sequence light chain variable region VL8 of humanized TF antibody B278 | QSALIQPPSVSGSPGQSVTISCRSSTGAVTTSNYANWVQQHP GTVPKPMIYGTNNRGPGVPDRFSGSKSGNTASMTISGLQAED EADYFCALWYSNHWVFGGGTKLTVLG(SEQ ID NO: 16) |

In some embodiments, the humanized TF B278 antibody variant comprises heavy chain variable region VH-CDR1, VH-CDR2, and VH-CDR3 sequences. In some embodiments, the humanized TF B278 antibody variant comprises light chain variable region VL-CDR1, VL-CDR2, and VL-CDR3 sequences. The CDR sequences of each of the humanized TF B278 antibody variants disclosed herein are as follows:

VH-CDR1:
(SEQ ID NO: 19)
GYTFSSYWIE

VH-CDR2:
(SEQ ID NO: 20)
EILPGSASTKYNEKFKG

VH-CDR3:
(SEQ ID NO: 21)
ARDYYYGSSYGFAY

VL-CDR1:
(SEQ ID NO: 22)
RSSTGAVTTSNYAN

VL-CDR2:
(SEQ ID NO: 23)
GTNNRGP

VL-CDR3:
(SEQ ID NO: 24)
ALWYSNHWV

By way of a non-limiting example, an antibody can be considered to preferentially bind hTF if it binds the protein with a dissociation constant ($K_D$) or an off rate ($K_{off}$), that is less than the antibody's $K_D$ or $K_{off}$ for a second antigen. In other non-limiting embodiments, an antibody can be considered to bind hTF preferentially if it binds the protein with a $K_D$ or $K_{off}$ that is at least one order of magnitude less than the antibody's $K_D$ or $K_{off}$ for the second antigen. In other non-limiting embodiments, an antibody can be considered to bind hTF preferentially if it binds hTF with a $K_D$ or $K_{off}$ that is at least two orders of magnitude less than the antibody's $K_D$ or $K_{off}$ for the second antigen.

The humanized TF antibodies disclosed herein can also be described in terms of their binding affinity to hTF. In some embodiments, binding affinities include those with a dissociation constant or $K_D$ less than or equal to $5\times10^{-2}$M, $10^{-2}$ M, $5\times10^{-3}$M, $10^{-3}$M, $5\times10^{-4}$M, or $10^{-4}$M. In other embodiments, affinities include those with a dissociation constant or $K_D$ less than or equal to $5\times10^{-5}$M, $10^{-5}$ M, $5\times10^{-6}$M, $10^{-6}$M, $5\times10^{-7}$M, $10^{7}$ M, $5\times10^{-8}$ M or $10^{-8}$M. In yet other embodiments, binding affinities include those with a dissociation constant or $K_D$ less than or equal to $5\times10^{-9}$M, $10^{-9}$M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$M, $5\times10^{-15}$M, or $10^{-15}$ M.

In some embodiments, antibodies of the invention can bind hTF polypeptides with an off rate ($K_{off}$) of less than or equal to $5\times10^{-2}$ sec$^{-1}$, $10^{-2}$ sec$^{-1}$, $5\times10^{-3}$ sec$^{-1}$ or $10^{-3}$ sec$^{-1}$. In other embodiments, antibodies of the invention can bind hTF polypeptides or fragments thereof with an off rate ($K_{off}$) less than or equal to $5\times10^{-4}$ sec$^{-1}$, $10^{-4}$ sec$^{-1}$, $5\times10^{-5}$ sec$^{-1}$, or $10^{-5}$ sec$^{-1}$ $5\times10^{-6}$ sec$^{-1}$, $10^{-6}$ sec$^{-1}$, $5\times10^{-7}$ sec$^{-1}$ or $10^{-7}$ sec$^{-1}$.

In some embodiments of the present disclosure, antibodies that immunospecifically bind to hTF can comprise a polypeptide having the amino acid sequence of any one of the heavy chains expressed by an anti-TF antibody-expressing cell line of the invention and/or any one of the light chains expressed by an anti-TF antibody-expressing cell line of the invention. In other embodiments of the present disclosure, antibodies that immunospecifically bind to hTF can comprise a polypeptide having the amino acid sequence of any one of the VH domains of a heavy chain expressed by an anti-TF antibody-expressing cell line of the invention and/or any one of the VL domains of a light chain expressed by an anti-TF antibody-expressing cell line of the invention. In yet other embodiments, antibodies of the present disclosure can comprise the amino acid sequence of a VH domain and VL domain expressed by a single anti-TF antibody-expressing cell line of the invention. In other embodiments, antibodies of the present disclosure can comprise the amino acid sequence of a VH domain and a VL domain expressed by two different anti-TF antibody-expressing cell lines of the invention. Molecules comprising, or alternatively consisting of, antigen-binding antibody fragments of the VH and/or VL domains expressed by an anti-TF antibody-expressing cell line of the invention that immunospecifically bind to hTF are also encompassed by the invention, as are nucleic acid molecules encoding these VH and VL domains, molecules, and/or fragments.

The present disclosure also provides polypeptides that comprise, or alternatively consist of, variants (including derivatives) of the humanized TF antibody molecules (e.g., the VH domains and/or VL domains) described herein, which polypeptides immunospecifically bind to hTF or a fragment or variant thereof. The term "variant" refers to a molecule (e.g., a polypeptide or polynucleotide sequence) with at least one or more differences in its amino acid or nucleotide sequence as compared to a corresponding native polypeptide or DNA sequence. Amino acid sequence variants of the invention will possess at least about 70%, at least about 75%, at least about 85%, at least about 95%, or at least about 99% sequence identity with the amino acid sequence of a humanized TF antibody, as disclosed herein.

"Substitutional variants" are those that have at least one amino acid residue in a native sequence removed and a different amino acid inserted in its place at the same position. The substitutions can be single, where only one amino acid residue in the molecule has been substituted, or they can be multiple, where two or more amino acid residues have been substituted in the same molecule. "Insertional variants" are those with one or more amino acids inserted immediately adjacent to an amino acid at a particular position in a native amino acid sequence connected to either the α-carboxyl or α-amino functional group of the amino acid. "Deletional variants" are those with one or more amino acid residues removed from the native amino acid sequence. Ordinarily, deletional variants will have one or two amino acids deleted in a particular region of the molecule.

Standard techniques known to those skilled in the art can be used to introduce mutations into a humanized TF antibody, as disclosed herein, including, for example, by site-directed mutagenesis or PCR-mediated mutagenesis of the encoding nucleic acid molecule which results in amino acid substitutions. In some embodiments, the variant (including derivatives) has less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference polypeptide. In some embodiments, the variant polypeptide has the same immunospecificity, or binds to the same epitope, as a polypeptide of the present disclosure.

It is well-known in the art that polypeptides, or fragments or variants thereof, with similar amino acid sequences can have similar structure and many of the same biological activities. Thus, the present disclosure is further directed to an isolated first antibody, or antigen-binding fragment thereof, having an amino acid sequence at least 70%, at least 80%, at least 85%, at least 90%, at least 95%, at least 96%, at least 97%, at least 98%, or at least 99% identical to a second antibody comprising an amino acid sequence selected from the group consisting of: (a) at least one CDR region of a VH domain of the humanized TF antibody as set forth in SEQ ID NOs:19-21; (b) at least two CDR regions of a VH domain of the humanized TF antibody as set forth in SEQ ID NOs: 19-21; (c) at least three CDR regions of a VH domain of the humanized TF antibody as set forth in SEQ ID NOs: 19-21; (d) at least one CDR region of a VL domain of the humanized TF antibody as set forth in SEQ ID NOs:22-24; (e) at least two CDR regions of a VL domain of the humanized TF antibody as set forth in SEQ ID NOs:22-24; and (f) at least three CDR regions of a VL domain of the humanized TF antibody as set forth in SEQ ID NOs:22-24. In some embodiments, the first antibody, or antigen-binding fragment thereof, has the same immunospecificity, or binds the same epitope, as the second antibody.

The present disclosure also provides an isolated humanized TF antibody, or antigen-binding fragment thereof, having an amino acid sequence at least 70%, at least 80%, at least 85%, at least 90%, or at least 95% identical to an amino acid sequence selected from the group consisting of SEQ ID NOs:9-18. In some embodiments, the antibody, or antigen-binding fragment thereof, has the same immunospecificity, or binds the same epitope, as the polypeptide encoded by the amino acid sequence selected from the group consisting of SEQ ID NOs:9-18.

In some embodiments, the humanized tissue factor antibody is the B278-LC3HC4 variant, consisting of the light chain variable region VL3 (SEQ ID NO:13) and the heavy chain variable region VH4 (SEQ ID NO:10).

In some embodiments, the humanized tissue factor antibody is the B278-LC3HC5 variant, consisting of the light chain variable region VL3 (SEQ ID NO:13) and the heavy chain variable region VH5 (SEQ ID NO:11).

In some embodiments, the humanized tissue factor antibody is the B278-LC6HC6 variant, consisting of the light chain variable region VL3 (SEQ ID NO:13) and the heavy chain variable region VH6 (SEQ ID NO:9).

In some embodiments, the humanized tissue factor antibody is the B278-LC5HC4 variant, consisting of the light chain variable region VL5 (SEQ ID NO:14) and the heavy chain variable region VH4 (SEQ ID NO:10).

In some embodiments, the humanized tissue factor antibody is the B278-LC5HC5 variant, consisting of the light chain variable region VL5 (SEQ ID NO:14) and the heavy chain variable region VH5 (SEQ ID NO:11).

In some embodiments, the humanized tissue factor antibody is the B278-LC5HC6 variant, consisting of the light chain variable region VL5 (SEQ ID NO:14) and the heavy chain variable region VH6 (SEQ ID NO:9).

In some embodiments, the humanized tissue factor antibody is the B278-LC6HC4 variant, consisting of the light chain variable region VL6 (SEQ ID NO:15) and the heavy chain variable region VH4 (SEQ ID NO:10).

In some embodiments, the humanized tissue factor antibody is the B278-LC6HC5 variant, consisting of the light chain variable region VL6 (SEQ ID NO:15) and the heavy chain variable region VH5 (SEQ ID NO:11).

In some embodiments, the humanized tissue factor antibody is the B278-LC6HC6 variant, consisting of the light chain variable region VL6 (SEQ ID NO:15) and the heavy chain variable region VH6 (SEQ ID NO:9).

In some embodiments, the humanized tissue factor antibody is the B278-LC7HC4 variant, consisting of the light chain variable region VL7 (SEQ ID NO:12) and the heavy chain variable region VH4 (SEQ ID NO:10).

In some embodiments, the humanized tissue factor antibody is the B278-LC7HC5 variant, consisting of the light chain variable region VL7 (SEQ ID NO:12) and the heavy chain variable region VH5 (SEQ ID NO:11).

In some embodiments, the humanized tissue factor antibody is the B278-LC7HC6 variant, consisting of the light chain variable region VL7 (SEQ ID NO:12) and the heavy chain variable region VH6 (SEQ ID NO:9).

In some embodiments, the humanized tissue factor antibody is the B278-LC8HC4 variant, consisting of the light chain variable region VL8 (SEQ ID NO:16) and the heavy chain variable region VH4 (SEQ ID NO:10).

In some embodiments, the humanized tissue factor antibody is the B278-LC8HC5 variant, consisting of the light chain variable region VL8 (SEQ ID NO:16) and the heavy chain variable region VH5 (SEQ ID NO:11).

In some embodiments, the humanized tissue factor antibody is the B278-LC8HC6 variant, consisting of the light chain variable region VL8 (SEQ ID NO:16) and the heavy chain variable region VH6 (SEQ ID NO:9).

Also provided are polypeptides that comprise: (a) a polypeptide having at least about 90% sequence identity to SEQ ID NOs:9-11 and 17; and/or (b) a polypeptide having at least about 90% sequence identity to SEQ ID NOs:12-16 and 18. In some embodiments, the polypeptide comprises a polypeptide having at least about 95%, at least about 96%, at least about 97%, at least about 98%, or at least about 99% sequence identity to SEQ ID NOs:9-18. Thus, in certain embodiments, the polypeptide comprises (a) a polypeptide having at least about 95% sequence identity to SEQ ID NOs: 9-11 and 17, and/or (b) a polypeptide having at least about 95% sequence identity to SEQ ID NOs: 12-16 and 18. In some embodiments, the polypeptide comprises (a) a polypeptide having the amino acid sequence of SEQ ID NOs: 9-11 and 17; and/or (b) a polypeptide having the amino acid sequence of SEQ ID NOs: 12-16 and 18. In some embodiments, the polypeptide is an antibody and/or the polypeptide specifically binds hTF. In some embodiments, the polypeptide is a humanized antibody that specifically binds hTF. In some embodiments, the polypeptide having a certain percentage of sequence identity to SEQ ID NOs: 9-18 differs from SEQ ID NOs: 9-18 by only conservative amino acid substitutions.

Polypeptides can comprise one of the individual light chains or heavy chains disclosed herein. Antibodies and polypeptides can also comprise both a light chain and a heavy chain as disclosed herein. Exemplary light chain and heavy chain sequences (LC7 and HC6) are provided herein:

```
SEQ ID NO: 17: amino acid sequence of
full length heavy chain HC6:
EVQLQQSGAEVMKPGASVKISCKASGYTFSSYWIEWVKQAPGQGLEWIGE

ILPGSASTKYNEKFKGRVTFTADTSTNTAYMELSSLRSEDTAVYYCARDY

YYGSSYGFAYWGQGTLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSPG

K

SEQ ID NO: 18: amino acid sequence of
full length light chain LC7
QAVVTQEPSLTVSPGGTVTLTCRSSTGAVTTSNYANWVQQKPGQLPKGLI

SGTNNRGPWTTARFSGSILGDKAVLTLWGAHTEDEAVYYCALWYSNHWVF

GGGTKLTVLGQPKAAPSVTLFPPSSEELQANKATLVCLISDFYPGAVTVA

WKADSSPVKAGVETTTPSKQSNNKYAASSYLSLTPEQWKSHRSYSCQVTH

EGSTVEKTVAPTECS
```

The present disclosure also encompasses humanized antibodies that have one or more of the same biological characteristics as one or more of the antibodies described herein. By "biological characteristics" is intended to mean the in vitro or in vivo activities or properties of the humanized antibodies, such as, for example, the ability to specifically bind to TF (e.g., hTF expressed on a cell surface, or membrane-embedded hTF), without inhibiting TF-mediated blood coagulation compared to a normal plasma control, or the ability to bind to the same epitope as one of the TF antibodies disclosed herein. Such epitope binding can be routinely determined using assays known in the art.

The present disclosure is also directed to a humanized TF monoclonal antibody or an antigen-binding fragment thereof having the binding characteristics of, or that competes for binding to an epitope recognized by, a monoclonal antibody produced by a hybridoma cell line TF278 deposited under ATCC Accession No. PTA-5676.

The present disclosure is also directed to a polypeptide or a humanized antibody or an antigen-binding fragment thereof that specifically binds to TF, comprising one or more of the amino acid sequences of SEQ ID NOs:9-26.

Methods of Producing Antibodies

Antibodies and antigen-binding fragments thereof that immunospecifically bind to TF (e.g., human TF) can be produced by any method known in the art for the synthesis of antibodies and antigen-binding fragments thereof, for example, by chemical synthesis or by recombinant expression techniques. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Sambrook J. et al., Molecular Cloning: A Laboratory Manual, Cold Spring Harbor Laboratory Press, Cold Spring Harbor, N.Y. (2001); Ausubel, F. M. et al., Current Protocols in Molecular Biology, John Wiley & Sons (1987 and annual updates); Coligan, J. E. et al., Current Protocols in Immunology, John Wiley & Sons (1987 and annual updates); Gait. M. J. (ed.), Oligonucleotide Synthesis: A Practical Approach, IRL Press (1984); Eckstein, F. (ed.), Oligonucleotides and Analogues: A Practical Approach, IRL Press (1991); Birren, B. et al. (eds.), Genome Analysis: A Laboratory Manual, Cold Spring Harbor Laboratory Press (1999).

In one aspect, provided herein is a method of making an antibody or antigen-binding fragment thereof that immunospecifically binds to TF (e.g., human TF) comprising culturing a cell or host cell described herein. In a certain aspect, provided herein is a method of making an antibody or antigen-binding fragment thereof which immunospecifically binds to TF (e.g., human TF) comprising expressing (e.g., recombinantly expressing) the antibody or antigen-binding fragment thereof using a cell or host cell described herein (e.g., a cell or a host cell comprising one or more polynucleotides encoding an antibody or antigen-binding fragment thereof described herein). In some embodiments, the cell is an isolated cell. In some embodiments, the polynucleotides have been introduced into the cell. In some embodiments, the method further comprises the step of purifying the antibody or antigen-binding fragment thereof obtained from the cell or host cell.

Methods for producing polyclonal antibodies to an antigen of interest are known in the art (see, for example, Ausubel, F. M. et al., eds., Chapter 11 in Short Protocols in Molecular Biology, 5$^{th}$ ed., John Wiley and Sons, New York, (2002)). For example, a polypeptide of interest can be administered to any of a variety of host animals including, but not limited to, rabbits, mice, rats, etc. to induce the production of sera containing polyclonal antibodies specific for the antigen. Various adjuvants can be used to increase the immunological response, depending on the host species, and include, but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or combinations thereof. For example, monoclonal antibodies can be produced using hybridoma techniques including those known in the art and taught, for example, in Harlow et al., Antibodies: A Laboratory Manual, Cold Spring Harbor Laboratory Press, 2$^{nd}$ ed. (1988); Hammerling, et al., in *Monoclonal Antibodies and T-Cell Hybridomas*, Elsevier, New York (1981), pp. 563-681, or as described in Kohler, G. and Milstein, C., *Nature* 256: 495-497 (1975). Examples of yeast-based presentation methods that can be employed to select and generate the antibodies described herein include those disclosed in, for example, WO2009/036379; WO2010/105256; and WO2012/009568, each of which is herein incorporated by reference in its entirety. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

In some embodiments, a monoclonal antibody or antigen-binding fragment thereof is an antibody or antigen-binding fragment thereof produced by a clonal cell (e.g., hybridoma or host cell producing a recombinant antibody or antigen-binding fragment thereof), wherein the antibody or antigen-binding fragment thereof immunospecifically binds to TF (e.g., human TF) as determined, e.g., by ELISA or other antigen-binding assays known in the art or in the Examples provided herein. In some embodiments, a monoclonal antibody or an antigen-binding fragment thereof can be a chimeric or a humanized antibody or antigen-binding fragment thereof. In some embodiments, a monoclonal antibody or antigen-binding fragment thereof can be a Fab fragment or a F(ab')$_2$ fragment.

Antigen-binding fragments of antibodies described herein can be generated by any technique known in the art. For example, Fab and F(ab')$_2$ fragments described herein can be produced by proteolytic cleavage of immunoglobulin molecules, using enzymes such as papain (to produce Fab fragments) or pepsin (to produce F(ab')$_2$ fragments). A Fab fragment corresponds to one of the two identical arms of a tetrameric antibody molecule and contains the complete light chain paired with the VH and CH1 domains of the heavy chain. A F(ab')$_2$ fragment contains the two antigen-binding arms of a tetrameric antibody molecule linked by disulfide bonds in the hinge region.

Further, the antibodies or antigen-binding fragments thereof described herein can also be generated using various phage display and/or yeast-based presentation methods known in the art. In phage display methods, proteins are displayed on the surface of phage particles that carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with a scFv linker by PCR and cloned into a phagemid vector. The vector is electroporated in *E. coli* and the *E. coli* is infected with helper phage. Phage used in these methods are typically filamentous phage including fd and M13, and the VH and VL domains are usually recombinantly fused to either the phage gene III or gene VIII. Phage expressing an antibody or antigen-binding fragment thereof that binds to a particular antigen can be selected or identified with the antigen, e.g., using labeled antigen or antigen bound or captured to a solid surface or bead. Examples of phage display methods that can be used to make the antibodies or fragments described herein include those disclosed in Brinkman U. et al., *J Immunol Methods* 182: 41-50 (1995); Ames, R. S. et al., *J Immunol Methods* 184: 177-186 (1995); Kettleborough, C. A. et al., *Eur J Immunol* 24: 952-958 (1994); Persic, L et al., *Gene* 187: 9-18 (1997); PCT Appl. No. PCT/GB91/001134; International Publ. Nos. WO 90/02809; WO 91/10737; WO 92/01047; WO 92/18619; WO 93/11236; WO 95/15982; WO 95/20401; and WO 97/13844; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743; and 5,969,108.

In some embodiments, the antibody against hTF is a humanized antibody or antigen-binding fragment thereof can be selected from any class of immunoglobulins, including IgM, IgG, IgD, IgA and IgE, and any isotype, including IgG$_1$, IgG$_2$, IgG$_3$ and IgG$_4$. In some embodiments, such antibodies are used therapeutically to reduce antigenicity and HAMA (human anti-mouse antibody) responses when administered to a human subject. The humanized TF antibodies disclosed herein can be made by a variety of methods known in the art including phage display methods using antibody libraries derived from human immunoglobulin sequences. See U.S. Pat. Nos. 4,444,887 and 4,716,111; and PCT publications WO 98/46645, WO 98/50433, WO 98/24893, WO 98/16654, WO 96/34096, WO 96/33735, and WO 91/10741. Additionally, antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska et al., PNAS 91:969-973 (1994)), and chain shuffling (U.S. Pat. No. 5,565,332).

Humanized antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

In some embodiments, TF antibodies are humanized using CDR-grafting (EP 239,400; PCT publication WO 91/09967; U.S. Pat. Nos. 5,225,539; 5,530,101; and 5,585,089). Molecular modeling is used to identify human framework sequences that are the most structurally similar to the murine framework sequences. The murine CDR sequences are then grafted into the human frameworks and the combined sequences are modeled again, and only those grafted CDR/framework sequences that do not substantially alter the structural models are pursued. Mutations may then be introduced to remove residues that may be interfering with folding and structure or introduce sites that may be targets for modification (cleavage, glycosylation, amidation or others) or may produce strong T-cell epitopes causing the humanized antibody to be immunogenic.

In some embodiments, the antibody against hTF is a human antibody. Human antibodies can be produced using transgenic mice that are incapable of expressing functional endogenous immunoglobulins, but which can express human immunoglobulin genes. For example, the human heavy chain and light chain immunoglobulin gene complexes can be introduced randomly or by homologous recombination into mouse embryonic stem cells. Alternatively, nucleic acids encoding the human variable region and constant region can be introduced into mouse embryonic stem cells in addition to the human heavy and light chain genes. The mouse heavy chain and light chain immunoglobulin genes can be rendered non-functional separately or simultaneously with the introduction of human immunoglobulin loci by homologous recombination. In some embodiments, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a polypeptide of interest. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies.

For an overview of this technology for producing human antibodies, see Lonberg and Huszar, *Int. Rev. Immunol.* 13:65-93 (1995). For a detailed discussion of this technology for producing human antibodies and human monoclonal antibodies, see, e.g., PCT publications WO 98/24893; WO 92/01047; WO 96/34096; WO 96/33735; European Patent No. 0598877; U.S. Pat. Nos. 5,413,923; 5,625,126; 5,633,425; 5,569,825; 5,661,016; 5,545,806; 5,814,318; 5,885,793; 5,916,771; 5,939,598; 6,075,181; and 6,114,598. Affinity maturation strategies and chain shuffling strategies are known in the art and can be employed to generate high affinity human antibodies See, Marks et al., *Bio/Technology* 10:779-783 (1992).

Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope (Jespers et al., *Bio/technology* 12:899-903 (1988)).

Examples of techniques that can be used to produce single-chain Fvs and antibodies include those described in U.S. Pat. Nos. 4,946,778 and 5,258,498; Huston et al., *Methods in Enzymology* 203:46-88 (1991); Shu et al., *PNAS* 90:7995-7999 (1993); and Skerra et al., *Science* 240:1038-1040 (1988). Single chain antibodies are formed by linking the heavy and light chain fragments of the Fv region via an amino acid bridge, resulting in a single chain polypeptide. Techniques for the assembly of functional Fv fragments in *E. coli* can also be used (Skerra et al., *Science* 242:1038-1041 (1988)).

In addition, methods for producing chimeric antibodies are known in the art. See e.g., Morrison, *Science* 229:1202 (1985); Oi et al., *BioTechniques* 4:214 (1986); Gillies et al., *J. Immunol. Methods* 125:191-202 (1989); Neuberger et al., *Nature* 312:604-608 (1984); Takeda et al., *Nature* 314:452-454 (1985); U.S. Pat. Nos. 5,807,715; 4,816,567; and 4,816,397.

Once a TF antibody (i.e., humanized antibody) as disclosed herein has been produced by an animal, chemically synthesized, or recombinantly expressed, it can be purified by any method known in the art for purification of an immunoglobulin molecule. Purification methods include, for example, by chromatography (e.g., ion exchange, affinity, and sizing column chromatography), centrifugation, differential solubility, or by any other standard technique for the purification of proteins. In addition, the TF antibodies disclosed herein or fragments thereof can be fused to heterologous polypeptide sequences described herein or otherwise known in the art, to facilitate purification.

Nucleic Acid Molecules Encoding Humanized TF Antibodies and Polypeptides Thereof The present disclosure further provides an isolated polynucleotide molecule having a nucleotide sequence encoding the humanized TF antibody disclosed herein. In some embodiments, the isolated polynucleotide molecule comprises a nucleotide sequence of SEQ ID NOs:25-28 or 35-36, or fragments or variants thereof. In some embodiments, a humanized TF antibody as disclosed herein comprises a heavy chain or light chain variable region encoded by a nucleotide sequence selected from SEQ ID NO: 25 or 26, respectively. In some embodiments, a humanized TF antibody as disclosed herein comprises a heavy chain or light chain variable region encoded by a nucleotide sequence selected from SEQ ID NOs: 35 or 36, respectively. The differences in nucleotide sequence between SEQ ID NO: 25 and SEQ ID NO: 35 are indicated in bold below. The differences in nucleotide sequence between SEQ ID NO: 26 and SEQ ID NO: 36 are also indicated in bold below. In some embodiments, a humanized TF antibody as disclosed herein comprises a full length heavy chain or light chain sequence encoded by a nucleotide sequence selected from SEQ ID NO: 27 or 28, respectively.

```
SEQ ID NO: 25: nucleotide sequence of heavy chain
variable region of humanized TF antibody:
GAGGTCCAGCTGCAACAGTCGGGAGCAGAGGTGATGAAGCCCGGAGCCTCAGTGAAGATT

AGCTGCAAAGCCTCGGGATACACTTTCTCGTCATACTGGATTGAATGGGTCAAACAGGCC

CCCGGCCAAGGACTGGAGTGGATTGGCGAAATCCTTCCTGGGAGCGCCTCGACCAAGTAC

AACGAGAAGTTCAAGGGACGCGTGACATTCACCGCCGATACCAGCACCAACACTGCCTAC
```

-continued

ATGGAGCTTAGCTCATTGCGGTCCGAGGATACCGCTGTGTACTACTGTGCGCGGGACTAC

TATTACGGCTCCTCATACGGCTTCGCATACTGGGACAGGGTACCTTGGTCACGGTGTCC

TCC

SEQ ID NO: 35: nucleotide sequence of heavy chain
variable region of humanized TF antibody:
GAGGTCCAGCTGCAACAGTCGGGAGCAGAGGTGATGAAGCCCGGAGCCTCAGTGAAGATT

AGCTGCAAAGCCTCGGGATACACTTTCTCGTCATACTGGATTGAATGGGTCAAACAGGCC

CCCGGCCAAGGACTGGAGTGGATTGGCGAAATCCTTCCTGGGAGCGCCTCGACCAAGTAC

AACGAGAAGTTCAAGGGACGCGTGACATTCACCGCCGATACCAGCACCAACACTGCCTAC

ATGGAGCTTAGCTCATTGCGGTCCGAGGATACCGCTGTGTACTACTGTGCGCGGGACTAC

TATTACGGCTCCTCATACGGCTTCGCATACTGGGGTCAGGGAACCTTGGTCACGGTGTCC

TCC

SEQ ID NO: 26: nucleotide sequence of light chain
variable region of humanized TF antibody:
CAGGCTGTGGTCACTCAGGAGCCTTCGCTGACTGTCAGCCCGGGCGGTACCGTGACCCTG

ACCTGTCGCTCCTCAACTGGAGCAGTGACCACCTCCAACTACGCGAACTGGGTGCAGCAG

AAACCCGGCCAACTTCCTAAGGGACTGATCTCCGGCACTAACAACAGGGGACCTTGGACC

ACCGCCCGGTTCTCCGGTTCCATCCTTGGGGACAAGGCGGTGCTGACACTGTGGGGGGCC

CACACGGAGGACGAGGCCGTCTACTACTGCGCGCTCTGGTACTCCAACCATTGGGTGTTT

GGCGGAGGCACTAAGTTGACCGTGCTGGGC

SEQ ID NO: 36: nucleotide sequence of light chain
variable region of humanized TF antibody:
CAGGCTGTGGTCACTCAGGAGCCTTCGCTGACTGTCAGCCCGGGTGGCACCGTGACCCTG

ACCTGTCGCTCCTCAACTGGAGCAGTGACCACCTCCAACTACGCGAACTGGGTGCAGCAG

AAACCCGGCCAACTTCCTAAGGGACTGATCTCCGGCACTAACAACAGGGGACCTTGGACC

ACCGCCCGGTTCTCCGGTTCCATCCTTGGGGACAAGGCGGTGCTGACACTGTGGGGGGCC

CACACGGAGGACGAGGCCGTCTACTACTGCGCGCTCTGGTACTCCAACCATTGGGTGTTT

GGCGGAGGCACTAAGTTGACCGTGCTGGGC

SEQ ID NO: 27: nucleotide sequence of full length
heavy chain of humanized TF antibody:
GAGGTCCAGCTGCAACAGTCGGGAGCAGAGGTGATGAAGCCCGGAGCCTCAGTGAAGATT

AGCTGCAAAGCCTCGGGATACACTTTCTCGTCATACTGGATTGAATGGGTCAAACAGGCC

CCCGGCCAAGGACTGGAGTGGATTGGCGAAATCCTTCCTGGGAGCGCCTCGACCAAGTAC

AACGAGAAGTTCAAGGGACGCGTGACATTCACCGCCGATACCAGCACCAACACTGCCTAC

ATGGAGCTTAGCTCATTGCGGTCCGAGGATACCGCTGTGTACTACTGTGCGCGGGACTAC

TATTACGGCTCCTCATACGGCTTCGCATACTGGGGTCAGGGAACCTTGGTCACGGTGTCC

TCCGCGTCCACCAAGGGTCCCTCCGTGTTCCCTCTCGCGCCGTCCTCAAAGTCTACCTCC

GGTGGAACTGCCGCGCTCGGTTGTCTCGTGAAGGACTACTTCCCGGAGCCTGTGACTGTC

TCCTGGAACTCCGGGGCCCTCACCAGCGGAGTGCACACTTTCCCCGCCGTGCTGCAATCC

TCCGGCCTGTACAGCCTGTCCTCCGTCGTGACTGTGCCTAGCTCCTCCCTGGGAACCCAG

ACCTACATCTGCAACGTGAACCACAAGCCCTCCAACACCAAGGTCGACAAGAAGGTCGAA

CCGAAGTCGTGCGACAAGACTCATACGTGCCCTCCTTGCCCGGCCCCGGAACTGCTGGGA

GGCCCATCCGTGTTCCTGTTCCCACCCAAGCCTAAGGATACCCTGATGATCAGCAGAACA

CCGGAAGTGACCTGTGTGGTGGTGGACGTCAGCCACGAAGATCCCGAGGTCAAGTTCAAT

```
                         -continued
TGGTACGTGGACGGGGTGGAGGTGCACAACGCAAAGACCAAGCCCCGGGAGGAACAGTAC

AACTCCACCTATCGCGTGGTGTCGGTGCTGACGGTGCTGCACCAGGACTGGTTGAACGGA

AAGGAGTATAAGTGCAAAGTGTCGAACAAGGCCCTGCCCGCTCCTATCGAAAAGACCATC

TCCAAGGCCAAGGGCCAGCCGCGGGAACCCCAGGTCTACACTCTCCCACCGAGCCGCGAC

GAACTGACTAAGAATCAAGTGTCGCTGACTTGCCTCGTCAAGGGCTTCTACCCGTCCGAC

ATCGCCGTGGAATGGGAGAGCAACGGCCAGCCGGAAAACAACTACAAGACCACCCCTCCC

GTGCTGGATTCCGACGGGTCCTTCTTCCTGTACTCAAAACTGACCGTGGATAAGTCCAGA

TGGCAGCAGGGCAATGTCTTTTCATGCTCCGTGATGCACGAGGCTCTGCATAACCACTAC

ACCCAGAAGTCGCTGTCCCTGTCCCGGGGAAGTGA

SEQ ID NO: 28: nucleotide sequence of full length
light chain of humanized TF antibody:
CAGGCTGTGGTCACTCAGGAGCCTTCGCTGACTGTCAGCCCGGGTGGCACCGTGACCCTG

ACCTGTCGCTCCTCAACTGGAGCAGTGACCACCTCCAACTACGCGAACTGGGTGCAGCAG

AAACCCGGCCAACTTCCTAAGGGACTGATCTCCGGCACTAACAACAGGGGACCTTGGACC

ACCGCCCGGTTCTCCGGTTCCATCCTTGGGGACAAGGCGGTGCTGACACTGTGGGGGGCC

CACACGGAGGACGAGGCCGTCTACTACTGCGCGCTCTGGTACTCCAACCATTGGGTGTTT

GGCGGAGGCACTAAGTTGACCGTGCTGGGCCAGCCTAAGGCCGCACCATCGGTGACCCTG

TTCCCGCCGAGCTCGGAAGAACTCCAGGCCAACAAGGCCACTCTGGTCTGCCTGATTTCC

GACTTCTATCCCGGTGCTGTGACCGTGGCTTGGAAGGCCGATAGCTCGCCCGTGAAGGCC

GGAGTGGAAACCACCACCCCGTCCAAACAGTCCAACAATAAGTACGCCGCCTCCTCCTAC

TTGAGCCTCACGCCCGAGCAGTGGAAGTCTCACCGCTCATACTCCTGCCAAGTCACCCAC

GAAGGGAGCACTGTGGAAAAGACCGTGGCACCCACTGAGTGCTCGTGA
```

The present disclosure is further directed to an isolated polynucleotide having a nucleotide sequence encoding a first antibody, or antigen-binding fragment thereof, having an amino acid sequence that is at least 70%, at least 80%, at least 85%, at least 90%, at least 95%, at least 96%, at least 97%, at least 98%, or at least 99% identical to the amino acid sequence of a second antibody comprising an amino acid sequence selected from the group consisting of: (a) at least one CDR region of a VH domain of the humanized TF antibody as set forth in SEQ ID NOs:19-21; (b) at least two CDR regions of a VH domain of the humanized TF antibody as set forth in SEQ ID NOs:19-21; (c) at least three CDR regions of a VH domain of the humanized TF antibody as set forth in SEQ ID NOs:19-21; (d) at least one CDR region of a VL domain of the humanized TF antibody as set forth in SEQ ID NOs:22-24; (e) at least two CDR regions of a VL domain of the humanized TF antibody as set forth in SEQ ID NOs:22-24; and (f) at least three CDR regions of a VL domain of the humanized TF antibody as set forth in SEQ ID NOs:22-24. In some embodiments, the first antibody, or antigen-binding fragment thereof, has the same immunospecificity, or binds to the same epitope, as the second antibody.

The present disclosure further provides a polynucleotide molecule having a nucleotide sequence encoding an antigen-binding antibody fragment that binds to hTF without inhibiting normal TF-mediated blood coagulation compared to a normal plasma control, and optionally, can initiate an Fc-mediated mechanism. The present disclosure further provides an isolated polynucleotide molecule having a nucleotide sequence that can hybridize under stringent conditions to the complement of the nucleotide sequence of SEQ ID NOs:25-28 and that encodes a polypeptide that can bind to hTF without inhibiting normal TF-mediated blood coagulation compared to a normal plasma control, and optionally, can initiate an Fc-mediated mechanism. The present disclosure further provides an isolated polynucleotide molecule comprising a nucleotide sequence that has at least 95%, at least 96%, at least 97%, at least 98%, or at least 99% sequence identity to any of SEQ ID NOs:25-28 and encodes a polypeptide that can bind to hTF without inhibiting normal TF-mediated blood coagulation compared to a normal plasma control, and optionally, can initiate an Fc-mediated mechanism.

As known in the art, "sequence identity" between two nucleotide sequences is determined by comparing the nucleotide sequence of one polynucleotide molecule to the sequence of a second polynucleotide molecule. When discussed herein, whether any particular nucleotide sequence is identical to another nucleotide sequence can be determined using methods and computer programs/software known in the art such as, e.g., the Bestfit program, described above.

As used herein, "stringent conditions" refer to the ability of a first polynucleotide molecule to hybridize, and remain bound to, a second, filter-bound polynucleotide molecule in 0.5 M $NaHPO_4$, 7% sodium dodecyl sulfate (SDS), and 1 mM EDTA at 65° C., followed by washing in 0.2×SSC/0.1% SDS at 42° C. (see Ausubel et al. (eds.), *Current Protocols in Molecular Biology*, Vol. 1, Green Publishing Associates, Inc., and John Wiley & Sons, Inc., New York (1989), at p. 2.10.3).

Vectors and Host Cells

The present disclosure further provides a recombinant vector comprising a polynucleotide, as disclosed herein, and a host cell comprising the vector. Host cells are genetically engineered (transduced, transformed or transfected) with a vector of this invention which can be, for example, a cloning vector or an expression vector. The vector can be, for example, in the form of a plasmid, a viral particle, a phage, etc. Host cells can be cultured in conventional nutrient media modified as appropriate for activating promoters, selecting transformants or amplifying the genes of the present disclosure. The culture conditions, such as temperature, pH and the like, can be those previously used with the host cell selected for expression, and will be apparent to the ordinarily skilled artisan.

The present disclosure further provides a method of making a humanized TF antibody as disclosed herein, comprising: (a) expressing the antibody encoded by the isolated polynucleotide of the invention; and (b) recovering the antibody.

Fragments or portions of the polypeptides as disclosed herein can be employed for producing the corresponding full-length polypeptide by peptide synthesis; therefore, such fragments can be employed as intermediates for producing the full-length polypeptides. Likewise, fragments or portions of the polynucleotides as disclosed herein can be used to synthesize full-length polynucleotides of the present disclosure.

The polynucleotide molecules as disclosed herein can be employed for producing polypeptides by recombinant techniques. Thus, for example, a polynucleotide molecule can be included in any one of a variety of expression vectors for expressing a polypeptide. Such vectors include chromosomal, non-chromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector can be used if it is replicable and viable in the host.

The appropriate DNA sequence can be inserted into a vector by a variety of procedures. In general, the DNA sequence is inserted into an appropriate restriction endonuclease site(s) in a vector by procedures known in the art. Such procedures are known in the art.

The DNA sequence in the expression vector is operatively linked to one or more appropriate expression control sequences (promoter) to direct mRNA synthesis. Representative examples of such promoters include the LTR or SV40 promoter, the E. coli lac or trp, the phage lambda $P_L$ promoter and other promoters known to control expression of genes in prokaryotic or eukaryotic cells or their viruses. The expression vector also should contain a ribosome binding site for translation initiation, and a transcription terminator. The vector can also include appropriate sequences for amplifying expression, as discussed infra.

In addition, the expression vectors can contain one or more selectable marker genes to provide a phenotypic trait for selection of transformed host cells such as dihydrofolate reductase or neomycin resistance for eukaryotic cell culture, or tetracycline or ampicillin resistance in E. coli.

The vector containing the appropriate DNA sequence as hereinabove described, as well as an appropriate promoter or control sequence, can be employed to transform an appropriate host cell to permit the host cell to express the protein. Large numbers of suitable vectors and promoters are known to those of skill in the art, and are commercially available.

The following vectors are provided as non-limiting examples: Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, other plasmids or vectors can be used if they are replicable and stable in the host.

Promoter regions can be selected from any desired gene using CAT (chloramphenicol transferase) vectors or other vectors with selectable markers. Two appropriate vectors are PKK232-8 and PCM7. Particular named bacterial promoters include lad, lacZ, T3, T7, gpt, lambda $P_R$, $P_L$ and trp. Eukaryotic promoters include CMV immediate early, HSV thymidine kinase, early and late SV40, LTRs from retroviruses, and mouse metallothionein-I. Selection of the appropriate vector and promoter is well within the level of ordinary skill in the art. Promoters can be derived from operons encoding glycolytic enzymes such as 3-phosphoglycerate kinase (PGK), α-factor, acid phosphatase, or heat shock proteins, among others. The heterologous structural sequence to be expressed is assembled in appropriate phase with translation initiation and termination sequences, and, if necessary, a leader sequence capable of directing secretion of translated protein into the periplasmic space or extracellular medium. Optionally, the heterologous sequence can encode a fusion protein including an N-terminal or C-terminal identification peptide imparting desired characteristics, e.g., stabilization or simplified purification of expressed recombinant product.

In some embodiments, a signal sequence is used in constructing a vector containing VH and VL of a humanized TF antibody, antigen-binding fragment, or a polypeptide thereof, as disclosed herein. For example, in one embodiment, a nucleotide sequence (SEQ ID NO:29, encoding a signal peptide of SEQ ID NO:30) is used to express the heavy chain variable region of the humanized TF antibody. In another embodiment, a nucleotide sequence (SEQ ID NO:31, encoding a signal peptide of SEQ ID NO:32) is used to express the light chain variable region of a humanized TF antibody. In yet another embodiment, a nucleotide sequence (SEQ ID NO:33, encoding a signal peptide of SEQ ID NO:34) is used to express the heavy chain and light chain of a humanized TF antibody. Exemplary signal sequences are provided in Table 3 below.

TABLE 3

Nucleotide and amino acid sequences of exemplary signal sequences

| SEQ ID NO | Signal Sequence |
| --- | --- |
| SEQ ID NO: 29 | ATGGGATGGACTCTCGTGTTCCT TTTTCTCCTCTCTGTCACTGCCG GGGTGCATTCG |
| SEQ ID NO: 30 | MGWTLVFLFLLSVTAGVHS |
| SEQ ID NO: 31 | ATGGTGTCAAGCGCGCAGTTTCT GGGACTGCTCCTGCTGTGTTTCC AAGGAACCAGATGC |
| SEQ ID NO: 32 | MVSSAQFLGLLLLCFQGTRC |

TABLE 3-continued

Nucleotide and amino acid sequences of exemplary signal sequences

| SEQ ID NO | Signal Sequence |
|---|---|
| SEQ ID NO: 33 | ATGGAGACAGACACACTCCTGCT ATGGGTACTGCTGCTCTGGGTTC CAGGATCTACTGGC |
| SEQ ID NO: 34 | METDTLLLWVLLLWVPGSTG |

In a further embodiment, the present disclosure provides host cells containing the above-described constructs.

A variety of host-expression vector systems can be utilized to express the antibodies and antigen-binding fragments thereof described herein (e.g., an antibody or antigen-binding fragment thereof comprising the CDRs as set forth in SEQ ID NOs:19-24) (see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express an antibody or antigen-binding fragment thereof described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS (e.g., COS1 or COS), CHO, BHK, MDCK, HEK 293, NS0, PER.C6, VERO, CRL7O3O, HsS78Bst, HeLa, and NIH 3T3, HEK-293T, HepG2, SP210, R1.1, B-W, L-M, BSC1, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

In a specific embodiment, cells for expressing antibodies and antigen-binding fragments thereof described herein (e.g., an antibody or antigen-binding fragment thereof comprising the CDRs set forth in SEQ ID NOs:19-24) are CHO cells, for example CHO cells from the CHO GS System™ (Lonza). In a particular embodiment, cells for expressing antibodies described herein are human cells, e.g., human cell lines. In a specific embodiment, a mammalian expression vector is pOptiVEC™ or pcDNA3.3. In a particular embodiment, bacterial cells such as *Escherichia coli*, or eukaryotic cells (e.g., mammalian cells), especially for the expression of whole recombinant antibody molecule, are used for the expression of a recombinant antibody molecule. For example, mammalian cells such as Chinese hamster ovary (CHO) cells in conjunction with a vector such as the major intermediate early gene promoter element from human cytomegalovirus is an effective expression system for antibodies (Foecking, M. K. and Hofstetter, H., *Gene* 45: 101-105 (1986); and Cockett, M. I. et al., *Biotechnology* 8: 662-667 (1990)). In certain embodiments, antibodies or antigen-binding fragments thereof described herein are produced by CHO cells or NS0 cells.

In addition, a host cell strain can be chosen which modulates the expression of the inserted sequences, or modifies and processes the gene product in the specific fashion desired. Such modifications (e.g., glycosylation) and processing (e.g., cleavage) of protein products can contribute to the function of the protein. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, MDCK, HEK 293, NIH 3T3, W138, BT483, Hs578T, HTB2, BT2O and T47D, NS0 (a murine myeloma cell line that does not produce any endogenous immunoglobulin chains), CRL7O3O, COS (e.g., COS1 or COS), PER.C6, VERO, HsS78Bst, HEK-293T, HepG2, SP210, R1.1, B-W, L-M, BSC1, BSC40, YB/20, BMT10 and HsS78Bst cells. In certain embodiments, anti-TF antibodies described herein (e.g., an antibody or antigen-binding fragment thereof comprising the CDRs set forth in SEQ ID NOs:19-24) are produced in mammalian cells, such as CHO cells.

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present disclosure. Appropriate cloning and expression vectors for use with prokaryotic and eukaryotic hosts are described by Sambrook, et al., *Molecular Cloning: A Laboratory Manual, Second Edition*, Cold Spring Harbor, N.Y. (1989).

Transcription of the DNA encoding the polypeptides disclosed herein by higher eukaryotes can be increased by inserting an enhancer sequence into the vector. Enhancers are cis-acting elements of DNA, usually about from 10 to 300 bp that act on a promoter to increase its transcription or amplifying expression. Examples include the SV40 enhancer on the late side of the replication origin bp 100 to 270, a cytomegalovirus early promoter enhancer, the polyoma enhancer on the late side of the replication origin, and adenovirus enhancers.

Following transformation of a suitable host strain and growth of the host strain to an appropriate cell density, the selected promoter can be induced by appropriate means (e.g., temperature shift or chemical induction) and the cells are cultured for an additional period.

Where the desired protein is retained intracellularly, cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents, or a combination thereof. Such methods are well known to those skilled in the art.

The polypeptides as disclosed herein can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides as disclosed herein can be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides as disclosed herein can be glycosylated or can be non-glycosylated. Polypeptides as disclosed herein can also include an initial methionine amino acid residue.

Once the humanized hTF antibodies or antigen-binding fragments thereof described herein have been produced by recombinant expression, they can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies or antigen-binding fragments thereof described herein can be fused to heterologous polypeptide sequences described herein or otherwise known in the art to facilitate purification.

In some embodiments, the humanized TF antibodies or antigen-binding fragments thereof described herein are isolated or purified. Generally, an isolated antibody or antigen-binding fragment thereof is one that is substantially free of other antibodies or antigen-binding fragments thereof with different antigenic specificities than the isolated antibody or antigen-binding fragment thereof. For example, in a particular embodiment, a preparation of an antibody or antigen-binding fragment thereof described herein is substantially free of cellular material and/or chemical precursors.

Antibody-Drug Conjugates

The humanized tissue factor antibodies, as disclosed herein, can be used to target hTF, including in in vivo therapeutic methods. The disclosed humanized TF antibodies include derivatives of antibodies that are modified or conjugated by the covalent attachment of any type of molecule to the antibody. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to, specific chemical cleavage, acetylation, formylation, metabolic synthesis of tunicamycin, etc. Additionally, the derivatives can contain one or more non-classical amino acids.

The disclosed humanized TF antibodies can be used alone or in combination with other compositions. The antibodies can be recombinantly fused to a heterologous polypeptide at the N- or C-terminus, or chemically conjugated (including covalent and non-covalent conjugations) to a polypeptide or other compositions. For example, the disclosed humanized tissue factor antibodies can be recombinantly fused or conjugated to molecules useful as labels in detection assays, or as effector molecules such as heterologous polypeptides, drugs, radionuclides, or toxins. See, e.g., WO 92/08495, WO 91/14438, WO 89/12624, U.S. Pat. No. 5,314,995, and EP 0396 387.

In some embodiments, the disclosed humanized tissue factor antibodies are conjugated to at least one cytotoxic agent. A "cytotoxic agent" is any agent that is toxic or otherwise detrimental to cells, which results in the death of a cell, induces cell death, or otherwise decreases the cell's viability. In some embodiments, the cell is a cancer cell or tumor cell. The cytotoxic agent that is conjugated to the tissue factor antibody described herein is also called the "payload" or "cytotoxic payload."

In some embodiments, the antibody-drug conjugate disclosed herein is represented by the formula: Ab-(L-CA)$_n$, wherein Ab is a humanized antibody that binds to human tissue factor comprising a heavy variable chain comprising an amino acid sequence set forth as SEQ ID NOs:9-11 and a light variable chain comprising an amino acid sequence set forth as SEQ ID NOs:12-16; and (L-CA)$_n$ is a linker-cytotoxic agent moiety, wherein L is a linker, CA is a cytotoxic agent, and n is a number selected from the group consisting of 1 to 20, 1 to 10, 1 to 9, 1 to 8, 1 to 7, 1 to 6, and 1 to 5.

The cytotoxic agent that can be conjugated through the linker to the humanized tissue factor antibody disclosed herein can be selected from various classes of agents. Exemplary cytotoxic agents and classes of agents that can be conjugated to the humanized tissue factor antibodies and antigen-binding fragments disclosed herein are discussed in Polakis, P., *Pharmacol. Rev.* 68:3-19 (2016); Perez, H. L. et al., *Drug Discovery Today* 19:869-881 (2014); Diamantis, N. and Banerji, U., *British Journal of Cancer* 114:362-367 (2016).

In some embodiments, the disclosed humanized tissue factor antibodies can be conjugated to a cytotoxic agent that includes, but is not limited to, antimetabolites (e.g., methotrexate, 6-mercaptopurine, 6-thioguanine, cytarabine, 5-fluorouracil decarbazine); alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin); anthracyclines (e.g., daunorubicin (formerly daunomycin) and doxorubicin); antibiotics (e.g., dactinomycin (formerly actinomycin), bleomycin, mithramycin, and anthramycin (AMC)); anti-mitotic agents (e.g., vincristine and vinblastine); and radionuclides. Examples of radionuclides useful as therapeutic agents include, but are not limited to, $^{131}$I, $^{177}$Lu, $^{90}$Y, and $^{186}$Re.

In some embodiments, the cytotoxic agent is a tubulin inhibitor, such as auristatin or a maytansinoid. In some embodiments, the cytotoxic agent is auristatin, a dolastatin analogue, or an auristatin derivative. Dolastatin analogues and auristatins block tubulin assembly and cause G2/M phase cell cycle arrest. Auristatins include monomethyl auristatin E (MMAE) and monomethyl auristatin F (MMAF). Useful dolastatin analogues and conjugation strategies are disclosed in U.S. Pat. No. 7,659,241.

In some embodiments, the cytotoxic agent is a maytansinoid (e.g., maytansine) or a maytansinoid analog. Maytansine and its analogs (maytansinoids DM1 and DM4) are potent microtubule-targeted compounds that inhibit proliferation of cells at mitosis. See, Lopus, M. et al., *Mol. Cancer Ther.* 9:2689-2699 (2010). The use of these cytotoxic agents as conjugates and methods for conjugating such agents to antibodies are described in U.S. Published Appl. No. 2012/

0009181, ¶¶[0025]-[0030], [0034], [0036], [0038], [0040], [0169], [0185], and [0211]-[0218].

In some embodiments, the cytotoxic agent is an RNA polymerase II inhibitor, such as the mushroom toxin amatoxin or an amatoxin analogue. α-Amanitin is a bicyclic octapeptide that is an exemplary amatoxin. One mushroom species from which α-Amanitin is derived is *Amanita phalloides* (Moldenhauer, G. et al., *J Natl. Cancer Inst.* 104:622-634 (2012). Analogs and conjugates thereof are disclosed in Published Appl. Nos. WO2010/115629 and WO2014/043403.

In some embodiments, the cytotoxic agent is a Topoisomerase I (Topo I) inhibitor, such as Camptothecin or CPT (Ulukan, H. et al., *Drugs* 62:2039-2057 (2002), or a CPT analogue. Exemplary CPT analogues include Topotecan, Irinotecan, Silatecan, Cositecan, Exatecan, Lurtotecan, Gimatecan, Belotecan, and Rubitecan. Id.

In some embodiments, the cytotoxic agent is a DNA alkylating agent, such as Duocarmycin or a Duocarmycin analogue. Useful Duocarmycin analogues and conjugates thereof are disclosed in Published Appl. No. WO2011/133039. The duocarmycin derivatives can have heteroatoms or polar groups at selected positions in the DNA-binding moiety or in substituents on the DNA-binding or DNA-alkylating moiety. In some embodiments, the conjugate of duocarmycin derivatives contain one or more pro-moieties. In a more specific embodiment, such a conjugate has a sufficient stability in the circulation, but is activated to release the duocarmycin derivatives at the target site. The length and nature of the linker between functional moiety and the duocarmycin derivatives can be appropriately modified. In one aspect, the linker has a reduced linker length. In another aspect, the linker contains a self-elimination spacer system. In yet another aspect, the linker between functional moiety and the duocarmycin derivatives contains one or more groups designed to improve the pharmacokinetic properties of the conjugate. In yet another aspect, the linker between the functional moiety and the duocarmycin derivatives contains one or more groups designed to improve the pharmacokinetic properties of the conjugate. These groups, for example, can include a carbonate, carbamate, ureum, ester, amide, imine, hydrazone, hydrazide, oxime, disulfide, acetal, or ketal group, as described in Published Appl. No. WO 2011/133039, which is herein incorporated by reference.

In some embodiments, the cytotoxic agent is a DNA damaging agent, such as Calicheamicin or a Calicheamicin derivative. See Maiese, W. M. et al., *J. Antibiot.* 42 558-563 (1989); Watanabe, C. M. et al., *Chem Biol.* 9:245-251 (2002).

In some embodiments, the cytotoxic agent is a pyrrolobenzodiazepine (PBD). PBDs bind to discrete DNA sequences causing lethal lesions, and have not been found to have cross-resistance with common chemotherapeutic agents. See Rio-Doria, J. et al., *Cancer Res.* 77:2686-2698 (2017). As an exemplary DNA minor groove binding agent, PBDs bind and cross-link specific sites of DNA of the cancer cell. This blocks the cancer cells' division without distorting its DNA helix, thus potentially avoiding the common phenomenon of emergent drug resistance. Useful PBDs and conjugates thereof are disclosed in U.S. Pat. No. 9,821,074.

In some embodiments, the cytotoxic agent is a tubulysin analogue, as described in U.S. Pat. No. 9,688,721 and Cohen, R. et al., *Cancer Res.* 74:5700-5710 (2014).

Other cytotoxic agents that can be conjugated to the humanized TF antibodies disclosed herein include, but are not limited to, paclitaxol, cytochalasin B, gramicidin D, ethidium bromide, emetine, mitomycin, etoposide, tenoposide, colchicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

In some embodiments, the cytotoxic agent can be a protein or polypeptide possessing a desired biological activity. Such proteins can include, for example, a toxin such as abrin, ricin A, *pseudomonas* exotoxin, or diphtheria toxin; a protein such as tumor necrosis factor, α-interferon, β-interferon, nerve growth factor, platelet derived growth factor, tissue plasminogen activator, an apoptotic agent, e.g., TNF-alpha, TNF-beta, AIM I (see, WO 97/33899), AIM II (see, WO 97/34911), Fas Ligand (Takahashi et al., *Int. Immunol.* 6:1567-1574 (1994)), VEGI (see, WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such cytotoxic agents to antibodies are known, see, e.g., Arnon et al., "Monoclonal Antibodies For Immunotargeting of Drugs In Cancer Therapy," in *Monoclonal Antibodies And Cancer Therapy*, Reisfeld et al., eds., Alan R. Liss, Inc. (1985), pp. 243-256; Hellstrom et al., "Antibodies For Drug Delivery," in *Controlled Drug Delivery,* 2nd Ed., Robinson et al., eds., Marcel Dekker, Inc. (1987), pp. 623-653; Thorpe, "Antibody Carriers Of Cytotoxic Agents In Cancer Therapy: A Review," in *Monoclonal Antibodies '84: Biological And Clinical Applications*, Pinchera et al., eds. (1985), pp. 475-506; "Analysis, Results, and Future Prospective Of The Therapeutic Use Of Radiolabeled Antibody In Cancer Therapy," in *Monoclonal Antibodies For Cancer Detection And Therapy*, Baldwin et al., eds., Academic Press (1985), pp. 303-316; and Thorpe et al., "The Preparation and Cytotoxic Properties of Antibody-Toxin Conjugates," *Immunol. Rev.* 62:119-158 (1982), all of which are herein incorporated by reference.

The average ratio of drug (e.g., cytotoxic agent) molecules per antibody molecule is referred to herein as the "drug-antibody-ratio (DAR)." As noted above, the antibody-drug conjugate disclosed herein is represented by the formula Ab-(L-CA)$_n$; the subscript "n" is selected from the group consisting of 1 to 20, 1 to 10, 1 to 9, 1 to 8, 1 to 7, 1 to 6, and 1 to 5, and reflects the number of cytotoxic agent molecules that will be used to calculate the DAR. In some embodiments, the DAR is 1-8, 3-7, 3-5, or 2.5-3.5. In some embodiments, the antibody-drug conjugate has a DAR of 1-8. In some embodiments, the antibody-drug conjugate has a DAR of 4. In some embodiments, the antibody-drug conjugate has a DAR of 2.

The present disclosure encompasses humanized tissue factor antibodies that are conjugated to a cytotoxic agent through one or more linkers, linker sequences, or linking groups (hereafter "linkers"). In some embodiments, the linkers are cleavable linkers under intracellular conditions such that the cleavage of the linker releases the cytotoxic agent from the antibody into the intracellular environment. In some embodiments, the linkers are not cleavable and the cytotoxic agent is released by antibody degradation. See, e.g., Published Appl. No. US 2005/0238649, which is herein incorporated by reference.

In some embodiments, the linker technology that is used to conjugate the humanized tissue factor antibodies disclosed herein to a cytotoxic agent, as described herein, is as described in Published Appl. No. WO 2011/133039, which is herein incorporated by reference in its entirety.

In some embodiments, the linker technology that is used to conjugate the humanized tissue factor antibodies disclosed herein to a cytotoxic agent, as described herein, is the linker-drug technology described in U.S. Pat. No. 7,659,241, which is herein incorporated by reference. See U.S. Pat. No. 7,659,241; col. 60, line 10 to col. 83, line 47; col. 83, line 51 to col. 91, line 67; and col. 92, line 3 to col. 101, line 33.

In some embodiments, the linker technology that is used to conjugate the humanized tissue factor antibodies disclosed herein to a cytotoxic agent, as described herein, is as described in U.S. Pat. No. 9,504,758, which is herein incorporated by reference in its entirety.

In some embodiments, the humanized tissue factor antibodies disclosed herein can be fused to either the N- or C-terminus of a heterologous protein (e.g., immunoglobulin Fc polypeptide or human serum albumin polypeptide). For example, antibodies can be fused to albumin, such as recombinant human serum albumin (see, e.g., U.S. Pat. No. 5,876,969, EP 0413622, and U.S. Pat. No. 5,766,883)), resulting in a chimeric polypeptide. In other embodiments, antibodies can be fused to the mature form of human serum albumin (i.e., amino acids 1-585 of human serum albumin as shown in FIGS. 1 and 2 of EP Patent 0322094). In other embodiments, antibodies can be fused with polypeptide fragments comprising, or alternatively consisting of, amino acid residues 1-z of human serum albumin, where z is an integer from 369 to 419, as described in U.S. Pat. No. 5,766,883. Antibodies fused or conjugated to polypeptides or other molecules of interest can also be used in in vitro immunoassays and purification methods using methods known in the art. See e.g., Harbor et al., supra, and PCT publication WO 93/21232; EP 439,095; Naramura et al., *Immunol. Lett.* 39:91-99 (1994); U.S. Pat. No. 5,474,981; Gillies et al., *PNAS* 89:1428-1432 (1992); and Fell et al., *J. Immunol.* 146:2446-2452 (1991).

In some embodiments, the humanized tissue factor antibodies disclosed herein can be conjugated to a second antibody to form an antibody heteroconjugate as described, e.g., in U.S. Pat. No. 4,676,980.

Pharmaceutical Compositions

Provided herein are compositions comprising a humanized TF antibody or antigen-binding fragment thereof disclosed herein having the desired degree of purity in a physiologically acceptable carrier, excipient or stabilizer (Remington's Pharmaceutical Sciences (1990) Mack Publishing Co., Easton, Pa.). Acceptable carriers, excipients, or stabilizers are nontoxic to recipients at the dosages and concentrations employed.

In some embodiments, compositions comprising a humanized TF antibody or antigen-binding fragment thereof are provided in formulations with a pharmaceutically acceptable carrier (see, e.g., Gennaro, Remington: The Science and Practice of Pharmacy with Facts and Comparisons: Drugfacts Plus, 20th ed. (2003); Ansel et al., Pharmaceutical Dosage Forms and Drug Delivery Systems, 7th ed., Lippencott, Williams and Wilkins (2004); Kibbe et al., Handbook of Pharmaceutical Excipients, 3rd ed., Pharmaceutical Press (2000)).

Pharmaceutical compositions described herein can be useful in treating a condition such as cancer. Examples of cancer that can be treated in accordance with the methods described herein include, but are not limited to, carcinomas, sarcomas, lymphomas, and leukemias of any human and non-human animal species including swine, cats, dogs and higher primates.

The pharmaceutical compositions (and methods of treatment) disclosed herein are suitable for the treatment of solid tumors, which can be characterized by extensive vasculature (microvascularized tumors), including carcinomas, sarcomas, and lymphomas of various cell types. Solid tumors targeted by the treatment of the present disclosure include, but are not limited to: cancers of the head and neck, including squamous cell and epidermoid carcinomas; adenocarcinomas, including prostatic, scirrhous, and mammary adenocarcinomas; lymphosarcoma; fibrosarcoma; osteosarcoma; leiomyosarcoma; chondroma; cancer of the prostate, lung, breast, ovary, stomach (gastric), pancreas, larynx, esophagus, testes, liver, parotid, biliary tract, colon, rectum, colorectal, cervix, uterus, endometrium, kidney, bladder, or thyroid; primary tumors and metastases; melanomas; glioblastoma; Kaposi's sarcoma; non-small cell lung cancer (NSCLC), including squamous and adeno types; advanced malignancies; and hematologic malignancies, such as, e.g., leukemias, lymphomas, and myelomas. Because the antibodies of the invention do not inhibit normal TF-mediated blood coagulation, normal plasma clotting is not affected in patients treated with the humanized TF antibodies disclosed herein.

In some embodiments, the solid tumor that may be treated by the compositions (and methods) disclosed herein are solid tumors selected from the group consisting of breast cancer, ovarian cancer, thyroid cancer, colorectal cancer, esophageal cancer, gastric cancer, melanoma, brain cancer, head and neck cancer, epidermal, sarcoma, kidney cancer, pancreatic cancer, prostate cancer, liver cancer, urothelial, and lung cancer.

In some embodiments, the hematological malignancies that may be treated by the compositions (and methods) disclosed herein are selected from the group consisting of acute lymphocytic leukemia (ALL), acute myeloid leukemia (AML), chronic lymphocytic leukemia (CLL), small lymphocytic lymphoma (SLL), multiple myeloma (MM), Hodgkin's lymphoma (HL), non-Hodgkin's lymphoma (NHL), mantle cell lymphoma (MCL), follicular lymphoma (FL), Waldenstrom's macroglobulinemia (WM), diffuse large B-cell lymphoma (DLBCL), marginal zone lymphoma (MZL), hairy cell leukemia (HCL), Burkitt's lymphoma (BL), and Richter's transformation.

In some embodiments, the pharmaceutical compositions described herein are for use as a medicament (e.g., to treat cancer). The pharmaceutical compositions described herein may also be used as a diagnostic, e.g., to detect the presence of TF in a sample obtained from a patient (e.g., a human patient).

The compositions to be used for in vivo administration can be sterile. This is readily accomplished by filtration through, e.g., sterile filtration membranes.

In some embodiments, pharmaceutical compositions are provided, wherein the pharmaceutical composition comprises humanized TF antibodies, antigen-binding fragments thereof, or antibody-drug conjugates, all as described herein, and a pharmaceutically acceptable carrier. In some embodiments, a pharmaceutical composition comprises (i) an isolated antibody or antigen-binding fragment thereof that specifically binds to human TF, comprising (a) the heavy chain variable region (VH) complementarity determining region (CDR) 1, VH CDR2, VH CDR3 and light chain variable region (VL) CDR1, CDR2, and CDR3 sequences of SEQ ID NOs:19-24, respectively, (b) a variable heavy chain region comprising the amino acid sequence selected from SEQ ID NOs:9-11 and a variable light chain region comprising the amino acid sequence selected from SEQ ID NOs:12-16, and (ii) a pharmaceutically acceptable excipient.

Assays for Antibody Binding

The humanized tissue factor antibodies or antigen-binding fragments thereof disclosed herein can be assayed for immunospecific binding to human tissue factor by any suitable method known in the art. Exemplary immunoassays that can be used include, but are not limited to, competitive and non-competitive assay systems using techniques such as Biacore™ analysis, FACS (Fluorescence activated cell sorter) analysis, immunofluorescence, immunocytochemistry, Western blots, radio-immunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays. Such assays are routine and well known in the art (see e.g., Ausubel et al, eds, *Current Protocols in Molecular Biology*, Vol. 1, John Wiley & Sons, Inc., New York (1994)). Exemplary immunoassays are described briefly below and several are exemplified in the Examples.

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., Western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols, see e.g., Ausubel, F. et al., eds., *Current Protocols in Molecular Biology*, Vol. 1, John Wiley & Sons, Inc., New York (1994), at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), incubating the membrane with primary antibody (the antibody of interest) diluted in incubating buffer, washing the membrane in washing buffer, incubating the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}P$ or $^{125}I$) diluted in incubating buffer, washing the membrane in wash buffer, and detecting the presence of the antigen. One skilled in the art would be knowledgeable as to the parameters that can be modified to increase the signal detected and to reduce the background noise. See, e.g., Ausubel, F. et al., *Current Protocols in Molecular Biology*, Vol. 1, John Wiley & Sons, Inc., New York (1994) at 10.8.1.

ELISAs comprise preparing antigen, coating the well of a 96-well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs, the antibody of interest does not have to be conjugated to a detectable compound; instead, a second antibody (which recognizes the antibody of interest) conjugated to a detectable compound can be added to the well. Further, instead of coating the well with the antigen, the antibody can be coated to the well. In this case, a second antibody conjugated to a detectable compound can be added following the addition of the antigen of interest to the coated well. One skilled in the art would be knowledgeable of the parameters that can be modified to increase the signal detected as well as other known variations of ELISAs. See, e.g., Ausubel, F. et al., eds., *Current Protocols in Molecular Biology*, Vol. 1, John Wiley & Sons, Inc., New York (1994) at 11.2.1.

The binding affinity of an antibody or an antigen-binding fragment thereof to an antigen and the off-rate of an antibody-antigen interaction can be determined by competitive binding assays. One example of a competitive binding assay is a radioimmunoassay comprising the incubation of labeled antigen (e.g., $^{3}H$ or $^{125}I$), or fragment or variant thereof, with the antibody of interest in the presence of increasing amounts of unlabeled antigen, and the detection of the antibody bound to the labeled antigen. The affinity of the antibody of interest for hTF and the binding off-rates can be determined from the data by Scatchard plot analysis. Competition with a second antibody can also be determined using radioimmunoassays. In this case, the hTF is incubated with the antibody of interest conjugated to a labeled compound (e.g., compound labeled with $^{3}H$ or $^{125}I$) in the presence of increasing amounts of an unlabeled second antibody. This kind of competitive assay between two antibodies can also be used to determine if two antibodies bind the same or different epitopes.

Blood Coagulation

Blood coagulation is a complex process involving three interacting components: blood vessels, blood coagulation factors, and blood platelets. Blood coagulation factors are proteins or glycoproteins present in the blood as inactive precursors. When bleeding occurs, the coagulation cascade is initiated and the inactive coagulation factors are converted to active proteases or enzymes. Coagulation factors are activated in sequence in the coagulation cascade, with the aid of cofactors (such as calcium, TF, and phospholipids), resulting in the eventual formation of a fibrin clot. Fibrin is a sticky, thread-like protein that is insoluble in blood and provides the foundation for platelet adhesion and blood coagulation.

If bleeding results from an injury outside of the vasculature (such as an abrasion or cut of the skin), the extrinsic pathway is initiated. If injury occurs within the blood vessel itself, the intrinsic pathway is activated. Many bleeding episodes activate both pathways.

The extrinsic coagulation pathway is triggered on the extravascular cell surface when TF is exposed to blood following some physical injury. TF can bind to both activated and inactivated forms of factor VII. In the extrinsic pathway, a small amount of circulating activated factor VII (factor VIIa) complexes with TF following its release. This TF/factor VIIa complex initiates coagulation by converting factors IX and X to active forms.

This reaction is amplified by a feedback mechanism in which factors VIIa, IXa and Xa activate additional factor VII bound to TF. Factor Xa, in complex with a cofactor, factor Va, and phospholipids, continues in the cascade activating prothrombin (also known as factor II) to thrombin (also known as factor IIa). Another feedback mechanism involving thrombin works to activate factors V, VIII and XI. Factor VIIIa complexes with factor IXa on platelet surfaces to activate factor X, resulting in more local thrombin generation. Thrombin is responsible for the eventual generation of fibrin.

In the intrinsic pathway, circulating activated factor XII, in complex with high molecular weight kininogen and prekallikrein, comes into contact with the exposed subendothelial membrane to initiate coagulation and activate factor XI. Factor XIa complexes with calcium to activate factor IX. Factor IXa, in conjunction with factor VIIIa, calcium and phospholipids, results in the activation of factor X to factor Xa and subsequent thrombin generation. After activation of factor X, the extrinsic and intrinsic pathways merge.

The final step of clot formation is the conversion of plasma soluble fibrinogen to insoluble fibrin as a result of the cleavage of peptide bonds. Cleavage occurs as the result of the proteolytic enzyme thrombin, which is produced from prothrombin. Conversion of prothrombin to thrombin requires clotting factors, in addition to calcium. The fibrin clot is a crosslinked matrix, which entraps the formed elements of the blood thereby sealing off the site of bleeding. Formed elements consist of platelets, white blood cells, and red blood cells.

TF is a cell-anchored component that, together with factor VIIa, initiates blood coagulation in vivo. TF is a transmembrane glycoprotein with a 219 residue extracellular region, a 23 residue transmembrane region and a 21 residue cytoplasmic region. The extracellular region of TF has two fibronectin III-like domains and a distribution of disulfide bridges characteristic of class-II cytokine and interferon receptors. The cytoplasmic region of TF contains three serine residues that can be phosphorylated and have been implicated in cell signaling. Aberg, M. and Siegbahn, A., *J Thromb Haemost* 11: 817-825 (2013).

TF forms a tight complex ($K_d$-pmol) with its native ligand, i.e., factor VIIa. In the complex, VIIa wraps around TF (Banner, D. W., et al., *Nature* 380:41-46 (1996)) and forms an extensive region of contact with the TF surface. TF binds and allosterically activates factor VIIa (fVIIa) and the complex TF/fVIIa is responsible for thrombin generation via activation of factors IX and X and is the major initiator of blood clotting under physiological conditions. Antibodies that bind to the TF-FVIIa interaction site can inhibit TF-FVIIa interaction, thus inhibiting or blocking blood coagulation. The humanized TF antibodies or antigen-binding fragments thereof disclosed herein bind to TF, e.g., hTF, but do not inhibit TF-mediated blood coagulation compared to a normal plasma control.

As used herein, the term "normal plasma control" means plasma pooled from normal human donors, such as that offered by George King Bio-Medical, Inc., Kansas (POOLED NORMAL PLASMA).

In some embodiments, the effect of the disclosed humanized TF antibodies or antigen-binding fragments thereof on TF-mediated blood coagulation can be determined using a blood clotting assay. For example, blood clotting assays known in the art, such as those described in, e.g., Morrissey, J. H., et al., *Thrombosis Research* 52:247-261 (1988), and Fang, C. H., et al., *Thrombosis and Haemostasis* 76:361-368 (1996), can be used to determine the effect of an anti-TF antibody on blood coagulation. Other blood clotting assays include, but are not limited to, one-stage prothrombin time assay (Miale J. B., *Laboratory Medicine, Hematology*, CN Mosbey Co., St. Louis (1977), and two-stage clotting assay (Bach et al., *Biochemistry* 15:4007-4020 (1986)) can also be used.

Other assays, such as the one described in Example 8, measure the activation of Factor X, which is a surrogate marker for tissue factor-mediated blood coagulation. This assay (e.g., Tissue Factor Human Chromogenic Activity Assay Kit, AbCam) measures the ability of lipoprotein TF/FVIIa to activate factor X (FX) to factor Xa. The amidolytic activity of the TF/FVIIa complex is quantitated by the amount of FXa produced using a highly specific FXa substrate, releasing a yellow para-nitroaniline (pNA) chromophore. The change in absorbance of the pNA at 405 nm is directly proportional to the enzymatic activity of TF. A humanized TF antibody, as disclosed herein, "does not inhibit TF-mediated blood coagulation compared to a normal plasma control" where, in an hTF coagulation assay, as provided in Chen, C. et al., *Hybridoma* 24: 78-85 (2005), the clotting time of a blood sample treated with the antibody is about 150% or less, about 140% or less, about 130% or less, about 120% or less, about 110% or less, or about 100% or less of the clotting time of a normal plasma control.

Further, a humanized TF antibody, as disclosed herein, "does not inhibit TF-mediated blood coagulation compared to antibodies previously shown to neutralize the procoagulant activity of TF such as Sekisui ADG4507 or ADG4508" where, in a human TF chromogenic activity assay, TF-dependent activation of Factor X is measured using a highly specific Factor Xa substrate that upon cleavage releases a yellow chromophore.

Fc-Mediated Mechanisms

In some embodiments, the humanized TF antibodies and antigen-binding fragments thereof disclosed herein are capable of binding to hTF without inhibiting TF-mediated blood coagulation compared to a normal plasma control, and can initiate one or more Fc-mediated mechanisms.

When antibodies are exposed to proteolytic enzymes such as papain or pepsin, several major fragments are produced. The fragments that retain antigen-binding ability consist of the two "arms" of the antibody's Y configuration and are termed F(ab) (fragment-antigen binding) or F(ab')$_2$ which represent two Fab arms linked by disulfide bonds. The other major fragment produced constitutes the single "tail" or central axis of the Y and is termed Fc (fragment-crystalline) for its propensity to crystallize from solution. The Fc fragment of IgG, IgA, IgM, or IgD consists of dimers of the two carboxyl-terminal domains of each antibody (i.e., CH2 and CH3 in IgG, IgA and IgD, and CH3 and CH4 in IgM). The IgE Fc fragment, by contrast, consists of a dimer of its three-carboxyl-terminal heavy chain domains (C2, C3 and C4).

The Fc fragment contains the antibody's biologically "active site," which enables the antibody to "communicate" with other immune system molecules or cells and thereby activate and regulate immune system defensive functions or host-mediated mechanisms. Such communication occurs when active sites within the antibody Fc region binds to molecules termed Fc receptors. Fc receptors are molecules that bind with high affinity and specificity to active sites within immunoglobulin Fc regions. Fc receptors can exist as integral membrane proteins within a cell's outer plasma membrane or can exist as free, "soluble" molecules that freely circulate in blood plasma or other body fluids.

For each of the five antibody classes, there are several types of Fc receptors that specifically bind to the Fc region of that class and perform distinct functions. Thus, IgE Fc receptors bind with high affinity to only IgE Fc regions or to isolated IgE Fc fragments. It is known that different types of class-specific Fc receptors exist, which recognize and bind to different locations within the Fc region. For example, certain IgG Fc receptors bind exclusively to the second constant domain of IgG (CH2), while Fc receptors mediating other immune functions bind exclusively to IgG's third constant domain (CH3). Other IgG Fc receptors bind to active sites located in both CH2 and CH3 domains and are unable to bind to a single, isolated domain.

After antibodies bind to antigens or are otherwise caused to aggregate, active sites within the Fc region are able to bind to and activate Fc receptors, providing a critical link between antibodies and the rest of the immune system. Fc binding to Fc receptors can thus be characterized as the "final common pathway" by which antibody functions are mediated. If an antigen-bound antibody does not bind to an Fc receptor, the antibody is unable to activate the other portions of the immune system and is therefore rendered functionally inactive.

The Fc region of the immunoglobulin binds to the Fc receptor and the complex can trigger a variety of responses depending on cell type. In the case of macrophages, the response can include phagocytosis and antibody-dependent cell-mediated cytotoxicity (ADCC). Once activated by the binding of antibody Fc region active sites, Fc receptors mediate a variety of important immune killing and regulatory functions. For example, certain IgG Fc receptors mediate direct killing of cells to which the antibody has bound via its Fab arms (i.e., ADCC). Other IgG Fc receptors, when occupied by IgG, stimulate certain white blood cells to engulf and destroy bacteria, viruses, cancer cells or other entities by phagocytosis. Fc receptors on certain types of white blood cells known as B lymphocytes regulate their growth and development into antibody-secreting plasma cells.

Depending upon the particular type of Fc receptor to which an Fc portion of an antibody or active peptide fragment thereof binds, the peptide can either initiate or inhibit immune functions. Initiation can occur if the Fc receptor is of the type that becomes activated by the act of binding to an Fc region or, alternatively, if an Fc active site peptide stimulates the receptor. The type of initiation produced can include, but is not limited to, functions directly or indirectly mediated by antibody Fc region-Fc receptor binding.

The ability to initiate immune system functions, including those listed above, is known to be therapeutically useful in treating diseases such as infectious diseases, conditions in which the immune system is deficient due either to congenital or acquired conditions, cancer, and many other diseases. Such immunostimulation is also useful to boost the body's protective cellular and antibody response to certain injected or orally administered substances administered as vaccines.

As used herein, the term "Fc-mediated mechanism" refers to the initiation of an immune response to foreign antigens, mediated through Fc receptor activation. Fc-mediated mechanisms include, but are not limited to, antibody-dependent cell-mediated cytotoxicity (ADCC) and complement-dependent cytotoxicity (CDC).

In some embodiments, where the humanized TF antibodies disclosed herein can initiate an Fc-mediated mechanism, that mechanism is ADCC. In yet other embodiments, the humanized TF antibodies disclosed herein can initiate CDC.

ADCC is a process by which natural killer cells, T lymphocytes, monocytes/macrophages, and polymorphonuclear neutrophils (effector cells) are triggered to destroy foreign or infectious cells. IgG antibodies must first bind to antigens on the target cell, which sensitizes the cell for recognition by cells that mediate ADCC. Upon encounter with an IgG-sensitized target, IgG Fc receptors on cells that mediate ADCC bind to exposed Fc regions on the surface of the target cell. Such Fc receptor binding activates cells that mediate ADCC to directly lyse the target cell, causing its death. ADCC includes, but is not limited to, stimulation of phagocytosis by certain classes of white blood cells (polymorphonuclear neutrophils, monocytes and macrophages); macrophage activation; natural killer (NK) cell activity; growth and development of B and T lymphocytes and secretion by lymphocytes of lymphokines (molecules with killing or immunoregulatory activities).

CDC is another process by which foreign or infectious agents can be destroyed. An antibody interaction with a foreign antigen, forming an antibody-antigen complex, can result in a conformational change in the Fc region of the antibody. This conformational change may activate complement factor C1, thereby initiating a complement activation cascade involving complement initiation factors C1, C2, C3, and C4. The complement activation cascade terminates in the sequential interaction of C5, C6, C7, C8 and C9 forming the membrane-attack complex (MAC). MAC mediates cell lysis by disrupting the phospholipid membrane of a cell to form large pores in the cell membrane. See, e.g., Reff, M. E. et al. *Blood* 83:435-445 (1994). In this way, the MAC complex is capable of stimulating cell death of a foreign or infectious agent containing an antigen recognized by an antibody of the invention. In addition, C3 and C4 can act as peptide mediators of inflammation, a process that results in localized vasodilation and migration of neutrophils, macrophages and other phagocytic cells. These phagocytic cells can bear Fc receptors, thereby increasing localized antibody-dependent cellular cytotoxicity.

In some embodiments, the humanized TF antibodies disclosed herein contain moderate to high Fc-mediated activity, including, but not limited to, moderate to high ADCC and/or moderate to high CDC activity. A humanized TF antibody, as disclosed herein, has "moderate to high" ADCC activity if at an antibody concentration of 10 µg/ml and effector cell to target cell ratio of 30, at least about 20%, at least about 30%, at least about 40%, at least about 50%, at least about 60%, at least about 70%, at least about 80%, or at least about 90% of target cells are lysed. A humanized TF antibody, as disclosed herein, has "moderate to high" CDC activity if at an antibody concentration of 10 µg/ml and in the presence of undiluted human serum or rabbit serum, at least about 20%, at least about 30%, at least about 40%, at least about 50%, at least about 60%, at least about 70%, at least about 80%, or at least about 90% of target cells are lysed.

Any of the known assays in the art can be used to monitor the Fc-mediated mechanisms of the disclosed humanized TF antibodies. The ability of the antibodies of the present disclosure to initiate one or more Fc-mediated mechanisms can be monitored in vitro or in vivo. For example, CDC activity and ADCC activity of the antibodies can be measured by the methods of Ohta et al., *Cancer Immunol. Immunother.* 36:260 (1993). Other assays include, but are not limited to, a $^{51}$Cr release assay of ADCC and complement-mediated lysis. See *Current Protocols in Immunology*, Coligan, A. M. et al. (Eds.), Wiley & Sons, Inc. (1991), e.g., Unit 7.27; Wang, B. et al., *Proc. Natl. Acad. Sci. USA* 96:1627-1632 (1999); Manches, O. et al., *Blood* 101:949-954 (2003).

Furthermore, Fc-mediated host responses can be monitored in vitro by conventional immunoassays, where the anti-tumor activity of the response can be determined by CDC and/or ADCC assays. The assay methodologies are well known, and are described in Handbook of Experimental Immunology, Vol. 2, Blackwell Scientific Publications, Oxford (1986). In addition, CDC activity and ADCC activity of humanized chimeric antibody to a cultured cancer cell line can be measured in accordance with the procedures disclosed in Menekigaku Jikken Nyumon, (Manual of Immunological Experiments) Matsuhashi et al., Gakkai Shuppan Center, Japan, 1981).

Fc-mediated mechanisms can be monitored in vivo by the development of delayed-type hypersensitivity reactions, or other in vivo or in vitro means known to those skilled in the art (e.g., the skin test reaction protocol, lymphocyte stimulation assays, measuring the toxicity of a subject's lymphocytes to tumor cells by using a standard radioactive release assay, by a limiting dilution assay, or by measuring plasma levels of IL-2 using standard ELISA assays).

Methods of Treatment

The present disclosure also provides a method of treating cancer in a patient, the method comprising administering to a patient in need of such treatment a therapeutically effective amount of a humanized tissue factor antibody or antigen-binding fragment thereof, or antibody-drug conjugate, as disclosed herein. In some embodiments, this antibody-based therapy involves administering the humanized tissue factor antibody or antibody-drug conjugate disclosed herein to an animal, more particularly a mammal, and more particularly a human patient, for treating cancer.

A "therapeutically effective amount" is an amount of a humanized TF antibody or antigen-binding fragment thereof or antibody-drug conjugate that, when administered to a subject or patient for treating a condition, disorder or disease, is sufficient to elicit a cellular response that is clinically significant, without causing an excessive level of adverse side effects. See, "Formulations and Therapeutic Administration" section, infra, for further details.

"Subject" refers to any animal classified as a mammal, including humans, domestic and farm animals, and zoo, sports, and companion animals such as a household pet and other domesticated animal such as, but not limited to, cattle, sheep, ferrets, swine, horses, poultry, rabbits, goats, dogs, cats and the like. In some embodiments, companion animals are dogs and cats. In other embodiments, the subject is a human.

"Patient" refers to a subject, e.g., a human, in need of treatment of a condition, disorder or disease, e.g., cancer.

The terms "treat" and "treatment" refer to both therapeutic treatment and prophylactic or preventative measures, wherein the object is to prevent, inhibit, lessen, or slow the progression of an undesired physiological condition, disorder, or disease, or to obtain one or more beneficial or desired clinical results. For purposes of this invention, beneficial or desired clinical results include, but are not limited to, alleviation of symptoms; diminishment of extent of condition, disorder or disease; stabilized (i.e., not worsening) state of condition, disorder or disease; delay in onset, or slowing, of condition, disorder or disease progression; amelioration of the condition, disorder or disease state, remission (whether partial or total); or enhancement or improvement of condition, disorder or disease. Treatment also includes, but is not limited to, eliciting a cellular response that is clinically significant, without excessive levels of side effects. Treatment also includes, but is not limited to, prolonging survival as compared to expected survival if not receiving treatment.

Therapeutic compounds of the invention include, but are not limited to, humanized TF antibodies or antigen-specific fragments thereof, antibody-drug conjugates, and pharmaceutical compositions, all as disclosed herein. The humanized TF antibodies disclosed herein can be used to treat cancer or disorders or conditions associated with cancer including, but not limited to, any one or more of the diseases, disorders, or conditions described herein. Humanized TF antibodies disclosed herein can be provided in pharmaceutically acceptable compositions as known in the art or as described herein.

The terms "tumor" and "cancer" are used interchangeably, and, along with their grammatical variants, refer to tumors of any cell type, including carcinomas, sarcomas, lymphomas and leukemias of any human and non-human animal species including swine, cats, dogs and higher primates. The methods (and compositions) disclosed herein are suitable for the treatment of solid tumors, which can be characterized by extensive vasculature (microvascularized tumors), including carcinomas, sarcomas and lymphomas of various cell types. Solid tumors targeted by the treatment of the present disclosure include, but are not limited to: cancers of the head and neck, including squamous cell and epidermoid carcinomas; adenocarcinomas, including prostatic, scirrhous, and mammary adenocarcinomas; lymphosarcoma; fibrosarcoma; osteosarcoma; leiomyosarcoma; chondroma; cancer of the prostate, lung, breast, ovary, stomach (gastric), pancreas, larynx, esophagus, testes, liver, parotid, biliary tract, colon, rectum, colorectal, cervix, uterus, endometrium, kidney, bladder, or thyroid; primary tumors and metastases; melanomas; glioblastoma; Kaposi's sarcoma; non-small cell lung cancer (NSCLC), including squamous and adeno types; advanced malignancies; and hematologic malignancies, such as, e.g., leukemias, lymphomas, and myelomas.

In some embodiments, the solid tumor that may be treated by the compositions and methods disclosed herein are solid tumors selected from the group consisting of breast cancer, ovarian cancer, thyroid cancer, colorectal cancer, esophageal cancer, gastric cancer, melanoma, brain cancer, head and neck cancer, epidermal, sarcoma, kidney cancer, pancreatic cancer, prostate cancer, liver cancer, urothelial, and lung cancer.

In some embodiments, the hematological malignancies that may be treated by the compositions and methods disclosed herein are selected from the group consisting of acute lymphocytic leukemia (ALL), acute myeloid leukemia (AML), chronic lymphocytic leukemia (CLL), small lymphocytic lymphoma (SLL), multiple myeloma (MM), Hodgkin's lymphoma (HL), non-Hodgkin's lymphoma (NHL), mantle cell lymphoma (MCL), follicular lymphoma (FL), Waldenstrom's macroglobulinemia (WM), diffuse large B-cell lymphoma (DLBCL), marginal zone lymphoma (MZL), hairy cell leukemia (HCL), Burkitt's lymphoma (BL), and Richter's transformation.

In some embodiments, the cancer cells treated by the methods (or compositions) disclosed herein overexpress human tissue factor. See, e.g., Callander, et al., *Cancer* 70:1194-1201 (1992); Sato et al., *Cancer Sci.* 105:1631-1637 (2014); Zhang et al., *Int. J. Mol. Med.* 29:409-415 (2012); and Cocco et al., *Clin Exp Metastasis* 28:689-700 (2011).

Malignant and metastatic conditions that can be treated with the humanized TF antibodies, ADCs, or pharmaceutical compositions disclosed herein include, but are not limited to, malignancies, solid tumors, and cancers described herein and otherwise known in the art (for a review of such disorders, see Fishman et al., *Medicine*, $2^{nd}$ ed., J.B. Lippincott Co., Philadelphia (1985)). The humanized TF antibodies, as disclosed herein, can be useful in treating other diseases and/or disorders, besides cancers, which involve angiogenesis. These diseases and/or disorders include, but are not limited to, benign tumors, for example hemangiomas, acoustic neuromas, neurofibromas, trachomas, and pyogenic granulomas; artheroscleric plaques; ocular angiogenic diseases, for example, diabetic retinopathy, retinopathy of prematurity, macular degeneration, corneal graft rejection, neovascular glaucoma, retrolental fibroplasia, rubeosis, retinoblastoma, uvietis and Pterygia (abnormal blood vessel growth) of the eye; rheumatoid arthritis; psoriasis; delayed wound healing; endometriosis; vasculogenesis; granulations; hypertrophic scars (keloids); nonunion fractures; scleroderma; trachoma; vascular adhesions; myocardial angiogenesis; coronary collaterals; cerebral collaterals; arteriovenous malformations; ischemic limb angiogenesis; Osler-Webber Syndrome; plaque neovascularization; telangiectasia; hemophiliac joints; angiofibroma; fibromuscular dysplasia; wound granulation; Crohn's disease; and atherosclerosis.

The present disclosure also provides a method of treating metastatic cancer in a patient, the method comprising administering to a patient in need of such treatment a therapeutically effective amount of the humanized tissue factor antibody, antigen-binding fragments thereof, antibody-drug conjugates, or pharmaceutical compositions, as disclosed herein. Treatment of metastases can be shown by the ability of the humanized TF antibodies or antigen-binding fragments thereof, as disclosed herein, to prevent tumor metastases in an animal model. For example, the spontaneous metastases model and the pulmonary metastases tumor model are metastases models known in the art. In the spontaneous metastases tumor model, an animal is subcutaneously injected with tumor cells which form a primary tumor mass. Subsequently, some of the cells of the tumor spontaneously migrate to other parts of the animal, including the lung. See Zisman, A. et al., *Cancer Research* 63:4952-59 (2003); Lev, D. C. et al., *Clin. Exp. Metas.* 20:515-23 (2003). In the pulmonary metastases tumor model, a suspension of tumor cells is injected into the tail vein of a mouse and the formation of metastases in the lungs of the recipient animal is evaluated. See Tian F. et al, *Cancer Research* 63:8284-92 (2003); Ogawa, K. et al., *Int. J. Cancer* 91:797-802 (2001). In these models, an antibody that is effective in the treatment of metastases will, upon its administration to the recipient animal, either prevent metastases from occurring or reduce the number of metastases that form as compared to the number of metastases formed in a recipient animal given a negative control.

The humanized TF antibody or antigen-binding fragment thereof, ADC, or pharmaceutical composition, as disclosed herein, can be used to treat hyperproliferative diseases, disorders, and/or conditions, including neoplasms. The antibody can inhibit proliferation of the disorder through direct or indirect interactions. For example, by increasing an immune response, particularly increasing antigenic qualities of the hyperproliferative disorder or by proliferating, differentiating, or mobilizing T-cells, hyperproliferative diseases, disorders, and/or conditions can be treated, and/or diagnosed. This immune response can be increased by either enhancing an existing immune response, or by initiating a new immune response.

Examples of hyperproliferative diseases, disorders, and/or conditions that can be treated, and/or diagnosed by the disclosed TF antibodies, include, but are not limited to, neoplasms located in the colon, lung, abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic, and urogenital systems.

Similarly, other hyperproliferative diseases, disorders, and/or conditions can be treated and/or diagnosed by the humanized TF antibodies of the invention. Examples of such hyperproliferative diseases, disorders, and/or conditions include, but are not limited to, hypergammaglobulinemia, lymphoproliferative diseases, disorders, and/or conditions, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

The present disclosure also provides for the treatment of diseases, disorders, and/or conditions associated with neovascularization by administration of the disclosed humanized TF antibodies or antigen-binding fragments thereof. The naturally occurring balance between endogenous stimulators and inhibitors of angiogenesis is one in which inhibitory influences predominate. Rastinejad et al., *Cell* 56:345-355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormal neovascularization including solid tumor growth and metastases, arthritis, some types of eye diseases, disorders and/or conditions, and psoriasis. See, e.g., Moses et al., *Biotech.* 9:630-634 (1991); Folkman et al., *N. Engl. J. Med.*, 333:1757-1763 (1995); Auerbach et al., *J. Microvasc. Res.* 29:401-411 (1985); Folkman, Advances in Cancer Research, eds. Klein and Weinhouse, Academic Press, New York (1985), pp. 175-203; Patz, *Am. J. Opthalmol.* 94:715-743 (1982); and Folkman et al., *Science* 221: 719-725 (1983). In a number of pathological conditions, the process of angiogenesis contributes to the disease state. For example, significant data has been accumulated suggesting that the growth of solid tumors is dependent on angiogenesis. Folkman and Klagsbrun, *Science* 235:442-447 (1987).

Additional ways in which the humanized tissue factor antibodies or antigen-binding fragments thereof, as disclosed herein, can be used therapeutically include, but are not limited to, directed cytotoxicity of the antibody, e.g., as mediated by complement (CDC) or by effector cells (ADCC), or indirect cytotoxicity of the antibody, e.g., as ADCs.

The humanized tissue factor antibodies or antigen-binding fragments thereof disclosed herein can also be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies, or as conjugated to a cytotoxic agent such as a radioisotope or other cytotoxic agent, as described above.

The humanized tissue factor antibodies or antigen-binding fragments thereof disclosed herein can be administered alone or in combination with other types of treatments (e.g., radiation therapy, chemotherapy, hormonal therapy, immunotherapy, anti-tumor agents, and anti-retroviral agents).

Formulations and Therapeutic Administration

The present disclosure provides methods of treatment by administering to a subject in need thereof an effective amount of a humanized TF antibody or antigen-binding fragment thereof, an ADC, or a pharmaceutical composition, all as disclosed herein. In some embodiments, the humanized TF antibody is substantially purified. In some embodiments, the humanized TF antibody is conjugated to a cytotoxic agent (e.g., as an ADC). Formulations and methods of administration are described herein.

Various delivery systems are known in the art and can be used to administer the humanized TF antibody or antigen-binding fragment thereof, ADC, or pharmaceutical composition, as disclosed herein, e.g., encapsulation in liposomes, microparticles, microcapsules, recombinant cells capable of expressing the compound, receptor-mediated endocytosis (see, e.g., Wu and Wu, *J. Biol. Chem.* 262:4429-4432 (1987)), construction of a nucleic acid as part of a retroviral or other vector, etc. Modes of administration include intradermal, intramuscular, intraperitoneal, intravenous, subcutaneous, intranasal, epidural, and oral routes. Administration can be by any convenient route, for example, by infusion or bolus injection, or by absorption through epithelial or mucocutaneous linings (e.g., oral mucosa, rectal and intestinal mucosa, etc.). Administration can be systemic or local. In addition, it can be desirable to introduce the humanized TF antibody or antigen-binding fragment thereof, ADC, or pharmaceutical composition, as disclosed herein, into the central nervous system by any suitable route, including intraventricular and intrathecal injection; intraventricular injection can be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In some embodiments, it can be desirable to administer the humanized TF antibody or antigen-binding fragment thereof, ADC, or pharmaceutical composition, as disclosed herein, locally to the area in need of treatment; this can be achieved, for example, by local infusion during surgery, topical application, e.g., in conjunction with a wound dressing after surgery, by injection, by means of a catheter, by means of a suppository, or by means of an implant, the implant being of a porous, non-porous, or gelatinous material, including membranes, such as sialastic membranes, or fibers. When administering a protein, including an antibody, care must be taken to use materials to which the protein does not adsorb.

In other embodiments, the humanized TF antibody or ADC, as disclosed herein, can be delivered in a vesicle, in particular, a liposome (see, Langer, *Science* 249:1527-1533 (1990); Treat et al., in *Liposomes in the Therapy of Infectious Disease and Cancer*, Lopez-Berestein and Fidler, eds., Liss, New York (1989), pp. 353-365; Lopez-Berestein, ibid., pp. 317-327; see generally ibid.)

In yet other embodiments, the humanized TF antibody or ADC, as disclosed herein, can be delivered in a controlled release system. In some embodiments, a pump can be used (see Langer, supra; Sefton, *CRC Crit. Ref. Biomed. Eng.* 14:201 (1987); Buchwald et al., *Surgery* 88:507 (1980); Saudek et al., *N. Engl. J. Med.* 321:574 (1989)). In other embodiments, polymeric materials can be used (see *Medical Applications of Controlled Release*, Langer and Wise, eds., CRC Pres., Boca Raton, Fla. (1974); *Controlled Drug Bioavailability, Drug Product Design and Performance*, Smolen and Ball, eds., Wiley, New York (1984); Ranger and Peppas, *J., Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)). In yet other embodiments, a controlled release system can be placed in proximity of the therapeutic target, i.e., the brain, thus requiring only a fraction of the systemic dose (see, e.g., Goodson, in *Medical Applications of Controlled Release*, supra, vol. 2, pp. 115-138 (1984)). Other controlled release systems are discussed in Langer, supra.

The present disclosure also provides pharmaceutical compositions. Such pharmaceutical compositions comprise a therapeutically effective amount of a humanized TF antibody or ADC, as disclosed herein, and a pharmaceutically acceptable carrier. In some embodiments, the term "pharmaceutically acceptable" indicates that the substance or composition must be compatible chemically and/or toxicologically, with the other ingredients comprising a formulation, and/or the mammal being treated therewith.

The term "carrier" refers to a diluent, adjuvant, excipient, or vehicle with which the therapeutic is administered. Such pharmaceutical carriers can be sterile liquids, such as water and oils, including those of petroleum, animal, vegetable, or synthetic origin, such as peanut oil, soybean oil, mineral oil, sesame oil and the like. In some embodiments, water can be used as a carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The pharmaceutical composition, if desired, can also contain minor amounts of wetting or emulsifying agents, or pH buffering agents.

The pharmaceutical compositions can take the form of solutions, suspensions, emulsions, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in *Remington's Pharmaceutical Sciences* by E. W. Martin. Such compositions will contain a therapeutically effective amount of the compound, preferably in purified form, together with a suitable amount of carrier so as to provide the form for proper administration to the patient. The formulation should suit the mode of administration.

In some embodiments, the composition is formulated in accordance with routine procedures as a pharmaceutical composition adapted for intravenous administration to humans. Typically, compositions for intravenous administration are solutions in sterile isotonic aqueous buffer. Where necessary, the composition can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

A therapeutically effective amount of a humanized TF antibody, an antigen-binding fragment thereof, pharmaceutical composition, or an ADC, as disclosed herein, which will be therapeutically effective in the treatment of a disorder, e.g., cancer, can be determined by standard clinical techniques. In addition, in vitro assays can optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses can be extrapolated from dose-response curves derived from in vitro or animal model test systems.

For humanized antibodies, the dosage administered to a patient is typically 0.1 mg/kg to 100 mg/kg of the patient's body weight. However, for radiolabeled antibodies, the dosage administered can be lower, e.g., 0.01 mg/kg to 1 mg/kg of the patient's body weight, and for toxin-immunoconjugates, the dosage administered can be even lower, e.g., 0.001 mg/kg of the patient's body weight. In some embodiments, the dosage administered to a patient is between 0.001 mg/kg and 100 mg/kg of the patient's body weight. In other embodiments, the dosage administered to a patient is between 0.01 mg/kg and 50 mg/kg of the patient's body weight. In other embodiments, the dosage administered to a patient is between 0.1 mg/kg and 20 mg/kg of the patient's body weight. In yet other embodiments, the dosage administered to a patient is between 1 mg/kg to 10 mg/kg of the patient's body weight.

Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention can be reduced by enhancing uptake and tissue penetration (e.g., into the brain) of the antibodies by modifications such as, for example, lipidation.

All of the various embodiments or options described herein can be combined in any and all variations.

Detection and Diagnostic Uses

A humanized TF antibody or antigen-binding fragment thereof, as described herein, can be used to assay TF protein levels in a biological sample using classical methods known to those of skill in the art, including immunoassays, such as the enzyme linked immunosorbent assay (ELISA), immunoprecipitation, or Western blotting. Suitable antibody assay labels are known in the art and include enzyme labels, such as, glucose oxidase; radioisotopes, such as iodine ($^{125}$I, $^{121}$I) carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin. Such labels can be used to label an antibody or antigen-binding fragment thereof described herein. Alternatively, a second antibody or antigen-binding fragment thereof that recognizes an anti-TF antibody or antigen-binding fragment thereof described herein can be labeled and used in combination with an anti-TF antibody or antigen-binding fragment thereof to detect TF protein levels.

Assaying for the expression level of TF protein is intended to include qualitatively or quantitatively measuring or estimating the level of a TF protein in a first biological sample either directly (e.g., by determining or estimating absolute protein level) or relatively (e.g., by comparing to the disease associated protein level in a second biological sample). TF polypeptide expression level in the first biological sample can be measured or estimated and compared to a standard TF protein level, the standard being taken from a second biological sample obtained from an individual not having the disorder or being determined by averaging levels from a population of individuals not having the disorder. As will be appreciated in the art, once the "standard" TF polypeptide level is known, it can be used repeatedly as a standard for comparison.

As used herein, the term "biological sample" refers to any biological sample obtained from a subject, cell line, tissue, or other source of cells potentially expressing TF. Methods for obtaining tissue biopsies and body fluids from animals (e.g., humans) are well known in the art. Biological samples include peripheral mononuclear blood cells. A biological sample may also be a blood sample, in which circulating tumor cells (or "CTCs") may express TF and be detected.

The humanized TF antibodies described herein can be used for prognostic, diagnostic, monitoring, and screening applications, including in vitro and in vivo applications well known to the skilled artisan and based on the present description. Prognostic, diagnostic, monitoring, and screening assays and kits for in vitro assessment and evaluation of immune system status and/or immune response may be utilized to predict, diagnose and monitor to evaluate patient samples including those known to have or suspected of having an immune system-dysfunction or cancer. This type of prognostic and diagnostic monitoring and assessment is already in practice utilizing antibodies against the HER2 protein in breast cancer (HercepTest™, Dako) where the assay is also used to evaluate patients for antibody therapy using Herceptin®. In vivo applications include directed cell therapy and immune system modulation and radio imaging of immune responses.

In some embodiments, the humanized TF antibodies and antigen-binding fragments thereof described herein can carry a detectable or functional label. When fluorescence labels are used, currently available microscopy and fluorescence-activated cell sorter analysis (FACS) or a combination of both methods or other procedures known in the art may be utilized to identify and quantitate the specific binding members. The humanized TF antibodies and antigen-binding fragments thereof described herein can carry a fluorescence label. Exemplary fluorescence labels include, for example, reactive and conjugated probes, e.g., Aminocoumarin, Fluorescein and Texas red, Alexa Fluor dyes, Cy dyes and DyLight dyes. An anti-TF antibody can carry a radioactive label, such as the isotopes $^{3}$H, $^{14}$C, $^{32}$P, $^{35}$S, $^{36}$Cl, $^{51}$Cr, $^{57}$Co, $^{58}$Co, $^{59}$Fe, $^{67}$Cu, $^{90}$Y, $^{99}$Tc, $^{111}$In, $^{117}$Lu, $^{121}$I, $^{124}$I, $^{125}$I, $^{131}$I, $^{198}$Au, $^{211}$At, $^{213}$Bi, $^{225}$Ac and $^{186}$Re. When radioactive labels are used, currently available counting procedures known in the art may be utilized to identify and quantitate the specific binding of anti-TF antibody or antigen-binding fragment thereof to TF (e.g., human TF). In the instance where the label is an enzyme, detection may be accomplished by any of the presently utilized colorimetric, spectrophotometric, fluorospectrophotometric, amperometric or gasometric techniques as known in the art. This can be achieved by contacting a sample or a control sample with a humanized TF antibody or antigen-binding fragment thereof under conditions that allow for the formation of a complex between the antibody or antigen-binding fragment thereof and TF. Any complexes formed between the antibody or antigen-binding fragment thereof and TF are detected and compared in the sample and the control. In light of the specific binding of the antibodies or antigen-binding fragments thereof described herein for TF, the antibodies or antigen-binding fragments thereof can be used to specifically detect TF expression on the surface of cells. The antibodies or antigen-binding fragments thereof described herein can also be used to purify TF via immunoaffinity purification.

Also included herein is an assay system which may be prepared in the form of a test kit for the quantitative analysis of the extent of the presence of, for instance, TF. The system or test kit may comprise a labeled component, e.g., a labeled antibody or antigen-binding fragment thereof, and one or more additional immunochemical reagents In some aspects, methods for in vitro detecting of TF in a sample, comprising contacting said sample with an antibody or antigen-binding fragment thereof, are provided herein. In some aspects, provided herein is the use of an antibody or antigen-binding fragment thereof provided herein, for in vitro detecting of TF in a sample. In one aspect, provided herein is an antibody or antigen-binding fragment thereof or pharmaceutical composition provided herein for use in the detection of TF in a subject or a sample obtained from a subject. In one aspect, provided herein is an antibody or antigen-binding fragment thereof or pharmaceutical composition provided herein for use as a diagnostic. In some embodiments, the antibody comprises a detectable label. In a preferred embodiment, TF is human TF and the subject is a human.

The following examples are illustrative of the present disclosure, but are not to be construed as further limiting.

EXAMPLES

Methods of producing the parent murine TF antibody ("the TF278 antibody") and assessment of its activities are described in U.S. Pat. No. 7,993,644, which is herein incorporated by reference in its entirety. The assays in Examples 1-8 were carried out in an effort to identify suitable humanized variants of the murine TF278 antibody. The identified humanized variants are named as B278-LC_HC_, wherein the different LC variable regions and HC variable regions are assigned a number and a unique SEQ ID NO. For example, humanized variant B278-LC7HC6 comprises the light chain variable region 7 (SEQ ID NO: 12) and the heavy chain variable region 6 (SEQ ID NO: 9).

Example 1: Expression of Humanized Anti-TF Antibody Variants

I. Antibody Humanization

The variable region as derived from murine parent sequences were used to generate full length humanized antibody designs. Variable chains were humanized by grafting the CDR sequences onto suitable human antibody donor sequences as previously described (EP 239,400; PCT publication WO 91/09967; U.S. Pat. Nos. 5,225,539; 5,530,101; and 5,585,089, each of which is incorporated by reference in its entirety). The full length humanized antibodies were created using the constant domain of the suitable human antibody donor sequences.

Fusion Antibodies (UK) used the DNAstar NovaFold Protein Structure Prediction Software to provide 3D structural predictions of the humanized antibodies and to select the best human donor sequences. DNASTAR NovaFold is protein structure prediction software that is based on I-Tasser, the software package developed at the University of Michigan. NovaFold utilizes the I-Tasser algorithms that combine threading and ab initio folding technologies to build accurate, full 3D atomic models of proteins with previously unknown structures.

At least four variants were made for each variable chain using different human donor sequences. This produced a matrix of at least 16 humanized antibodies for expression.

DNA sequences encoding the antibody variants were synthesized and then subcloned into mammalian expression vectors. Antibody variants were expressed transiently in CHO cells, purified, and tested in the assays as described.

II. Transient Transfection of CHO Cells

Suspension adapted CHO cells (Thermo Fisher, UK) were routinely cultivated at $2.0-3.0\times10^5$ cells/ml at 150 rpm, 8% CO2, 37° C. in Pro CHO4 serum free medium (Lonza, Belgium) supplemented with 8 mM L-glutamine (Thermo Fisher, UK) and Hypoxanthine/Thimidine (10 ml per litre, Invitrogen, UK) in 500 ml vented Erlenmeyer flasks (Corning, Netherlands). Maxipreps of each construct were prepared using a Purelink HiPure Plasmid Maxiprep kit (Thermo Fisher, UK) as per the manufacturer's instructions. Vector DNA was quantified using a Nano Drop lite spectrophometer, as per the manufacturer's instructions.

CHO-S cells at a final density of $1.0\times10^6$ cells/ml were transiently transfected with 1.25 µg/ml of plasmid DNA in Pro CH05 serum free medium (Lonza, Belgium) supplemented with 8 mM L-glutamine (Thermo Fisher, UK) and Hypoxanthine/Thimidine (10 ml per litre, Thermo Fisher, UK) in 500 ml vented Erlenmeyer flasks (Corning, Netherlands). Transfected cultures were incubated for 7-9 days at 37° C., 8% $CO_2$ and 135 rpm, before harvesting by centrifugation at 4000 rpm, 4° C. for 40 minutes.

III. Purification of Humanized B278 Antibodies

Following centrifugation, all media was filtered through a 0.8 µM cellulose acetate filter. Each batch was purified using an Amersham Biosciences AKTA Chromatography system. A 1 ml HiTrap Protein A column was used for all humanized antibody purifications. All purifications were carried out using Fusion Antibodies in-house wash and elution buffers.

Following loading on the Protein A column, any bound antibody was eluted using a Glycine/Tris pH 3.0 buffer. All eluted 1 ml fractions were neutralized with 100 µl Tris pH 8.5 buffer. Eluted fractions corresponding to elution peak were selected for overnight dialysis in PBS.

IV. Determination of Protein Concentration Using a BCA Assay

A bicinchoninic acid assay (BCA) was carried out using a Micro BCA protein assay kit (Thermo Scientific, UK), as per the manufacturer's instructions, and the results read at 570 nm on a Tecan plate reader. Table 4 shows the expression yields for the indicated humanized TF antibody variants. Results from the BCA assay showed that four of the B278 variants tested produced suitable levels (>1 mg/ml) of the variant TF antibodies (LC3HC5, LC5HC6, LC7HC4, and LC7HC6).

TABLE 4

Summary of expression yields of the humanized B278 variant antibodies

| Variant | Volume Transfected | Vol (ml) | Conc (mg/ml) | Yield (mg) | Comments |
|---|---|---|---|---|---|
| LC0 HC0 | 200 ml | 2.0 | 1.915 | 3.83 | |
| LC3 HC5 | 200 ml | 3.0 | 1.665 | 5.0 | |
| LC3 HC6 | 100 ml | 2.4 | 0.568 | 1.36 | |
| LC5 HC4 | 200 ml | 2.0 | 0.696 | 1.39 | |
| LC5 HC5 | 100 ml | 1.5 | 0.774 | 1.16 | |
| LC5 HC6 | 200 ml | 3.1 | 3.687 | 11.3 | |
| LC6 HC4 | 100 ml | N/A | N/A | N/A | No peak repeat |
| LC6HC4 #2 | 200 ml | 1.2 | 0.265 | 0.318 | |
| LC6 HC5 | 100 ml | 2.4 | 0.079 | 0.19 | |
| LC6 HC6 | 100 ml | 2.5 | 0.268 | 0.67 | |
| LC7 HC4 | 200 ml | 2.0 | 0.748 | 1.496 | |
| LC7 HC4#2 | 600 ml | 2.5 | 1.974 | 4.935 | |
| LC7 HC5 | 100 ml | 2.0 | 2.11 | 4.22 | |
| LC7 HC6 | 100 ml | 1.4 | 0.776 | 1.09 | |
| LC7 HC6 #2 | 500 ml | 3.0 | 5.097 | 15.29 | |
| LC8 HC4 | 200 ml | N/A | N/A | N/A | No peak repeat |
| LC8 HC4 #2 | 200 ml | 2.4 | 0.139 | 0.333 | |
| LC8 HC5 | 100 ml | 2.1 | 0.63 | 1.32 | |
| LC8 HC6 | 100 ml | 1.6 | 0.178 | 0.28 | |

Example 2: SDS-PAGE Analyses of Humanized B278 Variants

Purified humanized B278 antibodies were analyzed by both reducing SDS-PAGE (4-20% acrylamide gel) and non-reducing SDS-PAGE (4-20% acrylamide gel).

Reducing SDS-PAGE Sample Preparation.

For reducing SDS-PAGE, the samples of purified antibody were heated to 95° C. for 10 minutes in 5× treatment buffer (250 mM Tris HCl pH 6.8, 10% SDS, 30% Glycerol, 0.5M dithiothreitol, and 0.02% bromophenol blue).

Non-Reducing SDS-PAGE Sample Preparation.

For non-reducing SDS-PAGE, the samples of purified antibody were diluted in 5× treatment buffer devoid of reducing agent (dithiothreitol) and heated for 10 minutes at 70° C.

Methods.

Samples (5 µg) were loaded onto 4-20% SDS-polyacrylamide gels and ran at 200 Volt for 65 minutes. Bands were visualized by staining with quick Coomassie stain (Generon; GEN-QC-STAIN-1L), as per manufacturer's instruction. Protein ladders on the gels were from SeeBlue Plus 2 pre-stained protein standard (Invitrogen, CA, Cat. No. LC5925).

Staining and destaining of gels: Following SDS PAGE, gels were stained overnight in Comassie Brilliant blue stain (Coomassie brilliant blue 0.1% (w/v), Methanol 50% (v/v), Acetic Acid 10% (v/v) and pure water 50% (v/v)). Gels were destained in destain solution (Methanol 10% (v/v), Acetic Acid 10% (v/v) and pure water 80% (v/v)) until the protein bands were clearly visible. Bands were visualized on a lightbox and imaged using a Gel logic 1500 gel imaging system using Care Stream MI imaging software.

Results.

Representative reducing and non-reducing SDS-PAGE results are shown in FIGS. 6 and 7, respectively. The sample loaded in each lane is as follows: Lane 1: SeeBlue plus 2 (Invitrogen, CA), Lane 2: B278-LC3HC5 variant, Lane 3: B278-LC3HC6 variant, Lane 4: B278-LC5HC4 variant, Lane 5: B278-LC5HC5 variant, Lane 6: B278-LC5HC6 variant, Lane 7: B278-LC6HC4 variant #2, Lane 8: B278-LC6HC5 variant, Lane 9: B278-LC6HC6 variant, Lane 10: B278-LC7HC4 variant, Lane 11: B278-LC7HC4 variant #2, Lane 12: B278-LC7HC5 variant, Lane 13: B278-LC7HC6 variant, Lane 14: B278-LC7HC6 variant #2, Lane 15: B278-LC8HC4 variant #2, Lane 16: B278-LC8HC5 variant, Lane 17: B278-LC8HC6 variant, Lane 18: SeeBlue plus 2 (Invitrogen).

Conclusions.

Results from the reducing SDS-PAGE indicate that the predominant bands detected for all of the humanized variants of B278 are the individual heavy and light chains. Results from the non-reducing SDS-PAGE indicate that the main protein band detected in all of the humanized variants of B278 is the intact antibody migrating at approximately 148 kDaltons.

Example 3: ELISA Analysis for Binding of Humanized B278 Variants to Recombinant Human Coagulation Factor III (Tissue Factor)

The binding of humanized variants of TF antibody B278, including B278-LC7HC4, LC7HC5, LC7HC6, LC8HC4, LC8HC5, and LC8HC6 variants, to recombinant human coagulation factor III (tissue factor) was assessed by ELISA analysis. The chimeric antibody B278-LC0HC0 was used as a control. In brief, 100 ng/well of Recombinant Human Coagulation Factor III (R&D Systems, UK) was immobilized onto 96 well Maxisorp plates in coating buffer (0.5 mM NaHCO$_3$ brought to pH 9.5 by the addition of 0.5 mM Na$_2$CO$_3$) overnight at 4° C. Coating buffer was removed and the plates were washed once in PBS Tween (PBS-T) (0.05% (v/v) Tween 20). 200 µl per well of 3.0% (w/v) semi skim milk in PBS was added and the plates were agitated for 2 hours at room temperature. Plates were washed three times with PBS-T.

Purified humanized variants of the TF antibody B278 (LC7HC4; LC7HC5; LC7HC6; LC8HC4; LC8HC5; LC8HC6) were serially diluted from 1,000 ng/ml to 0.97 ng/ml in incubation buffer (PBS, 1% (w/v) BSA), and 100 µl added per well.

Following agitation for two hours at room temperature, the plate was washed three times with PBS-T. 100 µl/well of goat anti-human HRP (Fc specific) (Sigma, UK) (1:60,000 PBS) was added and plates incubated for one hour with agitation at room temperature. The plates were washed three times with PBS-T and once in PBS. 100 µl/well of 3,3',5, 5'-Tetramethylbenzidine (TMB) substrate solution was added and incubated at 37° C. for 10 minutes. 50 µl of 1M HCl were added per well and the plates immediately read at 450 nm on a Tecan Sunrise plate reader. An exemplary result is demonstrated in FIG. 8.

Conclusion.

Three of the six variants tested bound with a similar EC$_{50}$ as the chimeric LC0HC0 B278 antibody.

Example 4: Size Exclusion Chromatography (SEC) Analysis

Sample Preparation.

All samples were diluted to a final concentration of 1 mg/mL using Phosphate Buffered Saline (PBS), pH 7.4.

SEC-HPLC.

The separation of the samples was performed using SEC-HPLC with UV detection at 280 nm. Separation was performed on a Waters® ACQUITY H-ClassBio instrument using a TSKgel® G3000SWXL 5 µm 7.8×300 mm column at ambient temperature (AT). As eluent, 0.165 M sodium phosphate at pH 6.5 was used for isocratic elution. A flow rate of 0.6 mL/min. was applied and a sample volume of 50 µL was loaded onto the analytical column.

Data Analysis.

Data generation, presentation, and evaluation were performed using a Waters® ACQUITY H-ClassBio instrument and Empower3™ software modules.

Results.

The sample B278-LC7HC6 variant (PS-F09-2016-012) was analyzed and chromatograms of good quality obtained. The chromatograms show one main peak and one higher molecular weight species. The results are shown in FIGS. 9A and 9B (replicates of the B278-LC7HC6 variant). The integration results of sample B278-LC7HC6 (PS-F09-2016-012) are shown in Table 5 below.

Conclusion.

Results from the SEC-HPLC analysis show that the B278-LC7 HC6 variant is very homogeneous with only a very small amount of aggregate present in the preparation.

TABLE 5

Integration results of sample B278-LC7HC6

| Peak [#] | Replicate [#] | RT [min] | Relative Peak area [%] |
|---|---|---|---|
| 1 | 1 | 12.78 | 0.63 |
|   | 2 | 12.79 | 0.71 |
| 2 | 1 | 15.18 | 99.37 |
|   | 2 | 15.15 | 99.29 |

Example 5: Hydrophobic Interaction Chromatography (HIC) Analysis

Sample Preparation.

All samples were diluted to a final concentration of 1 mg/mL using Phosphate Buffered Saline pH 7.4.

HIC Analysis.

The separation of the samples was performed using HIC with UV detection at 280 nm. Separation was performed on a Shimadzu® Prominence instrument. The separation was performed on a TSKgel® Butyl-NPR 2.5 µm 4.6×35 mm column at ambient temperature (AT). As eluents, A: 1.5 M ammonium sulfate, 25 mM sodium phosphate, pH 6.95 and B: 25 mM sodium phosphate, pH 6.95, 20% isopropyl alcohol, were applied at a binary gradient from 0-100% B in 20 minutes with a flow rate of 0.4 mL/min. A volume of 20 µL of a 1 mg/mL solution was injected onto the analytical column.

Data Analysis.

Data generation, presentation, and evaluation were performed using a Waters® ACQUITY H-ClassBio instrument and Empower3™ software modules.

Results.

The sample B278-LC7HC6 was analyzed and chromatograms of good quality were obtained. The chromatograms show one main peak and one minor signal. Chromatograms are shown in FIGS. 10A and 10B (duplicates) and integration results are shown in Table 6.

TABLE 6

Integration results of sample B278-LC7HC6

| Peak [#] | Replicate [#] | RT [min] | Relative Peak area [%] |
|---|---|---|---|
| 1 | 1 | 10.61 | 0.69 |
|   | 2 | 10.61 | 0.63 |
| 2 | 1 | 11.22 | 99.31 |
|   | 2 | 11.24 | 99.37 |

Example 6: Biacore™/SPR Binding

Biacore™ Analysis of Anti-hTF MAbs.

Binding properties of anti-hTF MAbs were evaluated using a Biacore X (Biacore Inc., Uppsala, Sweden). Briefly, a CM5 Biacore biosensor chip was docked into the instrument and activated with 55 µL of 1:1 NHS/EDC reagent (Biacore Inc.) at room temperature. The recombinant soluble hTF and BSA (10 µg/mL in 0.05 M acetate buffer, pH 4.5) were immobilized on the activated chip in flow cells 1 and 2, respectively. Immobilization was carried out at a flow rate of 5 µL/min until a resonance response of 1000-2000 RU was achieved. The chip was then blocked by injection of 55 µL of ethanolamine-HCl, pH 8.5, followed by five washes with 50 mM NaOH, 1 M NaCl.

To measure the binding of anti-hTF MAbs to the soluble hTF immobilized to the chip, 30 µL of anti-hTF MAbs at varying concentrations in Biacore running buffer (HBS-EP, Biacore Inc.) were injected over the sensor surface at a flow rate of 5 µL/min. Following completion of the injection phase, dissociation was monitored in BIAcore running buffer at the same flow rate for 360 sec. The surface was regenerated between injections using 30 µL of 50 mM NaOH-1 M NaCl. Individual sensorgrams were analyzed using BIAsimulation software. Results for the Biacore/SPR binding analyses are shown in FIGS. 11A and 11B and Table 7. The data shows that the humanized B278-LC7HC6 variant and the chimeric B278 control antibody LC0HC0 are equivalent in binding to hTF.

TABLE 7

Biacore ™/SPR binding analyses of the B278-LC7HC6 variant and chimeric control

| | Kinetic global fit (Langmuir 1:1) | | |
|---|---|---|---|
| | $k_a$ (M$^{-1}$s$^{-1}$) | $k_d$ (s$^{-1}$) | $K_D$ (M) |
| Ab LC7HC6 | $2.8 \times 10^4$ | $7.0 \times 10^{-4}$ | $25.3 \times 10^{-9}$ |
| Ab LC0HC0 (chimeric B278) | $4.3 \times 10^4$ | $1.1 \times 10^{-3}$ | $24.9 \times 10^{-9}$ |

Example 7: Nano Differential Scanning Calorimetry (DSC) to Assess Conformational Stability Sample Preparation.

The concentration was adjusted to 2 mg/mL with formulation buffer for all samples.

Nano-DSC Analysis.

Analysis was performed on a NanoDSC microcalorimeter (TA Instruments, DE). Thermograms were recorded from 20 to 100° C. at a scan speed of 1° C./minute with the DSCrun software (TA Instruments, DE). Buffer thermograms were recorded in parallel and subtracted from the sample thermograms.

Data Analysis.

Data analysis was performed with the NanoAnalyze software (TA Instruments, DE) using two-state fitting models. An exemplary nano-DSC thermogram (first replicate) and fitting of sample B278-LC7HC6 variant is shown in FIG. 12. A summary of the DSC results is shown in Table 8.

Conclusion.

The thermogram of the B278-LC7HC6 sample shows a high enthalpy transition at 68.4 degrees Centigrade and two smaller signals between 76.3 and 82.7 degrees Centigrade, which are typical for an IgG1 monoclonal antibody.

TABLE 8

Summary of the DSC results

| Sample | $T_m$ [° C.] | | ΔH [kJ/mol] | |
|---|---|---|---|---|
| | R1 | R2 | R1 | R2 |
| B278-LC7HC6 | 68.4 | 68.3 | 634 | 681 |
| | 78.0 | 76.3 | 474 | 360 |
| | 82.7 | 81.1 | 913 | 537 |

Example 8: Inhibition of Tissue Factor Mediated Blood Coagulation

The activation of Factor X, a surrogate marker for tissue factor-mediated blood coagulation, is measured by using a modified protocol for Abcam's Tissue factor Human Chromogenic Activity Assay Kit (#Ab 108906). Assay kit constituents were prepared as per the Abcam kit manual, with test samples diluted to 20, 4, 0.8, and 0.032 μg/ml with assay diluent. TF Standard (kit constituent) was made up to a 200 pM concentration as per the kit instructions.

Purified B278-LC7HC6 variant subclones 2N2, 1L6, and 5D6, control antibodies, including the chimeric version LC0HC0, ADG4507 (Sekisui Diagnostics), and ADG4508 (Sekisui Diagnostics), were pre-incubated in a 1:1 ratio with TF Standard to give final concentrations 10, 2, 0.4, and 0.016 μg/ml of test antibodies and 100 pM TF standard.

10 μl of test solutions were transferred to the assay plate, with 70 μl of assay mix (50 μl assay diluent, 10 μl FVII, 10 μl FX) as per assay instructions. Each test condition was performed in duplicate on the assay plate. After incubation at 37° C. for 30 minutes, FXa substrate (20 μl/well) was added, incubated for 20 minutes and read at 405 nm on a fluorescence plate reader. Exemplary results of the assay are shown in FIG. 13. The Absorbance at 405 nm shown is a read out of cleavage of the chromogenic substrate of FXa which only occurs after tissue factor mediated activation of Factor VII, which then activates FX to FXa.

Conclusion.

As previously shown with the murine form of the B278 antibody, the chimeric (LC0HC0) and 3 subclones of the LC7HC6 variant do not inhibit TF-mediated initiation of the extrinsic pathway of blood coagulation whereas the two control antibodies (ADG4507 and ADG4508) show significant inhibition of Factor X activation.

Example 9: Assays for Identifying ADCs Using the Disclosed Humanized Tissue Factor Antibodies One or more of the following assays known to those skilled in the art are carried out in an effort to identify suitable linker-drug combinations to be used in ADC constructs with the humanized B278 TF antibodies disclosed herein. These assays are listed below and several are described further in subsequent Examples:

Measure binding of ADC to cancer cell lines using FACS;
Measure inhibition of proliferation of cancer cells expressing TF;
Size Exclusion Chromatography (SEC) to assess homogeneity and level of aggregation of the ADC;
Liquid Chromatography/Mass Spectroscopy (LC/MS) to measure the drug-antibody ratio (DAR);
Anti-tumor activity in human xenograft tumor models;
Anti-tumor activity in Patient Derived Xenograft (PDX) tumor models;
Pharmacokinetics;
Toxicology; and
Inhibition of tissue factor mediated blood coagulation.

Example 10: SEC-HPLC to Assess Homogeneity and Level of Aggregation of the ADC Methods similar to those described in Example 4 can also be used to assess the homogeneity and extent of aggregation of the ADC.

Example 11: Anti-Tumor Activity in Human Xenograft Tumor Models

Cell Culture Conditions.

Tumor cells are grown as a monolayer at 37° C. in a humidified atmosphere (5% $CO_2$, 95% air). The culture medium is RPMI 1640 containing 2 mM L-glutamine (ref: BE12-702F, Lonza, Verviers, Belgium) supplemented with 10% fetal bovine serum (ref: 3302, Lonza). FaDu tumor cells are adherent to plastic flasks. For experimental use, tumor cells are detached from the culture flask by a 5-minute treatment with trypsin-versene (ref: BE02-007E, Lonza), in Hanks' medium without calcium or magnesium (ref: BE10-543F, Lonza) and neutralized by the addition of complete culture medium. The cells are counted and their viability assessed by 0.25% trypan blue exclusion assay.

Animals.

Healthy immunodeficient female mice, such as SWISS Nude (Crl:NU(Ico)-Foxn1nu) from Charles River or another suitable provider, 5-7 weeks old, are obtained and maintained in good health status according to the local IACUC regulations.

Induction of FaDu (Squamous Cell Carcinoma) Tumors in Animals.

Tumors are induced by subcutaneous injection of 10×10⁶ of FaDu cells in 200 μL of RPMI 1640 into the right flank of 112 female animals. FaDuor A-431 tumor cell implantation are performed 24 to 72 hours after whole body irradiation with a γ-source (2 Gy, ⁶⁰Co, BioMep, Bretenières, France).

Treatment Schedule.

Treatment with an ADC as disclosed herein (e.g., B278-LC7HC6-MMAE, 1 mg/kg) starts when the tumor reaches a mean volume of 100-200 mm³ in size. An ADC with MMAE as cytotoxic payload is made according to the procedures described in U.S. Pat. No. 7,659,241. Animals are randomized according to their individual tumor volume into groups each of 8 animals. A statistical test (analysis of variance, ANOVA) is performed to test for homogeneity between groups. Tumor-bearing animals are treated twice, once on Day 0 and then on Day 7 at the indicated doses.

Clinical Monitoring.

Animal body weight measurements, tumor volume, clinical and mortality records, and ADC treatments are recorded. The viability and behavior of the mice are recorded every day. Body weights are measured twice a week. The length and width of the tumor are measured twice a week with calipers and the volume of the tumor (mm³) estimated by the formula:

$$\text{Tumor volume} = \frac{width^2 \times \text{length}}{2}$$

Example 12: Anti-Tumor Activity in Patient Derived Xenograft (PDX) Tumor Models Tumor Cell Preparation.

Cryo vials containing tumor cells from PDX models are thawed and prepared for injection into mice. Cells are washed in PBS, counted, and resuspended in cold PBS at a concentration of 50,000 to 100,000 viable cells/100 μl. Cell suspensions are mixed with an equal volume of Cultrex ECM. Cells are prepared for injection by withdrawing ECM-Cell mixture into a chilled 1 ml slip-tip syringe fitted with a 26G 7/8 (0.5 mm×22 mm) needle. The filled syringes are kept on ice to avoid solidification of the extracellular matrix (ECM).

Tumor Implantation.

Animals are shaved prior to injection. One mouse at a time is immobilized and the site of injection disinfected with an alcohol swab. 200 μl of cell suspension in ECM is subcutaneously injected into the rear flank of the mouse. Up to five animals are injected with 200 μl of cell suspension per syringe. Mice are marked by ear notching/tagging and animals are undisturbed for seven days before observing for tumor growth.

Tumor Measurement.

Animals are monitored weekly for palpable tumors or any changes in appearance or behavior and monitored daily for signs of morbidity or mortality. Once tumors are palpable, tumors are measured 3 times a week using calipers. Tumor volume is calculated using the following equation: (longest diameter x shortest diameter$^2$)/2. Once tumors are of appropriate size to begin the study, tumor size and body weight are measured 2 times per week.

Randomization.

When average tumor volume reaches 150-250 mm$^3$, mice are randomly assigned to the respective treatment groups (e.g., B278-MMAE (1 mg/kg)) on day 1, and dosing will begin on day 1. An ADC with MMAE as cytotoxic payload is made according to the procedures described in U.S. Pat. No. 7,659,241.

Body Weight.

Body weight is measured 3 times a week following randomization and initiation of treatment. If body weight loss of >20% is observed, the animal is observed for signs of recovery for up to 72 hours. If no signs of recovery, the animal is sacrificed for humane reasons.

Clinical Observations.

Clinical observations are performed 3 times a week at the time of tumor size and body weight measurements.

Final Disposition.

At termination of the study, all living animals are euthanized.

The present disclosure has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed. The foregoing description of the specific embodiments will so fully reveal the general nature of the invention that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein.

All patents and publications are herein incorporated by reference to the same extent as if each individual publication was specifically and individually indicated to be incorporated by reference.

---

What is claimed is:

1. A humanized antibody or antigen-binding fragment thereof that specifically binds to human tissue factor, wherein the humanized antibody or antigen-binding fragment thereof comprises:
   (i) a heavy chain variable region or antigen binding fragment thereof having an amino acid sequence selected from SEQ ID NOs: 9-11;
   (ii) a light chain variable region or antigen-binding fragment thereof having an amino acid sequence selected from SEQ ID NOs: 12-16; and
   (iii) wherein said humanized antibody or antigen binding fragment thereof does not inhibit tissue factor mediated blood coagulation compared to a normal plasma control.

2. The humanized antibody or antigen-binding fragment thereof of claim 1, wherein said heavy chain variable region has the amino acid sequence of SEQ ID NO: 9.

3. The humanized antibody or antigen-binding fragment thereof of claim 2, wherein said light chain variable region has an amino acid sequence of SEQ ID NO: 12.

4. An isolated polynucleotide encoding a humanized antibody or antigen-binding fragment thereof that specifically binds to human tissue factor, wherein the humanized antibody or the antigen-binding fragment thereof comprises:
   (i) a heavy chain variable region or antigen binding fragment thereof having an amino acid sequence selected from SEQ ID NOs: 9-11;
   (ii) a light chain variable region or antigen-binding fragment thereof having an amino acid sequence selected from SEQ ID NOs: 12-16; and
   (iii) wherein said humanized antibody or antigen binding fragment thereof does not inhibit tissue factor mediated blood coagulation compared to a normal plasma control.

5. An antibody-drug conjugate of the formula Ab-(L-CA)n, wherein:
   (i) Ab is a humanized antibody or antigen binding fragment thereof that specifically binds to human tissue factor, said antibody comprising a heavy chain variable region or antigen binding fragment thereof having an amino acid sequence selected from SEQ ID NOs: 9-11 and a light chain variable region or antigen-binding fragment thereof having an amino acid sequence selected from SEQ ID NOs: 12-16; and
   (ii) (L-CA)n is a linker-cytotoxic agent moiety, wherein L is a linker, CA is a cytotoxic agent, and n denotes a number from 1 to 8.

6. The antibody-drug conjugate of claim 5, wherein the cytotoxic agent is selected from the group consisting of a maytansine, a maytansinoid, duocarmycin, camptothecin, an auristatin, an amatoxin, calicheamicin, tubulysin, and derivatives or analogs thereof.

7. The antibody-drug conjugate of claim 6, wherein the cytotoxic agent is a maytansine or a maytansinoid.

8. The antibody-drug conjugate of claim 6, wherein the cytotoxic agent is an auristatin.

9. The antibody-drug conjugate of claim 5, wherein the linker is selected from the group consisting of a hydrophilic linker, a urea linker, a sulfamide linker, and a dicarboxylic acid-based linker.

10. The antibody-drug conjugate of claim 5, wherein the antibody-drug conjugate has a drug-to-antibody ratio (DAR) of 1 to 8.

11. The antibody-drug conjugate of claim 10, wherein the antibody-drug conjugate has a DAR of 2 or 4.

12. A pharmaceutical composition comprising the antibody-drug conjugate of claim 5 and a pharmaceutically acceptable carrier.

13. A process for producing the antibody-drug conjugate of claim 5, comprising: (i) linking the linker to the cytotoxic agent; (ii) conjugating the linker-cytotoxic agent moiety to the antibody; and (iii) purifying the antibody-drug conjugate.

14. A method of treating cancer in a subject in need thereof, comprising administering a therapeutically effective amount of a composition comprising the humanized antibody or antigen-binding fragment thereof of claim 1 to the subject in need thereof, wherein the cancer is a solid tumor or a hematological malignancy.

15. The method of claim 14, wherein the solid tumor is selected from the group consisting of breast cancer, ovarian cancer, thyroid cancer, colorectal cancer, esophageal cancer, gastric cancer, melanoma, brain cancer, head and neck cancer, epidermal, sarcoma, kidney cancer, pancreatic cancer, prostate cancer, liver cancer, urothelial, and lung cancer.

16. The method of claim 14, wherein the hematologic malignancy is leukemia, lymphoma, or myeloma.

17. The method of claim 14, wherein the hematological malignancy is acute lymphocytic leukemia (ALL), acute myeloid leukemia (AML), chronic lymphocytic leukemia (CLL), small lymphocytic lymphoma (SLL), multiple myeloma (MM), Hodgkin's lymphoma (HL), non-Hodgkin's lymphoma (NHL), mantle cell lymphoma (MCL), follicular lymphoma (FL), Waldenstrom's macroglobulinemia (WM), diffuse large B-cell lymphoma (DLBCL), marginal zone lymphoma (MZL), hairy cell leukemia (HCL), Burkitt's lymphoma (BL), or Richter's transformation.

18. The method of claim 15, wherein the solid tumor is head and neck cancer.

19. The method of claim 14, wherein the cancer overexpresses human tissue factor.

* * * * *

SEQUENCE LISTING

```
<160> NUMBER OF SEQ ID NOS: 36

<210> SEQ ID NO 1
<211> LENGTH: 915
<212> TYPE: DNA
<213> ORGANISM: Artificial Sequence
<220> FEATURE:
<223> OTHER INFORMATION: Nucleotide sequence of full length human tissue
      factor with a 32 AA N terminal leader sequence and 9 AA C-terminal
      RGS-His6 tag

<400> SEQUENCE: 1
atggagaccc ctgcctggcc ccgggtcccg cgccccgaga ccgccgtcgc tcggacgctc      60
ctgctcggct gggtcttcgc ccaggtggcc ggcgcttcag gcactacaaa tactgtggca     120
gcatataatt taacttggaa atcaactaat ttcaagacaa ttttggagtg ggaacccaaa     180
cccgtcaatc aagtctacac tgttcaaata agcactaagt caggagattg gaaaagcaaa     240 tgctttttaca caacagacac agagtgtgac ctcaccgacg agattgtgaa ggatgtgaag     300
cagacgtact tggcacgggt cttctcctac ccggcaggga atgtggagag caccggttct     360
gctggggagc tctgtatga gaactcccca gagttcacac cttacctgga dacaaaacctc     420 ggacagccaa caattcagag ttttgaacag gtgggaacaa aagtgaatgt gaccgtagaa     480
```

-continued

```
gatgaacgga ctttagtcag aaggaacaac actttcctaa gcctccggga tgttttggc      540 aaggacttaa tttatacact ttattattgg aaatcttcaa gttcaggaaa gaaaacagcc     600
aaaacaaaca ctaatgagtt tttgattgat gtggataaag agaaaactac tgtttcagt     660 gttcaagcag tgattccctc ccgaacagtt aaccggaaga gtacagacag cccggtagag    720
tgtatgggcc aggagaaagg ggaattcaga gaaatattct acatcattgg agctgtggta    780
tttgtggtca tcatccttgt catcatcctg gctatatctc tacacaagtg tagaaaggca    840
ggagtggggc agagctggaa ggagaactcc ccactgaatg tttcaagagg atcccaccat    900
caccatcacc attaa                                                      915
```

<210> SEQ ID NO 2
<211> LENGTH: 304
<212> TYPE: PRT
<213> ORGANISM: Artificial Sequence
<220> FEATURE:
<223> OTHER INFORMATION: Amino acid sequence of full length human
    tissue factor with a 32 AA N terminal leader sequence and 9 AA
    C-terminal RGS-His6 tag

<400> SEQUENCE: 2

```
Met Glu Thr Pro Ala Trp Pro Arg Val Pro Arg Pro Glu Thr Ala Val
1               5                   10                  15

Ala Arg Thr Leu Leu Leu Gly Trp Val Phe Ala Gln Val Ala Gly Ala
            20                  25                  30

Ser Gly Thr Thr Asn Thr Val Ala Ala Tyr Asn Leu Thr Trp Lys Ser
        35                  40                  45

Thr Asn Phe Lys Thr Ile Leu Glu Trp Glu Pro Lys Pro Val Asn Gln
    50                  55                  60

Val Tyr Thr Val Gln Ile Ser Thr Lys Ser Gly Asp Trp Lys Ser Lys
65                  70                  75                  80

Cys Phe Tyr Thr Thr Asp Thr Glu Cys Asp Leu Thr Asp Glu Ile Val
                85                  90                  95

Lys Asp Val Lys Gln Thr Tyr Leu Ala Arg Val Phe Ser Tyr Pro Ala
            100                 105                 110

Gly Asn Val Glu Ser Thr Gly Ser Ala Gly Glu Pro Leu Tyr Glu Asn
        115                 120                 125

Ser Pro Glu Phe Thr Pro Tyr Leu Glu Thr Asn Leu Gly Gln Pro Thr
    130                 135                 140

Ile Gln Ser Phe Glu Gln Val Gly Thr Lys Val Asn Val Thr Val Glu
145                 150                 155                 160

Asp Glu Arg Thr Leu Val Arg Arg Asn Asn Thr Phe Leu Ser Leu Arg
                165                 170                 175

Asp Val Phe Gly Lys Asp Leu Ile Tyr Thr Leu Tyr Tyr Trp Lys Ser
            180                 185                 190

Ser Ser Ser Gly Lys Lys Thr Ala Lys Thr Asn Thr Asn Glu Phe Leu
        195                 200                 205

Ile Asp Val Asp Lys Gly Glu Asn Tyr Cys Phe Ser Val Gln Ala Val
    210                 215                 220

Ile Pro Ser Arg Thr Val Asn Arg Lys Ser Thr Asp Ser Pro Val Glu
225                 230                 235                 240

Cys Met Gly Gln Glu Lys Gly Glu Phe Arg Glu Ile Phe Tyr Ile Ile
                245                 250                 255

Gly Ala Val Val Phe Val Val Ile Ile Leu Val Ile Ile Leu Ala Ile
            260                 265                 270
```

Ser Leu His Lys Cys Arg Lys Ala Gly Val Gly Gln Ser Trp Lys Glu
            275                 280                 285

Asn Ser Pro Leu Asn Val Ser Arg Gly Ser His His His His His His
        290                 295                 300

<210> SEQ ID NO 3
<211> LENGTH: 783
<212> TYPE: DNA
<213> ORGANISM: Artificial Sequence
<220> FEATURE:
<223> OTHER INFORMATION: Nucleotide sequence of the extracellular domain
      of human tissue factor with a 32 amino acid N-terminal leader
      sequence and a 9 amino acid C-terminal RGS-His6 tag sequence

<400> SEQUENCE: 3
atggagaccc ctgcctggcc ccgggtcccg cgccccgaga ccgccgtcgc tcggacgctc    60
ctgctcggct gggtcttcgc ccaggtggcc ggcgcttcag gcactacaaa tactgtggca   120
gcatataatt taacttggaa atcaactaat ttcaagacaa ttttggagtg ggaacccaaa   180
cccgtcaatc aagtctacac tgttcaaata agcactaagt caggagattg gaaaagcaaa   240
tgcttttaca acagacacac agagtgtgac ctcaccgacg agattgtgaa ggatgtgaag   300
cagacgtact tggcacgggt cttctcctac ccggcaggga tgtggagag caccggttct   360 gctggggagc tctgtatga aactccca gagttcacac cttacctgga caaaacctc     420 ggacagccaa caattcagag ttttgaacag gtggaacaa agtgaatgt gaccgtagaa   480 gatgaacgga ctttagtcag aaggaacaac actttcctaa gcctcgggga tgttttggc   540 aaggacttaa tttatacact ttattattgg aaatcttcaa gttcaggaaa gaaacagcc   600 aaaacaaaca ctaatgagtt tttgattgat gtggataaag agaaaactca ctgtttcagt   660
gttcaagcag tgattccctc ccgaacagtt aaccggaaga gtacagacag cccggtagag   720
tgtatgggcc aggagaaagg ggaattcaga gaaagaggat cccaccatca ccatcaccat   780
taa                                                                 783

<210> SEQ ID NO 4
<211> LENGTH: 260
<212> TYPE: PRT
<213> ORGANISM: Artificial sequence
<220> FEATURE:
<223> OTHER INFORMATION: Amino acid sequence of the extracellular domain
      of human tissue factor with a 32 amino acid N-terminal leader
      sequence and a 9 amino acid C-terminal RGS-His6 tag sequence.

<400> SEQUENCE: 4

Met Glu Thr Pro Ala Trp Pro Arg Val Pro Arg Pro Glu Thr Ala Val
1               5                   10                  15

Ala Arg Thr Leu Leu Leu Gly Trp Val Phe Ala Gln Val Ala Gly Ala
            20                  25                  30

Ser Gly Thr Thr Asn Thr Val Ala Ala Tyr Asn Leu Thr Trp Lys Ser
        35                  40                  45

Thr Asn Phe Lys Thr Ile Leu Glu Trp Glu Pro Lys Pro Val Asn Gln
    50                  55                  60

Val Tyr Thr Val Gln Ile Ser Thr Lys Ser Gly Asp Trp Lys Ser Lys
65                  70                  75                  80

Cys Phe Tyr Thr Thr Asp Thr Glu Cys Asp Leu Thr Asp Glu Ile Val
                85                  90                  95

Lys Asp Val Lys Gln Thr Tyr Leu Ala Arg Val Phe Ser Tyr Pro Ala
            100                 105                 110

Gly Asn Val Glu Ser Thr Gly Ser Ala Gly Glu Pro Leu Tyr Glu Asn
            115                 120                 125

Ser Pro Glu Phe Thr Pro Tyr Leu Glu Thr Asn Leu Gly Gln Pro Thr
    130                 135                 140

Ile Gln Ser Phe Glu Gln Val Gly Thr Lys Val Asn Val Thr Val Glu
145                 150                 155                 160

Asp Glu Arg Thr Leu Val Arg Arg Asn Asn Thr Phe Leu Ser Leu Arg
                165                 170                 175

Asp Val Phe Gly Lys Asp Leu Ile Tyr Thr Leu Tyr Tyr Trp Lys Ser
            180                 185                 190

Ser Ser Ser Gly Lys Lys Thr Ala Lys Thr Asn Thr Asn Glu Phe Leu
            195                 200                 205

Ile Asp Val Asp Lys Gly Glu Asn Tyr Cys Phe Ser Val Gln Ala Val
    210                 215                 220

Ile Pro Ser Arg Thr Val Asn Arg Lys Ser Thr Asp Ser Pro Val Glu
225                 230                 235                 240

Cys Met Gly Gln Glu Lys Gly Glu Phe Arg Arg Gly Ser His His
                245                 250                 255

His His His His
        260

<210> SEQ ID NO 5
<211> LENGTH: 363
<212> TYPE: DNA
<213> ORGANISM: Artificial sequence
<220> FEATURE:
<223> OTHER INFORMATION: Nucleotide sequence of the heavy chain variable
      region of murine antibody TF278

<400> SEQUENCE: 5
gaggtccagc tgcagcaatc tggagctgag ctgatgaagc ctggggcctc agtgaagata      60
tcctgcaagg ctactggcta cacattcagt agctactgga tagagtgggt aaagcagagg     120
cctggacatg gccttgagtg gattggagag atttttacctg gaagtgctag tactaagtac    180
aatgagaagt tcaagggcaa ggccacattc actgcagata catcctccaa cacagcctac    240
atgcaactca gcagcctgac atctgaggac tctgccgtct attactgtgc aagagattat    300
tactacggta gtagctacgg gtttgcttac tggggccaag gactctggt cactgtctcg      360 agt                                                                    363

<210> SEQ ID NO 6
<211> LENGTH: 121
<212> TYPE: PRT
<213> ORGANISM: Artificial sequence
<220> FEATURE:
<223> OTHER INFORMATION: Amino acid sequence of the heavy chain variable
      region of murine antibody TF278

<400> SEQUENCE: 6

Glu Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Ala Ser Thr Lys Tyr Asn Glu Lys Phe
    50                  55                  60

Lys Gly Lys Ala Thr Phe Thr Ala Asp Thr Ser Ser Asn Thr Ala Tyr

```
                65                  70                  75                  80
Met Gln Leu Ser Ser Leu Thr Ser Glu Asp Ser Ala Val Tyr Tyr Cys
                        85                  90                  95

Ala Arg Asp Tyr Tyr Tyr Gly Ser Ser Tyr Gly Phe Ala Tyr Trp Gly
                100                 105                 110

Gln Gly Thr Leu Val Thr Val Ser Ser
        115                 120

<210> SEQ ID NO 7
<211> LENGTH: 330
<212> TYPE: DNA
<213> ORGANISM: Artificial sequence
<220> FEATURE:
<223> OTHER INFORMATION: Nucleotide sequence of the light chain variable
      region of murine antibody TF278

<400> SEQUENCE: 7
caggctgttg tgactcagga atctgcactc accacatcac ctggtgaaac agtcacactc        60
acttgtcgct caagtactgg ggctgttaca actagtaact atgccaactg ggtccaagaa       120
aaaccagatc atttattcac tggcctaata ggtggtacca acaaccgagg tccaggtgtt       180
cctgccagat tctcaggctc cctgattgga gacaaggctg ccctcaccat cacggggca        240 cagactgagg atgaggcagt atatttctgt gctctatggt acagcaacca ttgggtgttc       300
ggtggaggaa ccaaactgac tgtcctaggt                                        330

<210> SEQ ID NO 8
<211> LENGTH: 110
<212> TYPE: PRT
<213> ORGANISM: Artificial sequence
<220> FEATURE:
<223> OTHER INFORMATION: Amino acid sequence of the light chain variable
      region of murine antibody TF278

<400> SEQUENCE: 8

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Gly Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Val Tyr Phe Cys Ala Leu Trp Tyr Ser Asn
                85                  90                  95

His Trp Val Phe Gly Gly Gly Thr Lys Leu Thr Val Leu Gly
                100                 105                 110

<210> SEQ ID NO 9
<211> LENGTH: 121
<212> TYPE: PRT
<213> ORGANISM: Artificial sequence
<220> FEATURE:
<223> OTHER INFORMATION: Amino acid sequence of the heavy chain variable
      region VH6 of humanized TF antibody B278

<400> SEQUENCE: 9

Glu Val Gln Leu Gln Gln Ser Gly Ala Glu Val Met Lys Pro Gly Ala
1               5                   10                  15
```

-continued

Ser Val Lys Ile Ser Cys Lys Ala Ser Gly Tyr Thr Phe Ser Ser Tyr
            20                  25                  30

Trp Ile Glu Trp Val Lys Gln Ala Pro Gly Gln Gly Leu Glu Trp Ile
        35                  40                  45

Gly Glu Ile Leu Pro Gly Ser Ala Ser Thr Lys Tyr Asn Glu Lys Phe
    50                  55                  60

Lys Gly Arg Val Thr Phe Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Tyr Gly Ser Ser Tyr Gly Phe Ala Tyr Trp Gly
            100                 105                 110

Gln Gly Thr Leu Val Thr Val Ser Ser
        115                 120

<210> SEQ ID NO 10
<211> LENGTH: 121
<212> TYPE: PRT
<213> ORGANISM: Artificial sequence
<220> FEATURE:
<223> OTHER INFORMATION: Amino acid sequence of heavy chain variable
      region VH4 of humanized TF antibody B278

<400> SEQUENCE: 10

Gln Val Gln Leu Gln Glu Ser Gly Ala Glu Val Lys Lys Pro Gly Ala
1               5                   10                  15

Ser Val Lys Val Ser Cys Lys Ala Ser Gly Tyr Thr Phe Ser Ser Tyr
            20                  25                  30

Trp Ile Glu Trp Val Arg Gln Ala Pro Gly Gln Gly Leu Glu Trp Met
        35                  40                  45

Gly Glu Ile Leu Pro Gly Ser Ala Ser Thr Lys Tyr Asn Glu Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Tyr Gly Ser Ser Tyr Gly Phe Ala Tyr Trp Gly
            100                 105                 110

Gln Gly Thr Leu Val Thr Val Ser Ser
        115                 120

<210> SEQ ID NO 11
<211> LENGTH: 121
<212> TYPE: PRT
<213> ORGANISM: Artificial sequence
<220> FEATURE:
<223> OTHER INFORMATION: Amino acid sequence of heavy chain variable
      region VH5 of humanized TF antibody B278

<400> SEQUENCE: 11

Gln Val Gln Leu Gln Glu Ser Gly Ala Glu Val Lys Lys Pro Gly Ala
1               5                   10                  15

Ser Val Lys Val Ser Cys Lys Ala Ser Gly Tyr Thr Phe Ser Ser Tyr
            20                  25                  30

Trp Ile Glu Trp Val Arg Gln Ala Pro Gly Gln Gly Leu Glu Trp Met
        35                  40                  45

Gly Glu Ile Leu Pro Gly Ser Ala Ser Thr Lys Tyr Asn Glu Lys Phe
    50                  55                  60

Lys Gly Arg Val Thr Met Thr Ala Asp Thr Ser Thr Asn Thr Val Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Tyr Gly Ser Ser Tyr Gly Phe Ala Tyr Trp Gly
            100                 105                 110

Gln Gly Thr Leu Val Thr Val Ser Ser
        115                 120

<210> SEQ ID NO 12
<211> LENGTH: 110
<212> TYPE: PRT
<213> ORGANISM: Artificial sequence
<220> FEATURE:
<223> OTHER INFORMATION: Amino acid sequence of light chain variable
      region VL7 of humanized TF antibody B278

<400> SEQUENCE: 12

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Leu Pro Lys Gly
        35                  40                  45

Leu Ile Ser Gly Thr Asn Asn Arg Gly Pro Trp Thr Thr Ala Arg Phe
    50                  55                  60

Ser Gly Ser Ile Leu Gly Asp Lys Ala Val Leu Thr Leu Trp Gly Ala
65                  70                  75                  80

His Thr Glu Asp Glu Ala Val Tyr Tyr Cys Ala Leu Trp Tyr Ser Asn
                85                  90                  95

His Trp Val Phe Gly Gly Gly Thr Lys Leu Thr Val Leu Gly
            100                 105                 110

<210> SEQ ID NO 13
<211> LENGTH: 110
<212> TYPE: PRT
<213> ORGANISM: Artificial sequence
<220> FEATURE:
<223> OTHER INFORMATION: Amino acid sequence of light chain variable
      region VL3 of humanized TF antibody B278

<400> SEQUENCE: 13

Gln Ala Val Val Thr Gln Glu Pro Ser Leu Thr Val Ser Pro Gly Gly
1               5                   10                  15

Ser Val Thr Leu Thr Cys Arg Ser Ser Thr Gly Ala Val Thr Thr Ser
            20                  25                  30

Asn Tyr Ala Asn Trp Ile Gln Gln Lys Pro Gly Gln Gly Pro Lys Thr
        35                  40                  45

Leu Ile Ser Gly Thr Asn Asn Arg Gly Pro Trp Thr Thr Ala Arg Phe
    50                  55                  60

Ser Gly Ser Ile Leu Gly Asp Lys Ala Val Leu Thr Leu Trp Gly Ala
65                  70                  75                  80

His Ala Glu Asp Glu Ala Asp Tyr Tyr Cys Ala Leu Trp Tyr Ser Asn
                85                  90                  95

His Trp Val Phe Gly Gly Gly Thr His Leu Thr Val Gln Gly
            100                 105                 110

<210> SEQ ID NO 14

```
<211> LENGTH: 110
<212> TYPE: PRT
<213> ORGANISM: Artificial sequence
<220> FEATURE:
<223> OTHER INFORMATION: Amino acid sequence of light chain variable
      region VL5 of humanized TF antibody B278

<400> SEQUENCE: 14

Gln Ala Val Val Thr Gln Glu Pro Ser Leu Thr Val Ser Pro Gly Gly
1               5                   10                  15

Ser Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Thr Pro Thr Ser
        35                  40                  45

Leu Ile Ser Gly Thr Asn Asn Arg Gly Pro Trp Thr Pro Ala Arg Phe
    50                  55                  60

Ser Gly Ser Ile Leu Gly Asp Lys Ala Val Leu Thr Leu Trp Gly Ala
65                  70                  75                  80

His Ala Glu Asp Glu Ala Asp Tyr Phe Cys Ala Leu Trp Tyr Ser Asn
                85                  90                  95

His Trp Val Phe Gly Gly Gly Thr Lys Leu Thr Val Leu Gly
            100                 105                 110

<210> SEQ ID NO 15
<211> LENGTH: 110
<212> TYPE: PRT
<213> ORGANISM: Artificial sequence
<220> FEATURE:
<223> OTHER INFORMATION: Amino acid sequence of light chain variable
      region VL6 of humanized TF antibody B278

<400> SEQUENCE: 15

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Gly His Gly Phe Lys Gly
        35                  40                  45

Leu Ile Ser Gly Thr Asn Asn Arg Gly Pro Trp Thr Thr Ala Arg Phe
    50                  55                  60

Ser Gly Ser Ile Leu Gly Asp Lys Ala Val Leu Thr Leu Trp Gly Ala
65                  70                  75                  80

His Ala Glu Asp Glu Ala Asp Tyr Phe Cys Ala Leu Trp Tyr Ser Asn
                85                  90                  95

His Trp Val Phe Gly Gly Gly Thr Lys Leu Thr Val Leu Gly
            100                 105                 110

<210> SEQ ID NO 16
<211> LENGTH: 110
<212> TYPE: PRT
<213> ORGANISM: Artificial sequence
<220> FEATURE:
<223> OTHER INFORMATION: Amino acid sequence of light chain variable
      region VL8 of humanized TF antibody B278

<400> SEQUENCE: 16

Gln Ser Ala Leu Ile Gln Pro Pro Ser Val Ser Gly Ser Pro Gly Gln
1               5                   10                  15

Ser Val Thr Ile Ser Cys Arg Ser Ser Thr Gly Ala Val Thr Thr Ser
            20                  25                  30
```

```
Asn Tyr Ala Asn Trp Val Gln Gln His Pro Gly Thr Val Pro Lys Pro
                 35                  40                  45

Met Ile Tyr Gly Thr Asn Asn Arg Gly Pro Gly Val Pro Asp Arg Phe
 50                  55                  60

Ser Gly Ser Lys Ser Gly Asn Thr Ala Ser Met Thr Ile Ser Gly Leu
 65                  70                  75                  80

Gln Ala Glu Asp Glu Ala Asp Tyr Phe Cys Ala Leu Trp Tyr Ser Asn
                 85                  90                  95

His Trp Val Phe Gly Gly Gly Thr Lys Leu Thr Val Leu Gly
                100                 105                 110

<210> SEQ ID NO 17
<211> LENGTH: 451
<212> TYPE: PRT
<213> ORGANISM: Artificial sequence
<220> FEATURE:
<223> OTHER INFORMATION: Amino acid sequence of full length heavy chain
      HC6

<400> SEQUENCE: 17

Glu Val Gln Leu Gln Gln Ser Gly Ala Glu Val Met Lys Pro Gly Ala
 1               5                  10                  15

Ser Val Lys Ile Ser Cys Lys Ala Ser Gly Tyr Thr Phe Ser Ser Tyr
                 20                  25                  30

Trp Ile Glu Trp Val Lys Gln Ala Pro Gly Gln Gly Leu Glu Trp Ile
                 35                  40                  45

Gly Glu Ile Leu Pro Gly Ser Ala Ser Thr Lys Tyr Asn Glu Lys Phe
 50                  55                  60

Lys Gly Arg Val Thr Phe Thr Ala Asp Thr Ser Thr Asn Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Tyr Tyr Tyr Gly Ser Ser Tyr Gly Phe Ala Tyr Trp Gly
                100                 105                 110

Gln Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
                130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Val Glu Pro Lys Ser Cys
                210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285
```

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 18
<211> LENGTH: 215
<212> TYPE: PRT
<213> ORGANISM: Artificial sequence
<220> FEATURE:
<223> OTHER INFORMATION: Amino acid sequence of full length light chain
      LC7

<400> SEQUENCE: 18

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Leu Pro Lys Gly
        35                  40                  45

Leu Ile Ser Gly Thr Asn Asn Arg Gly Pro Trp Thr Ala Arg Phe
    50                  55                  60

Ser Gly Ser Ile Leu Gly Asp Lys Ala Val Leu Thr Leu Trp Gly Ala
65                  70                  75                  80

His Thr Glu Asp Glu Ala Val Tyr Tyr Cys Ala Leu Trp Tyr Ser Asn
                85                  90                  95

His Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg

```
              180                 185                 190
Ser Tyr Ser Cys Gln Val Thr His Glu Gly Ser Thr Val Glu Lys Thr
        195                 200                 205

Val Ala Pro Thr Glu Cys Ser
        210                 215

<210> SEQ ID NO 19
<211> LENGTH: 10
<212> TYPE: PRT
<213> ORGANISM: Artificial sequence
<220> FEATURE:
<223> OTHER INFORMATION: VH-CDR1

<400> SEQUENCE: 19

Gly Tyr Thr Phe Ser Ser Tyr Trp Ile Glu
1               5                   10

<210> SEQ ID NO 20
<211> LENGTH: 17
<212> TYPE: PRT
<213> ORGANISM: Artificial sequence
<220> FEATURE:
<223> OTHER INFORMATION: VH-CDR2

<400> SEQUENCE: 20

Glu Ile Leu Pro Gly Ser Ala Ser Thr Lys Tyr Asn Glu Lys Phe Lys
1               5                   10                  15

Gly

<210> SEQ ID NO 21
<211> LENGTH: 14
<212> TYPE: PRT
<213> ORGANISM: Artificial sequence
<220> FEATURE:
<223> OTHER INFORMATION: VH-CDR3

<400> SEQUENCE: 21

Ala Arg Asp Tyr Tyr Tyr Gly Ser Ser Tyr Gly Phe Ala Tyr
1               5                   10

<210> SEQ ID NO 22
<211> LENGTH: 14
<212> TYPE: PRT
<213> ORGANISM: Artificial sequence
<220> FEATURE:
<223> OTHER INFORMATION: VL-CDR1

<400> SEQUENCE: 22

Arg Ser Ser Thr Gly Ala Val Thr Thr Ser Asn Tyr Ala Asn
1               5                   10

<210> SEQ ID NO 23
<211> LENGTH: 7
<212> TYPE: PRT
<213> ORGANISM: Artificial sequence
<220> FEATURE:
<223> OTHER INFORMATION: VL-CDR2

<400> SEQUENCE: 23

Gly Thr Asn Asn Arg Gly Pro
1               5

<210> SEQ ID NO 24
<211> LENGTH: 9
<212> TYPE: PRT
```

<213> ORGANISM: Artificial sequence
<220> FEATURE:
<223> OTHER INFORMATION: VL-CDR3

<400> SEQUENCE: 24

Ala Leu Trp Tyr Ser Asn His Trp Val
1               5

<210> SEQ ID NO 25
<211> LENGTH: 363
<212> TYPE: DNA
<213> ORGANISM: Artificial sequence
<220> FEATURE:
<223> OTHER INFORMATION: Nucleotide sequence of heavy chain variable
      region of humanized TF antibody B278

<400> SEQUENCE: 25

```
gaggtccagc tgcaacagtc gggagcagag gtgatgaagc ccggagcctc agtgaagatt     60
agctgcaaag cctcgggata cactttctcg tcatactgga ttgaatgggt caaacaggcc    120
cccggccaag gactggagtg gattggcgaa atccttcctg ggagcgcctc gaccaagtac    180
aacgagaagt tcaagggacg cgtgacattc accgccgata ccagcaccaa cactgcctac    240
atggagctta gctcattgcg gtccgaggat accgctgtgt actactgtgc gcgggactac    300
tattacggct cctcatacgg cttcgcatac tggggacagg gtaccttggt cacggtgtcc    360
tcc                                                                  363
```

<210> SEQ ID NO 26
<211> LENGTH: 330
<212> TYPE: DNA
<213> ORGANISM: Artificial sequence
<220> FEATURE:
<223> OTHER INFORMATION: Nucleotide sequence of light chain variable
      region of humanized TF antibody B278

<400> SEQUENCE: 26

```
caggctgtgg tcactcagga gccttcgctg actgtcagcc cgggcggtac cgtgaccctg     60
acctgtcgct cctcaactgg agcagtgacc acctccaact acgcgaactg ggtgcagcag    120
aaacccggcc aacttcctaa gggactgatc tccggcacta caacagggg  accttggacc    180 accgcccggt tctccggttc catccttggg gacaaggcgg tgctgacact gtgggggcc     240 cacacggagg acgaggccgt ctactactgc gcgctctggt actccaacca ttgggtgttt    300
ggcggaggca ctaagttgac cgtgctgggc                                     330
```

<210> SEQ ID NO 27
<211> LENGTH: 1356
<212> TYPE: DNA
<213> ORGANISM: Artificial sequence
<220> FEATURE:
<223> OTHER INFORMATION: Nucleotide sequence of full length heavy chain
      of humanized TF antibody

<400> SEQUENCE: 27

```
gaggtccagc tgcaacagtc gggagcagag gtgatgaagc ccggagcctc agtgaagatt     60
agctgcaaag cctcgggata cactttctcg tcatactgga ttgaatgggt caaacaggcc    120
cccggccaag gactggagtg gattggcgaa atccttcctg ggagcgcctc gaccaagtac    180
aacgagaagt tcaagggacg cgtgacattc accgccgata ccagcaccaa cactgcctac    240
atggagctta gctcattgcg gtccgaggat accgctgtgt actactgtgc gcgggactac    300
tattacggct cctcatacgg cttcgcatac tggggtcagg gaaccttggt cacggtgtcc    360
```

```
tccgcgtcca ccaagggtcc ctccgtgttc cctctcgcgc cgtcctcaaa gtctacctcc      420
ggtggaactg ccgcgctcgg ttgtctcgtg aaggactact cccgagcc tgtgactgtc       480 tcctggaact ccggggccct caccagcgga gtgcacactt tccccgccgt gctgcaatcc      540
tccggcctgt acagcctgtc ctccgtcgtg actgtgccta gctcctccct gggaacccag     600
acctacatct gcaacgtgaa ccacaagccc tccaacacca aggtcgacaa gaaggtcgaa     660
ccgaagtcgt gcgacaagac tcatacgtgc cctccttgcc cggccccgga actgctggga    720
ggcccatccg tgttcctgtt cccacccaag cctaaggata ccctgatgat cagcagaaca    780
ccggaagtga cctgtgtggt ggtggacgtc agccacgaag atcccgaggt caagttcaat   840
tggtacgtgg acggggtgga ggtgcacaac gcaaagacca gccccggga ggaacagtac    900 aactccacct atcgcgtggt gtcggtgctg acggtgctgc accaggactg gttgaacgga    960
aaggagtata agtgcaaagt gtcgaacaag gccctgcccg ctcctatcga aagaccatc    1020 tccaaggcca agggccagcc gcgggaaccc caggtctaca ctctcccacc gagccgcgac   1080
gaactgacta agaatcaagt gtcgctgact tgcctcgtca agggcttcta cccgtccgac   1140
atcgccgtgg aatgggagag caacggccag ccggaaaaca actacaagac caccctccc    1200 gtgctggatt ccgacgggtc cttcttcctg tactcaaaac tgaccgtgga taagtccaga   1260
tggcagcagg gcaatgtctt ttcatgctcc gtgatgcacg aggctctgca taaccactac   1320
acccagaagt cgctgtccct gtccccgggg aagtga                              1356

<210> SEQ ID NO 28
<211> LENGTH: 648
<212> TYPE: DNA
<213> ORGANISM: Artificial sequence
<220> FEATURE:
<223> OTHER INFORMATION: Nucleotide sequence of full length light chain
      of humanized TF antibody

<400> SEQUENCE: 28
caggctgtgg tcactcagga gccttcgctg actgtcagcc cgggtggcac cgtgaccctg     60
acctgtcgct cctcaactgg agcagtgacc acctccaact acgcgaactg ggtgcagcag    120
aaacccggcc aacttcctaa gggactgatc tccggcacta caacaggggg accttggacc    180
accgcccggt tctccggttc catccttggg gacaaggcgg tgctgacact gtgggggcc    240 cacacggagg acgaggccgt ctactactgc gcgctctggt actccaacca ttgggtgttt    300
ggcggaggca ctaagttgac cgtgctgggc cagcctaagg ccgcaccatc ggtgaccctg    360
ttcccgccga gctcggaaga actccaggcc aacaaggcca ctctggtctg cctgatttcc    420
gacttctatc ccggtgctgt gaccgtggct tggaaggccg atagctcgcc cgtgaaggcc    480
ggagtggaaa ccaccacccc gtccaaacag tccaacaata gtacgccgc ctcctcctac     540 ttgagcctca cgcccgagca gtggaagtct caccgctcat actcctgcca agtcacccac    600
gaagggagca ctgtggaaaa gaccgtggca cccactgagt gctcgtga                 648

<210> SEQ ID NO 29
<211> LENGTH: 57
<212> TYPE: DNA
<213> ORGANISM: Artificial sequence
<220> FEATURE:
<223> OTHER INFORMATION: Synthetic

<400> SEQUENCE: 29
atgggatgga ctctcgtgtt cctttttctc ctctctgtca ctgccggggt gcattcg        57
```

<210> SEQ ID NO 30
<211> LENGTH: 19
<212> TYPE: PRT
<213> ORGANISM: Artificial sequence
<220> FEATURE:
<223> OTHER INFORMATION: Synthetic

<400> SEQUENCE: 30

Met Gly Trp Thr Leu Val Phe Leu Phe Leu Leu Ser Val Thr Ala Gly
1               5                   10                  15

Val His Ser

<210> SEQ ID NO 31
<211> LENGTH: 60
<212> TYPE: DNA
<213> ORGANISM: Artificial sequence
<220> FEATURE:
<223> OTHER INFORMATION: Synthetic

<400> SEQUENCE: 31
atggtgtcaa gcgcgcagtt tctgggactg ctcctgctgt gtttccaagg aaccagatgc      60

<210> SEQ ID NO 32
<211> LENGTH: 20
<212> TYPE: PRT
<213> ORGANISM: Artificial sequence
<220> FEATURE:
<223> OTHER INFORMATION: Synthetic

<400> SEQUENCE: 32

Met Val Ser Ser Ala Gln Phe Leu Gly Leu Leu Leu Cys Phe Gln
1               5                   10                  15

Gly Thr Arg Cys
            20

<210> SEQ ID NO 33
<211> LENGTH: 60
<212> TYPE: DNA
<213> ORGANISM: Artificial sequence
<220> FEATURE:
<223> OTHER INFORMATION: Synthetic

<400> SEQUENCE: 33
atggagacag acacactcct gctatgggta ctgctgctct gggttccagg atctactggc      60

<210> SEQ ID NO 34
<211> LENGTH: 20
<212> TYPE: PRT
<213> ORGANISM: Artificial sequence
<220> FEATURE:
<223> OTHER INFORMATION: Synthetic

<400> SEQUENCE: 34

Met Glu Thr Asp Thr Leu Leu Leu Trp Val Leu Leu Leu Trp Val Pro
1               5                   10                  15

Gly Ser Thr Gly
            20

<210> SEQ ID NO 35
<211> LENGTH: 363
<212> TYPE: DNA
<213> ORGANISM: Artificial sequence
<220> FEATURE:
<223> OTHER INFORMATION: Nucleotide sequence of heavy chain variable region of humanized TF antibody B278

<400> SEQUENCE: 35

```
gaggtccagc tgcaacagtc gggagcagag gtgatgaagc ccggagcctc agtgaagatt      60
agctgcaaag cctcgggata cactttctcg tcatactgga ttgaatgggt caaacaggcc     120
cccggccaag gactggagtg gattggcgaa atccttcctg ggagcgcctc gaccaagtac     180
aacgagaagt tcaagggacg cgtgacattc accgccgata ccagcaccaa cactgcctac     240
atggagctta gctcattgcg gtccgaggat accgctgtgt actactgtgc gcgggactac     300
tattacggct cctcatacgg cttcgcatac tggggtcagg gaaccttggt cacggtgtcc     360
tcc                                                                   363
```

<210> SEQ ID NO 36
<211> LENGTH: 330
<212> TYPE: DNA
<213> ORGANISM: Artificial sequence
<220> FEATURE:
<223> OTHER INFORMATION: Nucleotide sequence of light chain variable
      region of humanized TF antibody B278

<400> SEQUENCE: 36

```
caggctgtgg tcactcagga gccttcgctg actgtcagcc cgggtggcac cgtgaccctg      60
acctgtcgct cctcaactgg agcagtgacc acctccaact acgcgaactg ggtgcagcag     120
aaacccggcc aacttcctaa gggactgatc tccggcacta acaacagggg accttggacc     180 accgccggt tctccggttc catccttggg gacaaggcgg tgctgacact gtgggggcc       240 cacacggagg acgaggccgt ctactactgc gcgctctggt actccaacca ttgggtgttt     300
ggcggaggca ctaagttgac cgtgctgggc                                      330
```